(12) United States Patent
Webster et al.

(10) Patent No.: US 11,564,947 B2
(45) Date of Patent: Jan. 31, 2023

(54) METHODS AND COMPOSITIONS FOR CELLULAR IMMUNOTHERAPY

(71) Applicant: eFFECTOR Therapeutics, Inc., San Diego, CA (US)

(72) Inventors: Kevin R. Webster, San Diego, CA (US); Rajesh Sharma, San Diego, CA (US); Gary Chiang, San Diego, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 66 days.

(21) Appl. No.: 17/025,607

(22) Filed: Sep. 18, 2020

(65) Prior Publication Data

US 2021/0177898 A1 Jun. 17, 2021

Related U.S. Application Data

(63) Continuation of application No. 15/989,098, filed on May 24, 2018, now Pat. No. 10,780,119.

(60) Provisional application No. 62/657,564, filed on Apr. 13, 2018, provisional application No. 62/510,680, filed on May 24, 2017.

(51) Int. Cl.

| | | |
|---|---|---|
| *C07H 21/04* | (2006.01) |
| *A61K 35/17* | (2015.01) |
| *C07K 14/74* | (2006.01) |
| *A61P 35/00* | (2006.01) |
| *C07K 14/725* | (2006.01) |
| *C07K 14/73* | (2006.01) |
| *C07K 14/16* | (2006.01) |
| *C07K 14/705* | (2006.01) |
| *C12N 5/0783* | (2010.01) |
| *C07D 471/04* | (2006.01) |
| *C07D 487/04* | (2006.01) |
| *C07D 495/20* | (2006.01) |
| *C07D 491/20* | (2006.01) |
| *C07D 471/20* | (2006.01) |
| *A61K 31/501* | (2006.01) |
| *A61K 45/06* | (2006.01) |

(52) U.S. Cl.
CPC ............ *A61K 35/17* (2013.01); *A61K 31/501* (2013.01); *A61P 35/00* (2018.01); *C07D 471/04* (2013.01); *C07D 471/20* (2013.01); *C07D 487/04* (2013.01); *C07D 491/20* (2013.01); *C07D 495/20* (2013.01); *C07K 14/162* (2013.01); *C07K 14/7051* (2013.01); *C07K 14/70514* (2013.01); *C07K 14/70517* (2013.01); *C07K 14/70539* (2013.01); *C07K 14/70564* (2013.01); *C07K 14/70589* (2013.01); *C12N 5/0636* (2013.01); *C12N 5/0638* (2013.01); *A61K 45/06* (2013.01); *C12N 2501/727* (2013.01)

(58) Field of Classification Search
CPC .............................. C12N 15/113; A61K 48/00
See application file for complete search history.

(56) References Cited

U.S. PATENT DOCUMENTS

| | | |
|---|---|---|
| 5,283,173 A | 2/1994 | Fields et al. |
| 5,420,032 A | 5/1995 | Marshall et al. |
| 5,468,614 A | 11/1995 | Fields et al. |
| 6,410,319 B1 | 6/2002 | Raubitschek et al. |
| 6,833,252 B1 | 12/2004 | Dujon et al. |
| 7,446,191 B2 | 11/2008 | Jensen |
| 7,514,537 B2 | 4/2009 | Jensen |
| 8,119,772 B2 | 2/2012 | Yang et al. |
| 8,697,359 B1 | 4/2014 | Zhang |
| 8,822,647 B2 | 9/2014 | Jensen |
| 2004/0002092 A1 | 1/2004 | Arnould et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2007/0036773 A1 | 2/2007 | Cooper et al. |
| 2007/0117128 A1 | 5/2007 | Smith et al. |
| 2010/0065818 A1 | 3/2010 | Kim et al. |
| 2011/0301073 A1 | 12/2011 | Gregory et al. |
| 2012/0321667 A1 | 12/2012 | Sentman |
| 2014/0068797 A1 | 3/2014 | Doudna et al. |
| 2014/0186843 A1 | 7/2014 | Zhang et al. |
| 2015/0376181 A1 | 12/2015 | Reich et al. |
| 2016/0362472 A1 | 12/2016 | Bitter |
| 2017/0166622 A1 | 6/2017 | Baeuerle et al. |

FOREIGN PATENT DOCUMENTS

| | | | |
|---|---|---|---|
| CA | 2908668 A1 * | 10/2014 | ....... C07K 14/70517 |
| WO | 97/09433 A1 | 3/1997 | |
| WO | 2013/074916 A1 | 5/2013 | |
| WO | 2013/166321 A1 | 11/2013 | |
| WO | 2014/031687 A1 | 2/2014 | |

(Continued)

OTHER PUBLICATIONS

Ueda et al. (PNAS, 2010, 107, 32, 13984-13990).*
Yee et al. (PNAS, 2002, 99, 25, 16168-16173).*
Perret et al. (Tissue Antigens, 2008, 72, 3, 187-194).*
Yao et al. (Cancer J, 2014, 20(4), 262-264).*
Abad et al. (Jan. 2008) "T-cell Receptor Gene Therapy of Established Tumors in a Murine Melanoma Model", Journal of Immunotherapy, 31 (1):1-6.
Altschul et al. (Sep. 1, 1997) "Gapped BLAST and PSI-BLAST: A New Generation of Protein Database Search Programs", Nucleic Acids Research, 25(17):3389-3402.

(Continued)

*Primary Examiner* — Amy H Bowman
(74) *Attorney, Agent, or Firm* — Mintz Levin Cohn Ferris Glovsky and Popeo, P.C.

(57) ABSTRACT

The present disclosure relates to genetically modified T cells comprising a transgene encoding an engineered antigen specific receptor, wherein expression of an endogenous gene selected from MNK1, MNK2, or both are inhibited in the genetically modified T cell in order to enhance central memory T cell subsets in cellular immunotherapy compositions.

20 Claims, 10 Drawing Sheets

Specification includes a Sequence Listing.

(56) References Cited

FOREIGN PATENT DOCUMENTS

| WO | 2014/039523 A1 | 3/2014 |
|---|---|---|
| WO | 2014/059173 A2 | 4/2014 |
| WO | 2014/134165 A1 | 9/2014 |
| WO | 2015/066262 A1 | 5/2015 |
| WO | 2015/071474 A2 | 5/2015 |
| WO | 2015/157391 A1 | 10/2015 |
| WO | 2016/109410 A2 | 7/2016 |
| WO | 2016/138091 A2 | 9/2016 |
| WO | 2016/172010 A1 | 10/2016 |
| WO | 2016/196388 A1 | 12/2016 |
| WO | 2017/079703 A1 | 5/2017 |
| WO | 2018/218038 A1 | 11/2018 |

OTHER PUBLICATIONS

Argast et al. (Jul. 1, 1998) "I-Ppol and I-Crel Homing Site Sequence Degeneracy Determined by Random Mutagenesis and Sequential In Vitro Enrichment", Journal of Molecular Biology, 280(3):345-353.

Ashworth et al. (Jun. 1, 2006) "Computational Redesign of Endonuclease DNA Binding and Cleavage Specificity", Nature, 41(7093):656-659.

Belfort et al. (Sep. 1, 2007) "Homing Endonucleases: Keeping the House in Order", Nucleic Acids Research, 25(17):3379-3388.

Berger et al. (Jan. 2008) "Adoptive Transfer of Effector CD8+ T Cells Derived from Central Memory Cells Establishes Persistent T Cell Memory in Primates", Journal of Clinical Investigation, 118(1):294-305.

Brentjens et al. (Sep. 15, 2007) "Genetically Targeted T Cells Eradicate Systemic Acute Lymphoblastic Leukemia Xenografts", Clinical Cancer Research, 13(18 Pt 1):5426-5435.

Buxade et al. (Aug. 2005) "The Mnks Are Novel Components in the Control of TNFα Biosynthesis and Phosphorylate and Regulate hnRNP A1", Immunity, 23(2):177-189.

Cavallo et al. ( Mar. 2011) "2011: The Immune Hallmarks of Cancer", Cancer Immunology, Immunotherapy, 60(3):319-326.

Chevalier et al. (Oct. 2002) "Design, Activity, and Structure of a Highly Specific Artificial Endonuclease", Molecular Cell, 10(4):895-905.

Chothia et al. (Dec. 1, 1988) "The Outline Structure of the T-cell Alpha Beta Receptor", The EMBO Journal, 7(12):3745-3755.

Condomines et al. (Jun. 25, 2015) "Tumor-Targeted Human T Cells Expressing CD28-Based Chimeric Antigen Receptors Circumvent CTLA-4 Inhibition", PLoS One, e0130518, 10(6):15 Pages.

De Witte et al. (Aug. 15, 2008) "TCR Gene Therapy of Spontaneous Prostate Carcinoma Requires In Vivo T Cell Activation", Journal of Immunology, 181(4):2563-2571.

Desjarlais et al. (Mar. 15, 1993) "Use of a Zinc-Finger Consensus Sequence Framework and Specificity Rules to Design Specific DNA Binding Proteins", Proceedings of the National Academy of Sciences of the United States of America, 90(6):2256-2260.

Dossett et al. (Apr. 2009) "Adoptive Immunotherapy of Disseminated Leukemia with TCR-transduced, CD8+ T Cells Expressing a Known Endogenous TCR", Molecular Therapy, 17(4):742-749.

Dunn et al. (Apr. 2006) "Directed Evolution of Human T Cell Receptor CDR2 Residues by Phage Display Dramatically Enhances Affinity for Cognate Peptide-MHC Without Increasing Apparent Cross-Reactivity", Protein Science, 15(4):710-721.

Engels et al. (Aug. 10, 2003) "Retroviral Vectors for High-Level Transgene Expression in T Lymphocytes", Human Gene Therapy, 14(12):1155-1168.

Epinat et al. (Jun. 1, 2003) "A Novel Engineered Meganuclease Induces Homologous Recombination in Yeast and Mammalian Cells", Nucleic Acids Research, 31(11):2952-2962.

Eyquem et al. (Feb. 22, 2017) "Targeting a CAR to the TRAC Locus with CRISPR/Cas9 Enhances Tumour Rejection", Nature, 543(7643):113-117.

Fire et al. (Mar. 1998) "Potent and Specific Genetic Interference by Double-Stranded RNA in Caenorhabditis Elegans", Nature, 391(6669):806-810.

Frecha et al. (Oct. 2010) "Advances in the Field of Lentivector-Based Transduction of T And B Lymphocytes for Gene Therapy", Molecular Therapy, 18(10):1748-1757.

Gattinoni et al. (Sep. 18, 2011) "A Human Memory T Cell Subset with Stem Cell-like Properties", Nature Medicine, 17(10):1290-1297.

Gorentla et al. (Feb. 1, 2013) "Mnk1 and 2 are Dispensable for T Cell Development and Activation but Important for the Pathogenesis of Experimental Autoimmune Encephalomyelitis", Journal of Immunology, 190(3):1026-1037.

Haidar et al. (Mar. 2009) "Structure-Based Design of a T Cell Receptor Leads to Nearly 100-Fold Improvement in Binding Affinity for pepMHC", Proteins, 74(4):948-960.

Hamilton et al. (Oct. 29, 1999) "A Species of Small Antisense RNA in Posttranscriptional Gene Silencing in Plants", Science, 286(5441):950-952.

Hanahan et al. (Mar. 4, 2011) "Hallmarks of Cancer: The Next Generation", Cell, 144(5):646-674.

Hanahan et al. (Jan. 7, 2000) "The Hallmarks of Cancer", Cell, 100(1):57-70.

Harris et al. (Nov. 18, 2016) "Deep Mutational Scans as a Guide to Engineering High Affinity T Cell Receptor Interactions with Peptide-bound Major Histocompatibility Complex", Journal of Biological Chemistry, 291(47):24566-24578.

Jinek et al. (Aug. 17, 2012) "A Programmable Dual-RNA-Guided DNA Endonuclease in Adaptive Bacterial Immunity", Science, 337(6069):816-821.

Jores et al. (Dec. 1990) "Resolution of Hypervariable Regions in T-Cell Receptor Beta Chains by a Modified Wu-Kabat Index of Amino Acid Diversity", Proceedings of the National Academy of Sciences of the United States of America, 87(23):9138-9142.

Joshi et al. (Jan. 11, 2012) "Mnk Kinases in Cytokine Signaling and Regulation of Cytokine Responses", Biomolecular Concepts, 3(2):127-139.

Juillerat et al. (Jan. 11, 2016) "Design of Chimeric Antigen Receptors with Integrated Controllable Transient Functions", Scientific Reports, 6:7 pages.

Kageyama et al. (May 15, 2015) "Adoptive Transfer of MAGE-A4 T-cell Receptor Gene-Transduced Lymphocytes in Patients with Recurrent Esophageal Cancer", Clinical Cancer Research, 21(10):2268-2277.

Kessels et al. (Dec. 19, 2000) "Changing T Cell Specificity by Retroviral T Cell Receptor Display", Proceedings of the National Academy of Sciences of the United States of America, 97(26):14578-14583.

Kim et al. (Apr. 29, 2011) "High Cleavage Efficiency of a 2A Peptide Derived from Porcine Teschovirus-1 in Human Cell Lines, Zebrafish and Mice", PLoS ONE, e18556, 6(4):8 pages.

Krisky et al. (Nov. 1998) "Development of Herpes Simplex Virus Replication—Defective Multigene Vectors for Combination Gene Therapy Applications", Gene Therapy, 5(11):1517-1530.

Li et al. (Feb. 20, 2005) "Directed Evolution of Human T-cell Receptors with Picomolar Affinities by Phage Display", Nature Biotechnology, 23(3):349-354.

Lin et al. (Nov. 11, 1999) "Policing Rogue Genes", Nature, 402:128-129.

Liu et al. (Apr. 1, 2015) "The BRAF and MEK Inhibitors Dabrafenib and Trametinib: Effects on Immune Function and in Combination with Immunomodulatory Antibodies Targeting PD-1, PD-L1, and CTLA-4", Clinical Cancer Research, 21(7):1639-1651.

Robbins, et al., "Single and Dual Amino Acid Substitutions in TCR CDRs Can Enhance Antigen-Specific T Cell Functions", Journal of Immunology, May 1, 2008, 180(9):6116-6131.

Robbins, et al., "Tumor Regression in Patients with Metastatic Synovial Cell Sarcoma and Melanoma using Genetically Engineered Lymphocytes Reactive With NY-ESO-1", Journal of Clinical Oncology, Mar. 1, 2011, 29(7):917-924.

Rodems, et al., "A FRET-Based Assay Platform for Ultra-High Density Drug Screening of Protein Kinases and Phosphatases", Assayand Drug Development Technologies, Nov. 2002, 1(1):9-19.

Sambrook, et al., "Molecular Cloning", Cold Spring Harbor Laboratory Press, 1989.

(56) References Cited

OTHER PUBLICATIONS

Sambrook, et al., "Molecular Cloning: A Laboratory Manual", Cold Spring Harbor Laboratory Press, 2001.
Scatchard, et al., "The Attractions of Protein for Small Molecules and Ions", Annals of the New York Academy of Sciences, May 1949, 51(4):660-672.
Schmitt, et al., "T Cell Receptor Gene Therapy for Cancer", Human Gene Therapy, Nov. 2009, 20(11):1240-1248.
Scholten, et al., "Codon Modification of T Cell Receptors Allows Enhanced Functional Expression in Transgenic Human T Cells", Clinical Immunology, May 2006, 119(2):135-145.
Sharp, "RNAi and Double-strand RNA", Genes & Development, 1999, 13:139-141.
Smith, et al., "Changing the Peptide Specificity of a Human T-cell Receptor by Directed Evolution", Nature Communications, Nov. 7, 2014, 5:5223.
Sommermeyer, et al., "Chimeric Antigen Receptor-Modified T Cells Derived from Defined CD8+ and CD4+ Subsets Confer Superior Antitumor Reactivity in Vivo", Leukemia, Feb. 2016, 30(2):492-500.
Louis et al. (Dec. 1, 2011) "Antitumor Activity and Long-Term Fate of Chimeric Antigen Receptor-Positive T Cells in Patients with Neuroblastoma.", Blood, 118(23):6050-6056.
Morgan et al. (Nov. 2006) "Cancer Regression in Patients After Transfer of Genetically Engineered Lymphocytes", Science, 314(5796):126-129.
Mosmann et al. (1983) "Rapid Colorimetric Assay For Cellular Growth and Survival: Application to Proliferation and Cytotoxicity Assays", Journal of Immunological Methods, 65:55-63.
Ohno et al. (Dec. 16, 2013) "Expression of miR-17-92 Enhances Anti-Tumor Activity of T-Cells Transduced with the Anti-EGFRvIII Chimeric Antigen Receptor in Mice Bearing Human GBM Xenografts", Journal for ImmunoTherapy of Cancer, 1:21.
Pâque et al. (Feb. 2007) "Meganucleases and DNA Double-Strand Break-Induced Recombination: Perspectives for Gene Therapy", Current Gene Therapy, 7(1):49-66.
Patel et al. (Mar. 3, 1999) "Impact of Chimeric Immune Receptor Extracellular Protein Domains on T Cell Function", Gene Therapy, 6(3):412-419.
Perler et al. (Apr. 11, 1994) "Protein Splicing Elements: Inteins and Exteins—A Definition of Terms and Recommended Nomenclature", Nucleic Acids Research, 22(7):1125-1127.
Pierce et al. (Feb. 13, 2014) "Computational Design of the Affinity and Specificity of a Therapeutic T Cell Receptor", PLOS Computational Biology, e1003478, 10(2):11 pages.
Robbins et al. (May 1, 2008) "Single and Dual Amino Acid Substitutions in TCR CDRs Can Enhance Antigen-Specific T Cell Functions", Journal of Immunology, 180(9):6116-6131.
Robbins et al. (Mar. 1, 2011) "Tumor Regression in Patients with Metastatic Synovial Cell Sarcoma and Melanoma using Genetically Engineered Lymphocytes Reactive With NY-ESO-1", Journal of Clinical Oncology, 29(7):917-924.
Schmitt et al. (Nov. 2009) "T Cell Receptor Gene Therapy for Cancer", Human Gene Therapy, 20(11):1240-1248.
Sharp (1999) "RNAi and Double-strand RNA", Genes & Development, 13:139-141.
Smith et al. (Nov. 7, 2014) "Changing the Peptide Specificity of a Human T-cell Receptor by Directed Evolution", Nature Communications, 5:28 pages.
Sommermeyer et al. (Feb. 2016) "Chimeric Antigen Receptor-Modified T Cells Derived from Defined CD8+ and CD4+ Subsets Confer Superior Antitumor Reactivity in Vivo", Leukemia, 30(2):492-500.
Tario et al. (2011) "Tracking Immune Cell Proliferation and Cytotoxic Potential Using Flow Cytometry", Methods in Molecular Biology, 699:119-164.
Tumeh et al. (Nov. 26, 2014) "PD-1 Blockade Induces Responses by Inhibiting Adaptive Immune Resistance", Nature, 515:568-571.
Udyavar et al. (Apr. 1, 2009) "Subtle Affinity-Enhancing Mutations in a Myelin Oligodendrocyte Glycoprotein-Specific TCR Alter Specificity and Generate New Self Reactivity", The Journal of Immunology, 182(7):4439-4447.
Verhoeyen et al. (2009) "Lentiviral Vector Gene Transfer into Human T Cells", Methods in Molecular Biology, 506:97-114.
Walchli et al. (Nov. 21, 2011) "A Practical Approach to T-Cell Receptor Cloning and Expression", PLos One, e27930, 6(11):11 pages.
Walseng et al. (Sep. 6, 2017) "A TCR-based Chimeric Antigen Receptor", Scientific Reports, 7(1):10 pages.
Wan et al. (Apr. 17, 2009) "Interleukin-1 Receptor-Associated Kinase 2 is Critical for Lipopolysaccharide-Mediated Post-transcriptional Control", Journal of Biological Chemistry, 284(16):10367-10375.
Wang et al. (Feb. 10, 2011) "Engraftment of Human Central Memory-Derived Effector CD8+ T Cells in Immunodeficient Mice", Blood, 117(6):1888-1898.
Wolff et al. (Jun. 1, 1995) "Monoclonal Antibody Homodimers: Enhanced Antitumor Activity in Nude Mice", Cancer Research, 53(11):2560-2565.
Xie et al. (Jun. 23, 2014) "sgRNAcas9: A Software Package for Designing CRISPR sgRNA and Evaluating Potential Off-Target Cleavage Sites", PLOS One, e100448, 9(6):9 pages.
Zamore et al. (Mar. 31, 2000) "RNAi: Double-Stranded RNA Directs the ATP-Dependent Cleavage of mRNA at 21 To 23 Nucleotide Intervals", Cell, 101(1):25-33.
Zhao et al. (Nov. 1, 2007) "High-Affinity TCRs Generated by Phage Display Provide CD4+ T Cells with the Ability to Recognize and Kill Tumor Cell Lines", The Journal of Immunology, 179(9):5845-5854.
Zhao et al. (Apr. 1, 2005) "Primary Human Lymphocytes Transduced with NY-ESO-1 Antigen-Specific TCR Genes Recognize and Kill Diverse Human Tumor Cell Lines", The Journal of Immunology, 174(7):4415-4423.
Zoete et al. (Sep. 12, 2013) "Structure-Based, Rational Design of T Cell Receptors", Frontiers in Immunology, 4:268.
International Preliminary Report on Patentability for Application No. PCT/US2018/034417, dated Dec. 5, 2019 (10 pages).
International Search Report and Written Opinion for PCT International Application No. PCT/US2018/034417, dated Aug. 21, 2018, (15 pages).

* cited by examiner

SEQUENCE LISTING

<160> NUMBER OF SEQ ID NOS: 1

<210> SEQ ID NO 1
<211> LENGTH: 8
<212> TYPE: PRT

```
<213> ORGANISM: Gallus gallus

<400> SEQUENCE: 1

Ser Ile Ile Asn Phe Glu Lys Leu
1               5
```

METHODS AND COMPOSITIONS FOR CELLULAR IMMUNOTHERAPY

CROSS-REFERENCE TO RELATED APPLICATIONS

This application claims priority to U.S. patent application Ser. No. 15/989,098, filed May 24, 2018, issued as U.S. Pat. No. 10,780,119, U.S. Provisional Patent Application No. 62/657,564, filed Apr. 13, 2018, and U.S. Provisional Patent Application No. 62/510,680, filed May 24, 2017, the disclosure of each of which is incorporated by reference herein in its entirety, including any drawings and sequence listing.

INCORPORATION OF THE SEQUENCE LISTING

This application contains a Sequence Listing which is hereby incorporated by reference in its entirety. The accompanying Sequence Listing text file, named "050040-516C01US_SequenceListing," was created on Mar. 2, 2021 and is 595 bytes in size.

BACKGROUND

The adoptive transfer of human T lymphocytes that are engineered by gene transfer to express chimeric antigen receptors (CARs) or recombinant T cell receptors (TCRs) specific for surface molecules expressed on tumor cells has the potential to effectively treat advanced malignancies. Durable responses in patients following adoptive transfer of CAR-modified T cells or recombinant TCR-modified T cells not only hinge upon the successful engraftment of the engineered T cells, but also their long-term persistence. Consistent with this notion, previous studies have demonstrated that adoptive transfer of less-differentiated longer-lived T cell subsets, such as T memory stem cells ($T_{SCM}$), T central memory cells ($T_{CM}$), or naïve T cells, demonstrate increased anti-tumor efficacy compared to their more differentiated counterparts, such as T effector cells or T effector memory cells ($T_{EM}$) (Gattinoni et al., Nature Med. 17:1290-7, 2011; Sommermeyer et al., Leukemia 30:492-500, 2016).

There is a need in the art for alternative, effective compositions and methods for adoptive T cell immunotherapy, particularly those resulting in generation and transfer of antigen-specific T cells that are both cytotoxic against target cells and long-lived in vivo. The present disclosure meets such needs, and further provides other related advantages.

BRIEF DESCRIPTION OF THE SEVERAL VIEWS OF THE DRAWINGS

FIG. 4A shows that tumor growth curves of animal groups. Text within parentheses indicate the in vitro pre-treatment of OT-I cells with SIINFEKL peptide (SEQ ID NO:1) and/or Compound 107 prior to adoptive transfer, while text outside of parentheses correspond to in vivo dosing with vehicle or Compound 107 as indicated. Data points, average tumor volume of 7-8 animals/group; Error bars, SEM. FIG. 4B shows that individual tumor volumes of animals within treatment groups at day 8. Bar, mean.

DETAILED DESCRIPTION

Figure 1A:
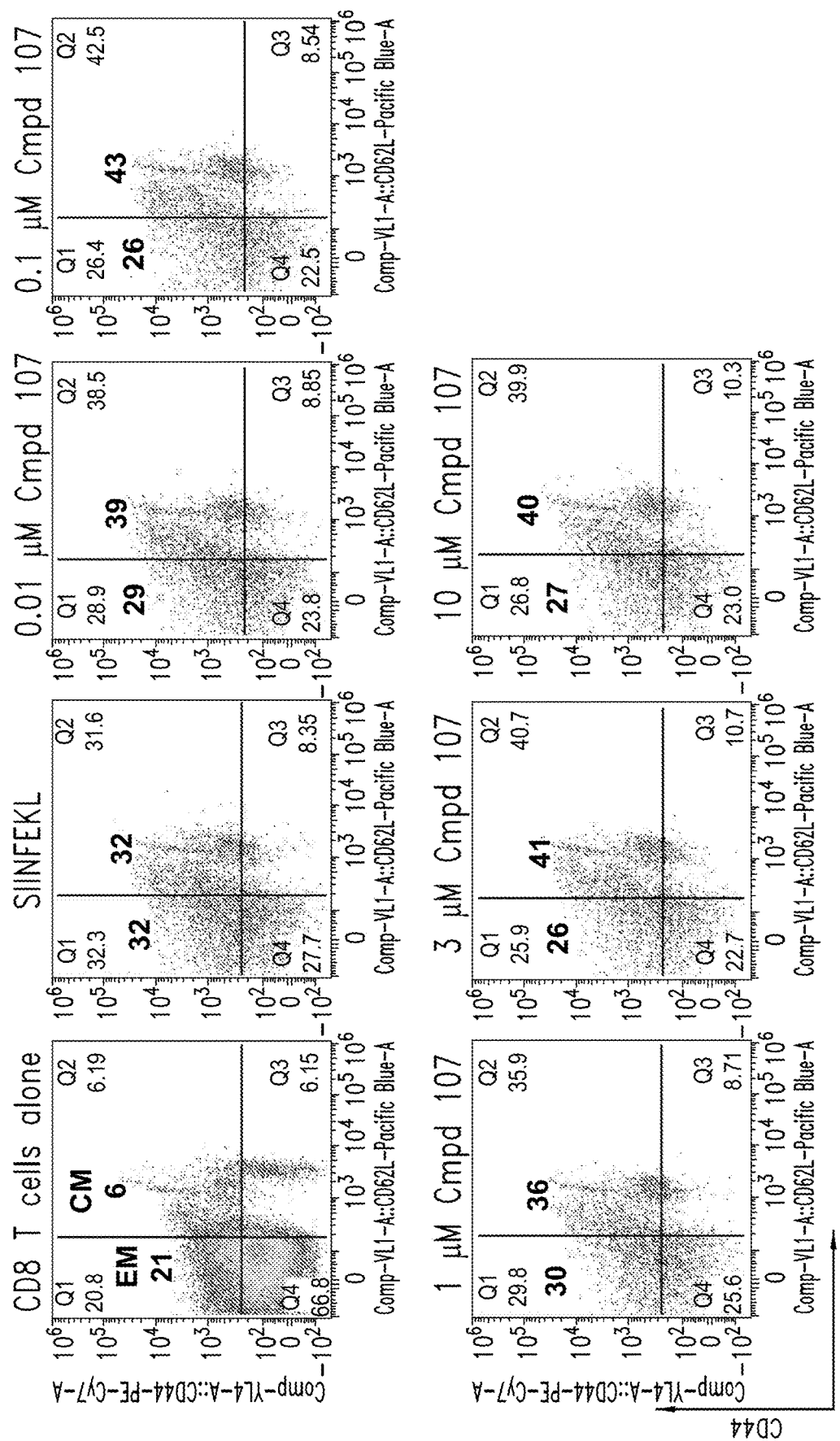
FIGS. 1A-1F show that MNK-specific inhibitors can enhance formation of central memory T cells. (A) Flow cytometry scatter plots for CD44 and CD62L expression on CD8$^+$ T cells in an OVA MHC class I epitope peptide assay (SIINFEKL, SEQ ID NO:1) in the presence of increasing amounts of Compound 107 (0.01 µM, 0.1 µM, 1.0 µM, 3.0 µM, 10 µM), a MNK-specific inhibitor. T cells having a CD44$^{Hi}$ CD62L$^{Hi}$ phenotype are considered central memory T cells ($T_{CM}$), while T cells having a CD44$^{Hi}$ CD62L$^{Lo}$ phenotype are considered effector memory T cells ($T_{EM}$). (B) Bar graph showing the percentage of $T_{EM}$ and $T_{CM}$ populations in CD8$^+$ T cells from the OVA peptide assay of part (A). (C) Flow cytometry scatter plots for CD44 and CD62L expression in CD8$^+$ cells in a mixed lymphocyte reaction (MLR) assay in the presence of increasing amounts of Compound 107 (0.01 µM, 0.1 µM, 1.0 µM, 3.0 µM, 10 µM), a MNK-specific inhibitor. (D) Bar graph showing the percentage of $T_{EM}$ and $T_{CM}$ cell populations in CD8$^+$ cells from the MLR assay of part (C). (E) Flow cytometry scatter plots for CD44 and CD62L expression in CD4$^+$ cells in the MLR assay in the presence of increasing amounts of MNK-specific inhibitor Compound 107 (0.01 µM, 0.1 µM, 1.0 µM, 3.0 µM, 10 µM). (F) Bar graph showing percentage of $T_{EM}$ and $T_{CM}$ cell populations in CD4$^+$ cells from the MLR assay of part (E).

The present disclosure relates to compositions and methods for cellular immunotherapy by, for example, generating modified antigen-specific T cells for use with MNK-specific inhibition. In particular embodiments, T cells are modified to express an antigen-specific chimeric antigen receptor (CAR) or an antigen-specific T cell receptor (TCR) encoded by a heterologous polynucleotide (transgene), and are modified to inhibit MNK1, MNK2 or both at the gene level, transcriptional level, translational level or both. For example, a modified T cell may express an siRNA that is specific for MNK1, MNK2 or both; or a modified T cell may be edited at the chromosomal level by, for example, mutating (e.g., deleting, truncating, disrupting or the like) a MNK1 gene, a MNK2 gene or both to inhibit (e.g., reduce, knock-out) MNK activity in the T cell. In further embodiments, the present disclosure provides methods for generating or increasing central memory, antigen-specific T cells, improving cytotoxic T lymphocyte (CTL) activity of such T cells, or both by MNK-specific inhibition.

By way of background, the cell-mediated immune response portion of the human adaptive immune system involves activation of lymphocytes (T cells) to mediate destruction of pathogenic or abnormal cells and related molecules. Antigen presenting cells can present a "foreign" antigen that has originated externally (e.g., invading pathogen) or internally from a cell (e.g., cancer cells) to naïve T cells, which then activate, proliferate, and differentiate into effector T cells that migrate to disease sites and exhibit cytotoxic activity towards target cells. Following antigen clearance, most of the effector T cells die due to programmed cell death. However, a small subset of antigen-exposed naïve T cells develop into long-lived memory T cells, e.g., effector memory T cells, located in the disease site, and central memory T cells, located in secondary lymphoid organs. Upon re-exposure to the cognate antigen, memory T cells can rapidly expand and exhibit more effective and faster cytotoxic activity than the primary immune response. Memory T cells generally share the following features: (1) previous expansion and activation; (2) persistence in the absence of antigen; and (3) increased activity upon re-exposure to cognate antigen. Recent studies have demonstrated that the persistence of adoptive (cellular) immunotherapy may depend upon the number of central memory cells in the infused product (see, e.g., Louis et al., *Blood* 118:6050-6056, 2011; Berger et al., *J. Clin. Invest.* 118:294-305, 2008; Sommermeyer et al., *Leukemia* 30:492-500, 2016).

The present disclosure describes the surprising result that MNK-specific inhibition can induce, enhance, or promote expansion of CD4+ central memory T cells, CD8+ central memory T cells, or both, as well as enhance T cell response (e.g., cytotoxic T cell activity). The present disclosure provides modified T cells comprising a transgene encoding an engineered antigen specific receptor that specifically binds to an antigen (e.g., chimeric antigen receptor or TCR), wherein the T cells are contacted with a MNK-specific inhibitor in vivo or ex vivo, or wherein expression of an endogenous gene selected from MNK1, MNK2, or both is inhibited in the modified T cell. Compositions comprising a population of the modified T cells can be used to treat or reduce the progression of a hyperproliferative disease (e.g., cancer), which cells will be capable of, for example, having increased persistence or activity in cellular immunotherapy methods.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, the term "MNK," also known as "mitogen-activated protein kinase (MAPK)-interacting serine/threonine kinase" or "MKNK", refers to a kinase that is phosphorylated by the p42 MAP kinases ERK1 and ERK2 and the p38-MAP kinases, triggered in response to growth factors, phorbol esters, and oncogenes such as Ras and Mos, and by stress signaling molecules and cytokines. MNK also refers to a kinase that is phosphorylated by additional MAP kinase(s) affected by interleukin-1 receptor-associated kinase 2 (IRAK2) and IRAK4, which are protein kinases involved in signaling innate immune responses through toll-like receptors (e.g., TLR7) (see, e.g., Wan et al., *J. Biol. Chem.* 284: 10367, 2009). Phosphorylation of MNK proteins stimulates their kinase activity toward eukaryotic initiation factor 4E (eIF4E), which in turn regulates cap-dependent protein translation initiation, as well as regulate engagement of other effector elements, including hnRNPA1 and PSF (PTB (polypyrimidine tract binding protein) associated splicing factor). For example, proteins that bind the regulatory AU-rich elements (AREs) of the 3'-UTR of certain mRNAs (e.g., cytokines) are phosphorylated by MNK. Thus, MNK phosphorylation of proteins can alter the ability of these proteins to bind the 5'- or 3'-UTRs of eukaryotic mRNAs. In particular, reduced MNK mediated phosphorylation of hnRNPA1 decreases its binding to cytokine-ARE (see, e.g., Buxadé et al., *Immunity* 23:177, 2005; Joshi and Platanias, *Biomol. Concepts* 3:127, 2012). MNK is encoded by two different genes, MNK1 and MNK2, which are both subject to alternative splicing. MNK1a and MNK2a represent full length transcripts, while MNK1b and MNK2b are splice variants that lack a MAPK binding domain. Therefore, MNK may refer to MNK1 or variants thereof (such as MNK1a or MNK1b), MNK2 or variants thereof (such as MNK2a or MNK2b), or combinations thereof. In particular embodiments, MNK refers to human MNK.

The term "inhibit" or "inhibitor" refers to an alteration, interference, reduction, down regulation, blocking, suppression, abrogation or degradation, directly or indirectly, in the expression, amount or activity of a target gene, target protein, or signaling pathway relative to (1) a control, endogenous or reference target or pathway, or (2) the absence of a target or pathway, wherein the alteration, interference, reduction, down regulation, blocking, suppression, abrogation or degradation is statistically, biologically, or clinically significant. The term "inhibit" or "inhibitor"

includes gene "knock out" and gene "knock down" methods, such as by chromosomal editing.

For example, a "MNK inhibitor" may block, inactivate, reduce or minimize MNK activity (e.g., kinase activity or translational effects), or reduce activity by promoting degradation of MNK, by about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more as compared to untreated MNK. In certain embodiments, a MNK inhibitor blocks, inactivates, reduces or minimizes the ability of MNK to phosphorylate eIF4E, hnRNPA1, PSF or combinations thereof. In further embodiments, a MNK inhibitor enhances or promotes expansion of CD4+ central memory T cells, CD8+ central memory T cells, or both. In yet further embodiments, a MNK inhibitor induces or enhances a T cell response. Exemplary inhibitors include small molecules, antisense molecules, ribozymes, inhibitory nucleic acid molecules, endonucleases, or the like.

As used herein, a "MNK-specific inhibitor" is a compound that (a) inhibits MNK enzyme (kinase) activity (i.e., MNK1 and MNK2), (b) has at least about 25-fold less activity against the rest of a host cell kinome as set forth in Table A (i.e., other than MNK enzymes), and (c) does not significantly reduce or inhibit IL-2 production by T cells. As used herein, "a host cell kinome" refers to the 412 protein and lipid kinases listed in Table A (not including the MNK1 and MNK2 enzymes), which may be from a particular organism or cell of interest (e.g., human). The activity of a host cell kinome in the presence and absence of a candidate MNK-specific inhibitor or a known MNK-specific inhibitor (see, e.g., Compound 107 of Table B) is measured using the FRET-based method of Rodems et al. (*Assay. Drug Dev. Technol.* 1:9, 2002).

As used herein, a "internal MNK-specific inhibitor" refers to a MNK-specific inhibitor that is inside or intrinsically produced by a host cell, such as a genetic alteration of an endogenous MNK1 gene, MNK2 gene, or both, such as a gene "knock out" and gene "knock down," that inactivates, reduces or minimize MNK1 activity, MNK2 activity, or both activities without affecting the rest of a host cell kinome; or comprises a polynucleotide that encodes a MNK-specific inhibitor, wherein the host cell self-produces the MNK-specific inhibitor, such as an inhibitory nucleic acid (e.g., siRNA specific for MNK1, MNK2 or both) without affecting the rest of a host cell kinome. In certain embodiments, an internal MNK-specific inhibitor comprises a chromosomally edited MNK1 gene, MNK2 gene, or both, wherein the chromosomal editing results in a deletion, truncation or mutation of the MNK1 gene, MNK2 gene, or both, such that MNK1 activity, MNK2 activity, or both activities are reduced, minimized or inactivated as compared to an unmodified T cell and measured by the level of eIF4E phosphorylation.

In certain embodiments, the host cell kinome of Table A is from a human cell. In further embodiments, a MNK-specific inhibitor is a small molecule and has at least 50-fold less activity against a serine/threonine kinome of an organism or cell as listed in Table A, and does not significantly reduce or inhibit IL-2 production by T cells. In particular embodiments, the serine/threonine kinome of Table A is from a human cell. In still further embodiments, a MNK-specific inhibitor has at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold less, 200-fold less, 250-fold less, 300-fold less, 400-fold less, 500-fold less, 750-fold less, 1000-fold less, or even less activity against kinome enzymes of Table A other than the serine/threonine kinome enzymes of Table A, and does not significantly reduce or inhibit IL-2 production by T cells.

TABLE A

Protein and Lipid Kinases of "Host Cell Kinome" (excluding MNK) Kinome Kinases

| | | | |
|---|---|---|---|
| STK17A (DRAK1) | CAMK2D (CaMKIIδ) | STK4 (MST1) | MATK (HYL) |
| CLK4 | MAP2K1 (MEK1) S218D S222D | ABL2 (Arg) | PAK2 (PAK65) |
| LRRK2 G2019S | KIT T670I | EPHB1 | MAP2K2 (MEK2) |
| LRRK2 R1441C | SNF1LK2 | MAP3K2 (MEKK2) | HIPK1 (Myak) |
| LRRK2 G2019S FL | LATS2 | PDK1 Direct | PRKX |
| FLT3 D835Y | MAPK3 (ERK1) | PRKCQ (PKC theta) | MAP2K6 (MKK6) S207E T211E |
| TGFBR2 | TLK2 | DDR2 T654M | SIK1 |
| PDGFRA V561D | PI4KB (PI4Kβ) | CSNK2A1 (CK2α1) | CDK2/cyclin A1 |
| LRRK2 FL | RAF1 (cRAF) Y340D Y341D | PRKCG (PKCγ) | EPHB3 |
| LRRK2 | MAPK14 (p38α) | EGFR(ErbB1) d746-750 | EIF2AK2 (PKR) |
| BRSK1 (SAD1) | NTRK3 (TRKC) | PRKCI (PKC iota) | SGK (SGK1) |
| STK17B (DRAK2) | EEF2K | RET V804M | GRK5 |
| RIPK2 | RPS6KA5 (MSK1) | AXL | CAMK2B (CaMKIIβ) |
| TNIK | CSF1R (FMS) | PLK1 | ALK C1156Y |
| LRRK2 I2020T | CSNK1D (CK1δ) | CHEK1 (CHK1) | JAK3 |
| KDR (VEGFR2) | ABL1 M351T | STK32C (YANK3) | MYLK (MLCK) |
| PDGFRA D842V | CSNK1G3 (CK1γ3) | HIPK2 | TAOK3 (JIK) |
| KIT D816V | ACVR1 (ALK2) R206H | TEK (TIE2) Y1108F | MAP2K3 (MEK3) |
| KIT A829P | BRAF | MST1R (RON) | WNK3 |
| RET | CDC7/DBF4 | ULK1 | KIT V654A |
| DYRK3 | MAPK13 (p38δ) | PRKCH (PKC eta) | GRK7 |
| DYRK2 | CDC42 BPA (MRCKA) | STK22D (TSSK1) | CSNK1A1 (CK1 α1) |
| RPS6KA6 (RSK4) | KIT N822K | FGFR3 G697C | CDK9 (Inactive) |
| MINK1 | CAMK1D (CaMKIδ) | LIMK1 | EGFR (ErbB1) T790M |

TABLE A-continued

Protein and Lipid Kinases of "Host Cell Kinome" (excluding MNK)
Kinome Kinases

| | | | |
|---|---|---|---|
| MAP3K8 (COT) | MAP2K6 (MKK6) | STK22B (TSSK2) | TEC |
| RET Y791F | PIK3CD/PIK3R1 (p110δ/p85α) | MAP3K10 (MLK2) | MAP4K3 (GLK) |
| BRAF V599E | CLK3 | MAPK10 (JNK3) | MAP3K14 (NIK) |
| RET V804L | EPHA2 | PHKG1 | AMPK (A2/B2/G1) |
| BMPR2 | MAPKAPK3 | NLK | TYK2 |
| PRKG2 (PKG2) | MST4 | KIT | JAK1 |
| MAPK9 (JNK2) | STK25 (YSK1) | BRAF | ACVRL1 (ALK1) |
| KIT D816H | FGFR1 | MAP4K2 (GCK) | MAP4K4 (HGK) |
| PRKD1 (PKC mu) | CSNK1E (CK1ζ) | PIK3CG (p110γ) | DMPK |
| DYRK1A | TYRO3 (RSE) | MET M1250T | MAPK9 (JNK2) |
| CAMK4 (CaMKIV) | FLT3 ITD | CSNK2A2 (CK2α2) | TNK2 (ACK) |
| STK24 (MST3) | PLK2 | TAOK1 | PKN2 (PRK2) |
| PAK7 (KIAA1264) | EPHA7 | ABL1 | PRKG1 |
| AURKC (Aurora C) | CDK1/cyclin B | CDK2/cyclin A2 | LTK (TYK1) |
| ZAP70 | AKT2 (PKBβ) | TEK (TIE2) R849W | CDK7/cyclin H/ MNAT1 |
| MAP2K2 (MEK2) | CDK5/p35 | NUAK1 (ARK5) | ACVR1 (ALK2) |
| PRKCN (PKD3) | SRPK2 | ABL1 G250E | BMPR1A (ALK3) |
| FLT3 | INSR | PAK6 | DDR1 |
| STK39 (STLK3) | MAP2K6 (MKK6) | CDC42 BPB (MRCKB) | ERBB4 (HER4) |
| RET G691S | MARK2 | CDK9/cyclin K | CDK16 (PCTK1)/ cyclin Y |
| AURKB (Aurora B) | CLK1 | CAMK2A (CaMKIIα) | AMPK (A1/B1/G2) |
| GSK3A (GSK3α) | GSG2 (Haspin) | JAK2 JH1 JH2 V617F | MAP2K1 (MEK1) |
| MAPK8 (JNK1) | EPHA4 | CASK | EGFR (ErbB1) L858R |
| SRMS (Srm) | MAPK12 (p38γ) | ACVR2A | PTK6 (Brk) |
| PAK3 | TXK | ALK L1196M | NUAK2 |
| MAPK11 (p38β) | ABL1 Q252H | TTK | STK38L (NDR2) |
| DYRK1B | PASK | DYRK4 | ADRBK2 (GRK3) |
| DNA-PK | GRK4 | WNK2 | MAPK15 (ERK7) |
| IGF1R | FGFR3 | FLT1 (VEGFR1) | ACVR2B |
| PTK2 (FAK) | DAPK2 | PAK1 | MAP3K11 (MLK3) |
| FER | STK23 (MSSK1) | LCK | AXL R499C |
| CSNK1G1 (CK1γ1) | STK3 (MST2) | SRPK1 | PKN1 (PRK1) |
| DDR2 N456S | BRAF V599E | PHKG2 | CDK3/cyclin E1 |
| EPHA5 | AMPK A1/B1/G1 | BMPR1B (ALK6) | MAP4K1 (HPK1) |
| FGFR4 | EGFR (ErbB1) L861Q | BLK | CAMK2G (CaMKIIγ) |
| FGR | AKT1 (PKBα) | MARK4 | MET D1228H |
| SRC | CLK2 | PRKCB1 (PKCβ I) | WEE1 |
| MLCK (MLCK2) | ABL1 T315I | ALK F1174L | ROCK1 |
| MAPK10 (JNK3) | GRK6 | FGFR3 K650E | EPHA3 |
| MAPKAPK2 | EPHA1 | MERTK (cMER) A708S | STK32B (YANK2) |
| PRKD2 (PKD2) | HCK | MAP3K3 (MEKK3) | KIT Y823D |
| FRK (PTK5) | SGK2 | FGFR1 V561M | EGFR (ErbB1) T790M L858R |
| PDGFRA T674I | ULK2 | CDK11 (Inactive) | TAOK2 (TAO1) |
| SRC N1 | CDK5/p25 | MAP3K9 (MLK1) | IKBKE (IKKζ) |
| ROCK2 | KIT D820E | FES (FPS) | NEK9 |
| BMX | MUSK | ITK | MAPK8 (JNK1) |
| CDK2/cyclin O | PRKCA (PKCα) | ZAK | BTK |
| TBK1 | AURKA (Aurora A) | KIT T670E | AMPK (A1/B1/G3) |
| CSK | PRKACA (PKA) | ALK R1275Q | SIK3 |
| CDK1/cyclin A2 | NEK4 | LIMK2 | PIK3C3 (hVPS34) |
| HIPK4 | EPHA6 | ABL1 E255K | PIM1 |
| AMPK A2/B1/G1 | CDK8/cyclin C | MELK | FLT4 (VEGFR3) |
| EPHA8 | JAK2 JH1 JH2 | NEK2 | CDK2/cyclin E1 |
| AKT3 (PKBγ) | ALK | SLK | SPHK1 |
| YES1 | CAMKK1 (CAMKKA) | MERTK (cMER) | PDK1 |
| MARK3 | EPHB2 | MAP2K1 (MEK1) | EGFR (ErbB1) |
| MAPK14 (p38α) Direct | HIPK3 (YAK1) | DDR2 | RET M918T |
| RAF1 (cRAF) Y340D Y341D | FGFR3 K650M | INSRR (IRR) | MAP4K5 (KHS1) |
| IRAK4 | NTRK1 (TRKA) | TEK (Tie2) | FYN A |
| PRKCZ (PKCζ) | STK33 | MARK1 (MARK) | LATS1 |
| RPS6KA1 (RSK1) | CSNK1G2 (CK1γ2) | TLK1 | RPS6KB1 (p70S6K) |
| CAMK1 (CaMK1) | DAPK3 (ZIPK) | AMPK (A1/B2/G1) | PDGFRB (PDGFRβ) |
| PDGFRA (PDGFRα) | ABL1 Y253F | EPHB4 | PRKACG (PRKACγ) |
| RPS6KA2 (RSK3) | ROS1 | ULK3 | PLK3 |
| GSK3B (GSK3β) | MAP3K5 (ASK1) | ABL1 H396P | BRSK2 |
| PAK4 | NEK6 | CDK9/cyclin T1 | TGFBR1 (ALK5) |

TABLE A-continued

Protein and Lipid Kinases of "Host Cell Kinome" (excluding MNK)
Kinome Kinases

| | | | |
|---|---|---|---|
| TESK2 | STK38 (NDR) | SYK | PRKCE (PKCε) |
| NEK1 | IKBKB (IKKβ) | CHEK2 (CHK2) | MAP3K7/MAP3K7I P1 (TAK1-TAB1) |
| DCAMKL2 (DCK2) | PRKACB (PRKACβ) | JAK2 | NEK7 |
| SGKL (SGK3) | MYLK2 (skMLCK) | STK16 (PKL12) | MET (cMet) |
| PIK3C2B (PI3K-C2β) | PRKCB2 (PKCβII) | PLK4 | GRK1 |
| CHUK (IKKα) | PIM2 | ADRBK1 (GRK2) | PIK3CA/PIK3R1 (p110α/p85α) |
| NTRK2 (TRKB) | CAMKK2 (CAMKKβ) | AMPK (A2/B2/G2) | PIK3C2A (PI3K-C2α) |
| ACVR1B (ALK4) | FRAP1 (mTOR) | MAPK1 (ERK2) | SPHK2 |
| RPS6KA3 (RSK2) | ICK | MYO3B (MYO3β) | PI4KA (PI4Kα) |
| PTK2B (FAK2) | LYN A | CDK14 (PFTK1)/cyclin Y | RIPK3 |
| RPS6KA4 (MSK2) | CDK2/cyclin A | DAPK1 | CDK5 (Inactive) |
| FYN | KIT V559D T670I | FGFR2 | IRAK1 |
| LYN B | MAPKAPK5 (PRAK) | ERBB2 (HER2) | PRKCD (PKCδ) |

In any of the aforementioned embodiments, a MNK-specific inhibitor can block, inactivate, reduce or minimize the ability of MNK1a, MNK1b, MNK2a, MNK2b, or any combination thereof to phosphorylate eIF4E, hnRNPA1, PSF or any combination thereof. In particular embodiments, a MNK-specific inhibitor can block, inactivate, reduce or minimize the ability of MNK1a, MNK1b, MNK2a, and MNK2b to phosphorylate eIF4E. MNK-specific inhibitors in any of the aforementioned embodiments may optionally not significantly reduce or inhibit (i) T cell viability, (ii) T cell proliferation, (iii) expression of MHC or HLA molecules in APCs, or (iv) production by T cells of IL-2, CD25, IFNγ, or any combination thereof. Further, optionally, MNK-specific inhibitors in any of the aforementioned embodiments can also significantly reduce or inhibit expression of one or more immunosuppression components (e.g., immune checkpoint molecules, immunosuppressive cytokines) in T cells, APCs or both. The assay for measuring T cell viability is the assay described by Mosmann (*J. Immunol. Meth.* 65:55, 1983).

With regard to a MNK-specific inhibitor, "does not significantly reduce or inhibit IL-2 production by T cells" means the reduction or inhibition of IL-2 production by T cells that is less than about 25%, 20%, 15%, 10%, 5%, 2%, 1%, 0.5%, 0.25%, 0.1% or less as compared to the same T cells not exposed or contacted with the MNK-specific inhibitor.

Also with regard to a MNK-specific inhibitor, "does not significantly reduce or inhibit T cells viability," "does not significantly reduce or inhibit T cell proliferation," "does not significantly reduce or inhibit MHC or HLA molecule expression in T cells, APCs or both," and "does not significantly reduce or inhibit production of IL-2, CD25, IFNγ or any combination thereof by T cells," refers to the reduction or inhibition of T cell viability; T cell proliferation; expression of MHC or HLA molecules in T cells, APCs or both; or production of IL-2, CD25, IFNγ or any combination thereof by T cells; respectively, that is less than about 25%, 20%, 15%, 10%, 5%, 2%, 1%, 0.5%, 0.25%, 0.1% or less as compared to the same corresponding cells not exposed or contacted with the MNK-specific inhibitor.

Also, with regard to a MNK-specific inhibitor, "significantly reduce or inhibit expression of one or more immunosuppression components" means the reduction or inhibition of expression of one or more immunosuppression components in T cells, APCs or both that is at least about 20%, 25%, 30%, 35%, 40%, 45%, 50%, 55%, 60%, 65%, 70% or 75% as compared to the same T cells or APCs not exposed or contacted with the MNK specific inhibitor. In certain embodiments, an APC is a cancer cell or a tumor cell.

Other assays for detecting kinase activity in the presence or absence of inhibitors are well known in the art, which can be used as a back-up to the FRET-based host cell kinome assay to show a particular MNK inhibitor is a MNK-specific inhibitor, such as the assay taught by Karaman et al. (*Nat. Biotechnol.* 26:127, 2007). Assays for detecting the cytokine levels (e.g., IL-2, IL-10, IFNγ) are known in the art, such as the DuoSet® ELISA assay from R&D Systems (using the manufacturer's instructions). Assays for detecting T cell viability, T cell proliferation, MHC or HLA molecule expression, and expression of immunosuppression components like immune checkpoint molecules PD-1, PD-L1, LAG3 or the like are those described in PCT Publication No. WO 2016/172010.

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a T cell (e.g., a CD4+ T cell, a CD8+ T cell, a CD4− CD8− double negative T cell, a γδ T cell, a regulatory T cell ($T_{reg}$), mucosal-associated invariant T cell (MAIT cell)), a B cell, a natural killer cell, a macrophage, a granulocyte, a megakaryocyte, a monocyte, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

As used herein, the term "immune response" refers to the action of an immune cell, for example, lymphocytes, antigen presenting cells, phagocytic cells, granulocytes, and soluble macromolecules produced by the above cells or the liver (including antibodies, cytokines, and complement), that results in selective damage to, destruction of, or elimination from the human body of invading pathogens, cells or tissues infected with pathogens, cancerous cells, or, in cases of autoimmunity or pathological inflammation, normal human cells or tissues. In certain embodiments, an immune response comprises an antigen-specific T cell response.

The phrase "inducing or enhancing a T cell response" refers to causing or stimulating a T cell to have a sustained or amplified biological function. For example, induced or enhanced T cell responses include increased production of cytokines by CD8+ T cells, increased proliferation, increased antigen responsiveness, increased persistence, or increased target cell cytotoxicity relative to the response before intervention. In certain embodiments, the level of enhanced T cell response after contact with a MNK-specific inhibitor is as least about 25%, 30%, 35%, 40%, 45%, 50%, 55%, 60%, 65%, 70%, 75%, 80%, 85%, 90%, 95%, 99%, or more, as compared to immune cells not contacted with the MNK-specific inhibitor. The assay for detecting cytokine levels (e.g., IL-2, IL-10, IFNγ) to determine whether a T cell response induced or enhanced is the multiplex assay described by Dossus et al. (*J. Immunol. Methods* 350:125, 2009). The assay for detecting T cell proliferation to determine whether an immune response induced or enhanced is the assay described by Liu et al. (*Cin. Cancer Res.* 21:1639, 2015). The assay for determining increased antigen responsiveness is the assay described by Tumeh et al. (*Nature* 515:568, 2014). The assay for determining target cell cytotoxicity is the assay described by Tario et al. (*Methods Mol. Biol.* 699:119-164, 2011).

"Major histocompatibility complex" (MHC) refers to glycoproteins that deliver peptide antigens to a cell surface. MHC class I molecules are heterodimers having a membrane spanning a chain (with three α domains) and a non-covalently associated p2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA), which is used herein interchangeably with MHC.

A "T cell" (or "T lymphocyte") is an immune system cell that matures in the thymus and produces T cell receptors (TCRs), which can be obtained (enriched or isolated) from, for example, peripheral blood mononuclear cells (PBMCs) and are referred to herein as "bulk" T cells. After isolation of T cells, T cells can be sorted into cytotoxic (CD8+) and helper (CD4+) T cells, which can be further sorted into naïve, memory, and effector T cell subpopulations, either before or after expansion. T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells ($T_E$) (antigen-experienced, cytotoxic). $T_M$ cells can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). In certain embodiments, a central memory T cell is $CD4^+$, $CD44^{Hi}$, and $CD62L^{Hi}$ T cell or a $CD8^+$, $CD44^{Hi}$, and $CD62L^{Hi}$ T cell. In still further embodiments, T cells comprise memory T stem cells ($T_{MSC}$), which have the following phenotype: $CD44^{Lo}$ $CD45RA^{Hi}$ $CD62L^{Hi}$ $CD95^{Hi}$ $CD122^{Hi}$ sca-$1^+$, and are capable of generating $T_{CM}$ and $T_{EM}$ subsets while maintaining themselves. Effector T cells ($T_E$) refers to antigen-experienced CD8+ cytotoxic T lymphocytes that has decreased expression of CD62L, CCR7, CD28, and are positive for granzyme and perforin as compared to $T_{CM}$. Helper T cells ($T_H$) are CD4+ cells that influence the activity of other immune cells by releasing cytokines. CD4+ T cells can activate and suppress an adaptive immune response, and which action is induced will depend on presence of other cells and signals. T cells also include γδ T cells, MAIT T cells, and $T_{regs}$. T cells can be collected in accordance with known techniques, and the various subpopulations or combinations thereof can be enriched or depleted by known techniques, such as by affinity binding to antibodies, flow cytometry, or immunomagnetic selection. For example, in certain embodiments, CD8+ or CD4+ T cells can be sorted into $CD62L^{Hi}$ (naïve and central memory T cells) or $CD62L^{Lo}$ T cells (effector memory and effector T cells).

"TH1 CD4+T effector cells" or "TH1 helper T cells" refer to CD4+T effector cells that produce pro-inflammatory cytokines, also known as TH1 cytokines. A TH1 cytokine may be IL-2, IFN-γ, TNF-α, TNF-β, GM-CSF, or any combination thereof. TH1 CD4+T effector cells promote cell-mediated immunity.

"TH2 CD4+T effector cells" or "TH2 helper T cells" refer to CD4+T effector cells that produce TH2 cytokines. A TH2 cytokine may be IL-4, IL-5, IL-6, IL-9, IL-10, IL-13, IL-17E (IL-25), or any combination thereof. TH2 CD4+T effector cells promote humoral immunity.

As used herein, an "engineered antigen specific receptor" refers to a protein comprising an extracellular antigen binding domain specific for an antigen, a hydrophobic portion or transmembrane domain, and an intracellular signaling component that is at minimum capable of activating or stimulating a T cell and that is recombinant or genetically modified (e.g., chimeric, fused, mutated, codon optimized, adding/altering expression control elements, etc.). An engineered antigen specific receptor may be composed of a protein monomer, homomultimeric proteins, heteromultimeric proteins, or a protein complex. Examples of an engineered antigen specific receptor include a recombinant polynucleotide encoding a protein version of a naturally-occurring antigen-specific receptor (e.g., codon optimized polynucleotide encoding a TCR), a genetically modified protein (e.g., an enhanced or high affinity TCR), or a fusion protein (e.g., chimeric antigen receptor, TCR-CAR).

As used herein, the term "chimeric antigen receptor" (CAR) refers to a fusion protein engineered to contain two or more naturally-occurring amino acid sequences or portions thereof linked together in a way that does not occur naturally or does not occur naturally in a host cell, which fusion protein can function as a receptor when present on the surface of a cell and comprises an extracellular antigen binding domain specific for an antigen, a hydrophobic portion or transmembrane domain, and an intracellular signaling component that is at minimum capable of activating or stimulating a T cell. An intracellular signaling component may be from a T cell or other receptor (e.g., TNFR superfamily member) or portion thereof, such as an intracellular activation domain (e.g., an immunoreceptor tyrosine-based activation motif (ITAM)-containing T cell activating motif), an intracellular costimulatory domain, or both. A hydrophobic portion or transmembrane domain is disposed between the extracellular antigen binding domain and the intracellular signaling component, which transverses and anchors the CAR in a host cell membrane (e.g., T cell). A chimeric antigen receptor may further comprise an optional extracellular spacer domain connecting the hydrophobic portion or transmembrane domain and the extracellular antigen binding domain.

Exemplary CARs may have two or more portions from the same protein linked in a way not normally found in a cell, or a CAR may have portions from two, three, four, five or more different proteins linked in a way not normally found in a cell. Furthermore, CARs can be in the form of first, second or third generation CARs. For example, a first generation CAR generally may have a single intracellular signaling domain providing an activation signal (e.g., intracellular signaling domain of CD3ζ or FcγRI or other ITAM-containing domain). Second generation CARs further include an intracellular costimulatory domain (e.g., a costimulatory domain from an endogenous T cell costimulatory receptor, such as CD28, 4-1BB, or ICOS). Third generation CARs further include a second costimulatory domain. In some embodiments, compositions of the present disclosure include cells with third-generation CARs, but generally with one set of costimulatory domains on a population enriched for CD4+ or other subpopulation of T cells on the one hand and a different set of costimulatory domains on a population enriched for CD8+ cells or other subpopulation on the other hand.

A CAR can be encoded by a nucleic acid molecule wherein a first nucleotide sequence encoding one protein or portion thereof is appended in frame with a second nucleotide sequence encoding one or more different proteins or a portion thereof, and optionally the first and second nucleotide sequences are separated by nucleotides that encode a linker, spacer or junction amino acid(s) (natural or nonnatural). In certain embodiments, a nucleic acid molecule encoding a CAR is introduced into a host cell and expressed.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease,* 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having a and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_\alpha$, β-chain variable domain or $V_\beta$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

A "TCR-CAR" refers to a heterodimeric fusion protein (see, e.g., Walseng et al., Scientific Reports 7:10713, 2017) comprising an extracellular antigen binding component comprising a soluble TCR (e.g., Vα domain or Vβ domain); a hydrophobic portion or transmembrane domain; and an intracellular signaling component comprising an intracellular activation domain (e.g., ITAM containing T cell activating motif), an intracellular costimulatory domain, or both. An exemplary TCR-CAR comprises a first polypeptide chain comprising a Vα domain, a Cα domain truncated at the transmembrane domain; a second polypeptide chain comprising a Vβ domain, a Cβ domain truncated at the transmembrane domain, a CD8 or CD28 transmembrane domain, a CD28 and/or 4-1BB intracellular costimulatory domain with a CD3ζ intracellular activation domain. The two polypeptide chains of the TCR-CAR are expressed on the cell surface as a heterodimeric protein.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

A cell expressing a high affinity or enhanced affinity TCR specific for an antigen is capable of binding to an antigenic peptide:HLA complex independent or in the absence of CD8, is capable of more efficiently associated with a CD3 protein as compared to endogenous TCR, or both. Methods of generating enhanced affinity TCRs for use in gene therapy are known in the art, and include techniques involving generation of libraries of TCR mutants that have undergone rounds of mutagenesis and subsequent screening for mutations that confer higher affinity for the target peptide/MHC ligand (Richman and Kranz, *Biomol. Eng.* 24:361-373, 2007; Udyavar et al., *J. Immunol.* 182:4439-4447, 2009; Zhao et al., *J. Immunol.* 179:5845-5854, 2007, methods from each of which is incorporated herein by reference in their entirety). Methods of generating enhanced affinity TCRs wherein the TCRα chain from an antigen-specific TCR is used to select de novo generated TCRβ chains that pair with an antigen-specific TCRα chain during T cell development in vitro have also been disclosed (PCT Published Application WO 2013/166321, which methods are incorporated herein by reference in their entirety).

In certain embodiments, a polynucleotide encoding a TCR is codon optimized. In still further embodiments, a single codon optimized polynucleotide encodes a TCR α-chain and a TCR β-chain, wherein the TCR α-chain and the TCR β-chain a separated from each other by a polynucleotide encoding a self-cleaving peptide, such as P2A or T2A. Exemplary self-cleaving polypeptides include a 2A peptide from porcine teschovirus-1 (P2A), equine rhinitis A virus (E2A), *Thosea asigna* virus (T2A), foot-and-mouth disease virus (F2A), or any combination thereof (see, e.g., Kim et al., *PLOS One* 6:e18556, 2011, which 2A nucleic acid and amino acid sequences are incorporated herein by reference in their entirety).

"Antigen" or "Ag" as used herein refers to an immunogenic molecule that provokes a humoral or cellular immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen. Exemplary antigens include tumor antigens, pathogenic microorganism antigens, neurological disease antigens, or autoimmune disease antigens.

The term "epitope" or "antigenic epitope" includes any molecule, structure, amino acid sequence or protein determinant that is recognized and specifically bound by a cognate binding molecule, such as an immunoglobulin, MHC or HLA, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics. For example, a tumor antigen protein or fragment thereof may be an antigen that contains one or more antigenic epitopes.

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., tumor antigen, tumor antigen peptide:MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule (e.g., tumor antigen peptide: HLA or a tetramer such an HLA complex) with an affinity or $K_a$ (i.e., an equilibrium association constant of a particular binding interaction with units of 1/M) equal to or greater than $10^5$ $M^{-1}$ (which equals the ratio of the on-rate $[k_{on}]$ to the off-rate $[k_{off}]$ for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain), wherein the altered domain and wild type or parent domain have at least 85% identity (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" or "polynucleotide" refers to any of deoxyribonucleic acid (DNA), ribonucleic acid (RNA), oligonucleotide, molecules generated, for example, by the polymerase chain reaction (PCR) or by in vitro translation, and molecules generated by any of ligation, scission, endonuclease action, exonuclease action or mechanical action (e.g., sheering). In certain embodiments, nucleic acids of the present disclosure are produced by PCR. Nucleic acids may be composed of a plurality of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties (e.g., morpholino nucleotides). Nucleic acid monomers of the polynucleotides can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, or the like. Nucleic acid molecules can be either single stranded or double stranded.

The term "isolated" means that a material, complex, compound, or molecule is removed from its original environment (e.g., the natural environment if it is naturally occurring). For example, a naturally occurring polynucleotide or polypeptide present in a living animal is not isolated, but the same polynucleotide or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns), if present, between individual coding segments (exons).

As used herein, the term "recombinant" or "genetically engineered" refers to a cell, microorganism, nucleic acid molecule, polypeptide or vector that has been genetically modified by human intervention. For example, a recombinant polynucleotide is modified by human or machine introduction of an exogenous or heterologous nucleic acid molecule, or refers to a cell or microorganism that has been altered by human or machine intervention such that expression of an endogenous nucleic acid molecule or gene is controlled, deregulated or constitutive. Human generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material or encoded products. Exemplary human or machine introduced modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one, two or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp. 71-77, 1975; Lewin, Genes IV, Oxford University Press, NY and Cell Press, Cambridge, Mass., p. 8, 1990).

The term "construct" refers to any polynucleotide that contains a heterologous nucleic acid molecule introduced by a human or a machine. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector, a DNA vector, or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or "transformation" or "transduction" and includes reference to the incorporation of a nucleic acid molecule into a cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, a "transgene" or "heterologous polynucleotide" refers to a nucleic acid molecule, construct, sequence, or portion thereof that is not native to a host cell, but may be homologous to a nucleic acid molecule or portion of a nucleic acid molecule from the host cell. The source of a transgene or heterologous polynucleotide may be from a different genus or species. Alternatively, a transgene or heterologous polynucleotide may be a non-naturally occurring nucleic acid molecule (e.g., a chimeric molecule encoding a fusion protein). In certain embodiments, a host cell is engineered to contain a transgene or heterologous polynucleotide (i.e., is added and is not endogenous or native to the host cell) by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, a "heterologous polynucleotide" introduced into a host cell may encode a non-native enzyme, protein or other activity when that is homologous to an enzyme, protein or other activity encoded by the host cell.

As described herein, more than one transgene or heterologous polynucleotide can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more transgenes or heterologous polynucleotides encoding a desired TCR specific for a tumor antigen peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, the term "host" refers to a cell (e.g., T cell) or microorganism targeted for genetic modification with a transgene or heterologous polynucleotide to produce a polypeptide of interest (e.g., chimeric antigen receptor, high or enhanced affinity TCR, TCR-CAR). In certain embodiments, a host cell may optionally already possess or be modified to include other genetic modifications that confer desired properties related or unrelated to biosynthesis of the transgene, heterologous or exogenous protein (e.g., inhibition, such as a knock out, of MNK1, MNK2 or both genes; inclusion of a detectable marker; deleted, altered or truncated endogenous TCR or HLA; increased co-stimulatory factor expression). A host cell includes progeny of the host cell or the modified host cell, whether genetically or phenotypically the same or different. Suitable host cells may depend on the vector and may include human, non-human primate, cow, horse, sheep, lamb, pig, chicken, turkey, quail, cat, dog, mouse, rat, rabbit or guinea pig cells.

As used herein the term "agent" refers to refers to any molecule, either naturally occurring or synthetic, e.g., peptide, protein, fusion protein, oligopeptide (e.g., from about 5 to about 25 amino acids in length, preferably from about 10 to about 20 or from about 12 to about 18 amino acids in length, preferably 12, 15, or 18 amino acids in length), small organic molecule (e.g., an organic molecule having a molecular weight of less than about 2500 daltons, e.g., less than 2000, less than 1000, or less than 500 daltons), circular peptide, peptidomimetic, antibody, polysaccharide, lipid, fatty acid, inhibitory nucleic acid (e.g., siRNA, miRNA, esiRNA, or shRNA), polynucleotide, oligonucleotide, aptamer, drug compound, or other compound.

An "inhibitory nucleic acid" refers to a short, single stranded or double stranded nucleic acid molecule that has sequence complementary to a target gene or mRNA transcript and is capable of reducing expression of the target gene or mRNA transcript. An inhibitory nucleic acid molecule includes antisense oligonucleotides, double stranded RNA (dsRNA) molecules, siRNA molecules, shRNA molecules, and endoribonuclease-prepared siRNA (esiRNA) molecules. Reduced expression may be accomplished via a variety of processes, including blocking of transcription or translation (e.g., steric hindrance), degradation of the target mRNA transcript, blocking of pre-mRNA splicing sites, blocking mRNA processing (e.g., capping, polyadenylation). In certain embodiments, inhibitory nucleic acid molecules may be used for gene knockdown methods.

An "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for gene "knock-in" to inactivate a target gene. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, and meganucleases.

As used herein, the term "immune suppression component" or "immunosuppression component" refers to one or more cells, proteins, molecules, compounds or complexes providing inhibitory signals to assist in controlling or suppressing an immune response. For example, immunosuppression components include those molecules that partially or totally block immune stimulation; decrease, prevent or delay immune activation; or increase, activate, or up regulate immune suppression. Exemplary immunosuppression component targets include immune checkpoint ligands (such as PD-L1, PD-L2, CD80, CD86, B7-H3, B7-H4, HVEM, adenosine, GAL9, VISTA, CEACAM-1, PVRL2), immune checkpoint receptors (such as PD-1, CTLA-4, BTLA, KIR, LAG3, TIM3, A2aR, CD244/2B4, CD160, TIGIT, LAIR-1, PVRIG/CD112R), metabolic enzymes (such as arginase, indoleamine 2,3-dioxygenase (IDO)), immunosuppressive cytokines (such as IL-10, IL-4, IL-1RA, IL-35), $T_{reg}$ cells, or any combination thereof. In certain embodiments, an immunosuppression component is an immune checkpoint molecule, which may initiate an immune suppression signal through a ligand-receptor interaction, such as by modulating (e.g., inhibiting) an antigen-specific T cell response. For example, a T cell may express on its surface an immune checkpoint receptor (e.g., PD-1, LAG3) and an antigen presenting cell may express on its surface an immune checkpoint receptor ligand (e.g., PD-L1, MHC/HLA molecule). In further embodiments, an immunosuppression component is a metabolic enzyme that inhibits immune responses through the local depletion of amino acids essential for lymphocyte, particularly T cell, survival and function. In still further embodiments, an immunosuppression component may be a signaling molecule, such as an immunosuppressive cytokine (e.g., IL-10, IL-4, IL-1RA, IL-35). In still further embodiments, an immunosuppression component comprises a CD4 $T_{reg}$ cell that is capable of inhibiting an immune response, as well as producing or releasing immunosuppressive cytokines (e.g., IL-10, IL-4, IL-13, IL-1RA).

A "patient" or "subject" includes an animal, such as a human, cow, horse, sheep, lamb, pig, chicken, turkey, quail, cat, dog, mouse, rat, rabbit or guinea pig. The animal can be a mammal, such as a non-primate and a primate (e.g., monkey and human). In one embodiment, a patient is a human, such as a human infant, child, adolescent or adult.

"Effective amount" or "therapeutically effective amount" refers to that amount of a composition described herein which, when administered to a mammal (e.g., human), is sufficient to aid in treating a disease. The amount of a composition that constitutes a "therapeutically effective amount" will vary depending on the cell preparations, the condition and its severity, the manner of administration, and the age of the mammal to be treated, but can be determined routinely by one of ordinary skill in the art having regard to his own knowledge and to this disclosure. When referring to an individual active ingredient or composition, administered alone, a therapeutically effective dose refers to that ingredient or composition alone. When referring to a combination, a therapeutically effective dose refers to combined amounts of the active ingredients, compositions or both that result in the therapeutic effect, whether administered serially, concurrently or simultaneously.

I. Modified T Cells

In certain aspects, the present disclosure provides modified T cells for use as cellular immunotherapy compositions, wherein the modified T cells comprise a transgene encoding an engineered antigen specific receptor that binds to an antigen (e.g., T cell receptor (TCR); chimeric antigen receptor (CAR), TCR-CAR). In certain aspects, a modified T cell further comprises an internal MNK-specific inhibitor. In certain embodiments, an internal MNK-specific inhibitor comprises a chromosomal knock out of a MNK1 gene, MNK2 gene, or both. Internal MNK-specific inhibition (e.g., of MNK1, MNK2, or both) in a modified T cell may induce, enhance, or promote expansion of central memory T cells ($T_{CM}$), such as CD4+$T_{CM}$, CD8+$T_{CM}$, or both, as well as enhance the T cell response to a cognate antigen (e.g., cytotoxic T cell activity).

Prior to genetic modification or expansion of T cells with an engineered antigen specific receptor, internal MNK-specific inhibitor or both, a source of T cells is obtained from a subject (e.g., peripheral blood mononuclear cells, bone marrow, lymph node tissue, cord blood, thymus tissue, tissue from a site of infection, ascites, pleural effusion, spleen tissue), from which T cells are isolated using methods known in the art. Specific T cell subsets can be collected in accordance with known techniques and enriched or depleted by known techniques, such as affinity binding to antibodies, flow cytometry, immunomagnetic selection, or any combination thereof. Following enrichment and/or deletion steps to obtain certain T cells, a transgene encoding an antigen specific receptor and/or an internal MNK-specific inhibitor are introduced into the enriched T cell population to obtain a modified T cell population. The modified T cell population can be expanded in vitro using techniques known in the art, or variations thereof. Genetically engineered (modified) T cells comprising the polynucleotides and inhibitors disclosed herein can be generated ex vivo or in vivo.

As used herein, "enriched" and "depleted" refer to the amount of a T cell subpopulation in a mixture of T cells that was subjected to a process or step that results in an increase in the number of the "enriched" subpopulation, a decrease in the number of the "depleted" subpopulation, or both, as compared to the T cells before being subjected to the process or step of enrichment/depletion. Thus, depending upon the source of the original population of cells subjected to the enriching process, a mixture or composition may contain 30%, 35%, 40%, 45%, 50%, 55%, 60%, 65%, 70%, 75%, 80%, 85%, 90%, 91%, 92%, 93%, 94%, 95%, 96%, 97%, 98%, or 99% or more (in number or count) of the "enriched" cells, which would be an increase as compared to the bulk T cells before treatment. In other words, T cells "enriched" for a particular T cell subpopulation will at the same time result in a "depletion" of other T cell subpopulations not being enriched. T cells subjected to a depleting process can result in a mixture or composition containing 50%, 45%, 40%, 35%, 30%, 25%, 20%, 15%, 10%, 9%, 8%, 7%, 6%, 5%, 4%, 3%, 2%, or 1% percent or less (in number or count) of the "depleted" cells, which would be an decrease as compared to the bulk T cells before treatment. In other words, the act of "depleting" a T cell subpopulation will at the same time result in "enrichment" for a particular T cell subpopulation not being depleted. For example, bulk T cells generally contain about 3% to about 10% central memory T cells ($T_{CM}$), but after selecting for CD62L$^+$CD45RO$^+$ cells using antibodies specific for those markers (i.e., enrichment), the $T_{CM}$ subpopulation may be 50%, 60%, 70, 80% or more of the total T cell population, which means the $T_{CM}$ subpopulation was "enriched" (from about 3%-10% total to about 50%-80% total) while at the same time the CD62L$^-$CD45RA$^-$ subpopulation was "depleted." In certain embodiments, amounts of a certain T cell subpopulation(s) in a mixture will be enriched and amounts of a different T cell subpopulation(s) will be simultaneously depleted. For example, CD4$^+$ T cells may be enriched in a mixture, and CD8$^+$ T cells may simultaneously be depleted. In another example, CD62L$^+$ T cells may be enriched in a mixture, and CD62L$^-$ T cells may be simultaneously depleted. In yet another example, CD4$^+$ and CD62L$^+$ T cells may be enriched in a mixture, and CD8+ and CD62L$^-$ T cells may be simultaneously depleted.

In certain embodiments, a modified T cell comprises a CD4+ T cell or a CD8+ T cell. In further embodiments, modified CD4+ T cells are enriched for naïve CD4+ T cells (CD4+$T_N$), memory stem CD4+ T cells (CD4+$T_{MSC}$), central memory CD4+ T cells (CD4+$T_{CM}$), effector memory CD4+ T cells (CD4+$T_{EM}$), effector CD4+ T cells (CD4+$T_E$), or any combination thereof. In still further embodiments, modified CD8+ T cells are enriched for naïve CD8+ T cells, memory stem CD8+ T cells (CD8+$T_{MSC}$), central memory CD8+ T cells (CD8+$T_{CM}$), effector memory CD8+ T cells (CD8+$T_{EM}$), effector CD8+ T cells ($T_E$), or any combination thereof. In certain embodiments, modified T cells are enriched for CD4+CD62L+ T cells, CD8+CD62L+ T cells, or both.

The present disclosure also provides a population of modified T cells according to any of the embodiments described herein. In some embodiments, a population of genetically modified T cells may comprise the same engineered antigen specific receptor; and, optionally, an internal MNK-specific inhibitor. In other embodiments, a population of genetically modified T cells may comprise two or more subpopulations of T cells, each subpopulation expressing different engineered antigen specific receptors; and, optionally, an internal MNK-specific inhibitor. For example, a population of modified T cells may comprise two or more different subpopulations of T cells each expressing a different engineered antigen specific receptor. In certain embodiments, the two or more different engineered antigen receptors represented in the population of modified T cells may target the same antigen (e.g., the same epitope or different epitopes) or different antigens. In further embodiments, the two or more different engineered antigen receptors may be of the same type of engineered antigen receptor or be different types of engineered antigen receptors. For example, the two or more different engineered antigen receptors may all be CARs, TCRs, or TCR-CARs. In another example, the two or more different engineered antigen receptors may each be independently selected from a CAR, TCR, and TCR-CAR.

In further embodiments, a population of modified T cells may be enriched for particular T cell subpopulations. In certain embodiments, a population of modified T cells is enriched for CD4+ T cells or CD8+ T cells as compared to the bulk T cells from which the enriched CD4+ T cells or CD8+ T cells, respectively, were obtained, wherein the T cells are modified before or after enrichment.

In some embodiments, a population of modified CD4+ T cells is made from (a) a CD45RA$^{Hi}$ CD62L$^{Hi}$ naïve T cell-enriched CD4+ population; (b) a CD45RO$^{Hi}$ CD62L$^{Hi}$ central memory T cell-enriched CD4+ population; (c) a CD62L$^{Hi}$ naïve and central memory T cell-enriched CD4+ population; or (d) a bulk CD4+ T cell population. In some other embodiments, a population of modified T cells is enriched for modified CD4+ T cells, wherein at least 50%, at least about 60%, at least about 70%, at least about 80% or at least about 90% of the modified CD4+ T cells are CD62L$^{Hi}$ or CD62L$^{Hi}$ CD45RO$^{Hi}$.

In some embodiments, a population of modified CD8+ T cells is made from (a) a CD45RA$^{Hi}$ CD62L$^{Hi}$ naïve T cell-enriched CD8+ population; (b) a CD45RO$^{Hi}$ CD62L$^{Hi}$ central memory T cell-enriched CD8+ population; (c) a CD62L$^{Hi}$ naïve and central memory T cell-enriched CD8+ population; or (d) a bulk CD8+ T cell population. In some other embodiments, a population of modified T cells is enriched for modified CD8+ T cells, wherein at least 50%, at least about 60%, at least about 70%, at least about 80% or at least about 90% of the modified CD8+ T cells are CD62L$^{Hi}$ or CD62L$^{Hi}$ CD45RO$^{Hi}$.

In certain aspects, the present disclosure provides modified T cells comprising an engineered antigen specific receptor, wherein the engineered antigen specific receptor comprises a recombinant or genetically modified protein comprising an extracellular antigen binding domain specific for an antigen, a hydrophobic portion or transmembrane domain, and an intracellular signaling component that is at minimum capable of activating or stimulating a T cell; and, optionally, an internal MNK-specific inhibitor. Exemplary engineered antigen specific receptors include recombinant versions of a naturally occurring, exogenous antigen specific receptor (e.g., a recombinant TCR), a genetically modified version of a naturally occurring antigen specific receptor (e.g., a TCR comprising at least one genetic modification such as an enhanced or high affinity TCR), or a fusion protein (e.g., chimeric antigen receptor, TCR-CAR).

In certain embodiments, an engineered antigen specific receptor is an engineered TCR. For example, a modified T cell of this disclosure comprises a transgene encoding a recombinant TCR. In some embodiments, a modified T cell comprises a transgene encoding a TCRα chain and a TCRβ chain. In other embodiments, a modified T cell comprises a transgene encoding a TCRδ chain and a TCRγ chain. Methods of transduction of T cells with a recombinant TCR to redirect T cell specificity in animal and human studies are known in the art (see, e.g., Schmitt et al., *Hum. Gene Ther.* 20:1240-1248, 2009; Abad et al., *J. Immunother.* 31:1-6, 2008; de Witte et al., *J. Immunol.* 181:2563-2571, 2008; Dossett et al., *Mol. Ther.* 17:742-9, 2009; Morgan et al., *Science* 314:126-129, 2006; Robbins et al., *J. Clin. Oncol.* 29:917-24, 2011; Kageyama et al., *Clin. Cancer Res.* 21:2268-2277, 2015; methods from each of which is incorporated by reference in its entirety).

In certain embodiments, an engineered TCR may be a high affinity or enhanced affinity TCR. Methods of generating enhanced affinity TCRs for use in gene therapy are known in the art, and include techniques involving random generation of libraries of TCR mutants that have undergone rounds of mutagenesis or generation of TCR mutants via directed evolution or structure based design, and subsequent screening for mutations that confer higher affinity for the target peptide/MHC ligand (Richman and Kranz, *Biomol. Eng.* 24:361-373, 2007; Udyavar et al., *J. Immunol.* 182: 4439-4447, 2009; Zhao et al., *J. 10 Immunol.* 179:5845-5854, 2007; Robbins et al., *J. Immunol.* 180:6116-6131, 2008; Li et al., *Nat. Biotechnol.* 23:349-54, 2005; Dunn et al., *Protein Sci.* 15:710-721, 2006; Pierce et al., *PLoS Comput. Biol.* 10:e1003478, 2014; Haidar et al., *Proteins* 74:948-960, 2009; Zoete et al., *Front. Immunol.* 4:268, 2013; Harris et al., *J. Biol. Chem.* 291:24566-24578, 2016; methods from each of which is incorporated by reference in its entirety). Methods of generating enhanced affinity TCRs wherein the TCRα chain from an antigen-specific TCR is used to select de novo generated TCRβ chains that pair with an antigen-specific TCRα chain during T cell development in vitro have also been disclosed (PCT Published Application WO 2013/166321, method incorporated herein by reference in its entirety).

In certain embodiments, a modified T cell comprises a transgene encoding an altered TCR, wherein the peptide specificity of the TCR has been changed; and, optionally, an internal MNK-specific inhibitor. Methods of generating TCRs with altered peptide specificity via retroviral TCR display library screening or directed evolution are known in the art (Kessels et al., *Proc. Nat'l. Acad. Sci.* USA 19:14578-83, 2000; Smith et al., *Nat. Commun.* 5:5223, 2014; methods from each of which is incorporated by reference in its entirety).

In certain embodiments, a modified T cell comprises an engineered antigen specific receptor is a chimeric antigen receptor (CAR); and, optionally, an internal MNK-specific inhibitor. A chimeric antigen receptor comprises an extracellular antigen binding domain specific for an antigen, a hydrophobic portion or transmembrane domain, an optional extracellular spacer domain connecting the extracellular antigen binding domain and the hydrophobic portion or transmembrane domain, and an intracellular signaling component that is at minimum capable of activating or stimulating a T cell.

Methods of making CARs are well known in the art and are described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; PCT Publication No. WO2014/134165; and Brentjens et al., 2007, *Clin. Cancer Res.* 13:5426, CAR structures from each of which is hereby incorporated by reference in its entirety. In certain embodiments, a CAR is synthesized as a single polypeptide chain or is encoded by a nucleic acid molecule as a single chain polypeptide. In other embodiments, a CAR is synthesized as at least two polypeptide chains to form a multi-chain CAR (Juillerat et al., *Scientific Reports* 6:18950, 2016; PCT Publication No. WO 2014/039523).

An extracellular antigen binding domain suitable for use in a CAR of the present disclosure can be any antigen binding polypeptide. An antigen binding domain may comprise a natural antibody, synthetic or recombinant antibody construct, or a binding fragment thereof. For example, an antigen binding domain may comprise a full length heavy chain, Fab fragment, Fab', F(ab')$_2$, variable heavy chain domain (VH domain), variable light chain domain (VL domain), domain antibody (dAb), single domain camelid antibody (VHH), complementary determining region (CDR), or single chain variable fragment (scFv). Other examples of antigen binding domains include single chain T cell receptors (scTCRs), extracellular domains of receptors, ligands for cell surface receptors/molecules, tumor binding proteins/peptides, and cytokines. In certain embodiments, an extracellular antigen binding domain is murine, chimeric, human, or humanized.

A CAR extracellular antigen binding domain is optionally followed by an extracellular, non-signaling spacer or linker domain, which, for example, can position the antigen binding domain away from the T cell surface to enable proper cell/cell contact, antigen binding and activation (Patel et al., *Gene Therapy* 6: 412-419, 1999). An extracellular spacer domain of a CAR connects a hydrophobic portion or transmembrane domain and the extracellular antigen binding domain. Spacer domain length may be varied to maximize tumor recognition based on the selected target molecule, selected binding epitope, or antigen binding domain size and affinity (see, e.g., Guest et al., *J. Immunother.* 28:203-11, 2005; PCT Publication No. WO 2014/031687). In certain embodiments, a spacer domain is an immunoglobulin hinge region, an Fc domain or portion thereof, or both, optionally wherein both are human.

A hydrophobic portion or transmembrane domain is disposed between an extracellular antigen binding domain, or the extracellular spacer region if present, and the intracellular signaling component. A transmembrane domain is a hydrophobic alpha helix that transverses a host T cell membrane. In certain embodiments, a transmembrane domain is selected from the same molecule from which the ITAM-containing T cell activating motif is derived (e.g., CD3ζ, FcRγ) or from another type I transmembrane protein, such as CD4, CD8, or CD28.

An intracellular signaling component refers to the portion of a chimeric antigen receptor that can transduce a signal to the inside of the T cell in response to binding of the extracellular binding domain to the target antigen, eliciting an effector function, e.g., activation, cytokine production, proliferation, persistence, cytotoxic activity, homing, entry into the microenvironment of a tumor, or any combination thereof. An intracellular signaling component of a CAR may be linked directly to the carboxyl terminus of the hydrophobic or transmembrane portion or may be separated from the hydrophobic or transmembrane portion by a spacer, linker or one or more junction amino acids.

By way of background, more robust T cell activation generally involves two distinct signaling events: (1) an antigen-specific signal provided through a T cell receptor (TCR) complex, which promotes T cell activation, and (2) a non-antigen specific costimulatory signal provided by the interaction between or the ligation of costimulatory molecules expressed on an antigen presenting cell and a T cell. In some embodiments, a full length intracellular signaling component from, for example, a T cell receptor or other receptor (e.g., TNFR superfamily member), may be used. In further embodiments, a truncated portion of an intracellular signaling component is used, provided that the truncated portion retains sufficient signal transduction activity. In still further embodiments, an intracellular signaling component is a variant of an entire or truncated portion of an intracellular signaling component, provided that the variant retains sufficient signal transduction activity (i.e., is a functional variant).

In certain embodiments, an intracellular signaling component comprises an intracellular activation domain from a receptor, such as an immunoreceptor tyrosine-based activation motif (ITAM)-containing T cell activating motif. An ITAM-containing T cell activating motif used in chimeric antigen receptors of the instant disclosure can be identical to or functional variants of a cytoplasmic signaling domain or portion thereof of an immune cell receptor, or of a cell surface marker containing at least one ITAM. In general, an ITAM-containing T cell activating motif provides a T cell activation signal upon CAR engagement with its target antigen. Non-limiting examples of ITAM containing intracellular activating motifs that may be used in the chimeric antigen receptors described herein include those present on CD3γ, CD3δ, CD3ε, CD3ζ, FcRγ, CD38, CD5, CD22, CD79a, CD79b and CD66d. In particular embodiments, an intracellular signaling component of a CAR of this disclosure comprises a CD3ζ ITAM-containing T cell activating motif.

Examples of intracellular costimulatory domains for use in the CARs of this disclosure include those from CD27, CD28, 4-1BB (CD137), ICOS (CD278), OX40 (CD134), CD30, CD40L, LFA-1, CD2, CD7, LIGHT, NKG2C, GITR, or any combination thereof. In certain embodiments, an intracellular signaling component of a CAR of this disclosure comprises a T cell activating domain or portion thereof (e.g., CD3ζ) and a costimulatory domain or portion thereof (e.g., CD27, CD28, CD134, CD137 or combinations thereof). In certain embodiments, a CAR provided herein comprises a second generation CAR or a third generation CAR. Second generation CARs have one intracellular costimulatory domain combined with an intracellular signaling domain providing an activating signal, while third generation CARs have at least two intracellular costimulatory domains combined with an intracellular signaling domain providing an activating signal.

In certain embodiments, an engineered antigen specific receptor is a TCR-CAR. A TCR-CAR comprises a VαCα polypeptide chain and a VβCβ polypeptide chain, wherein the Cα domain and Cβ domain are truncated at their transmembrane domains, and the VβCβ polypeptide chain is fused to a transmembrane domain, an intracellular activation domain, and optionally an intracellular costimulatory domain. Examples of intracellular activation domains that may be used in TCR-CARs of the present disclosure include those present in include those present on CD3γ, CD3δ, CD3ε, CD3ζ, FcRγ, CD38, CD5, CD22, CD79a, CD79b and CD66d. Examples of intracellular costimulatory domains for use in TCR-CARs of the present disclosure include those present in CD27, CD28, 4-1BB (CD137), ICOS (CD278), OX40 (CD134), CD30, CD40L, LFA-1, CD2, CD7, LIGHT, NKG2C, GITR, or any combination thereof.

In certain embodiments, a CAR is a multimeric fusion protein comprising an extracellular antigen binding component (e.g., a scFv) fused to at least one component of a TCR complex (e.g., CD3γ, CD3ε, or CD3δ), which is capable of assembling with other components of the TCR complex to form a functional, complete TCR fusion complex (see, U.S. Patent Publication No. US 2017/0166622).

In certain embodiments, a modified T cell may comprise one, two or more engineered antigen specific receptors; and, optionally an internal MNK-specific inhibitor. Within a modified T cells comprising two or more engineered antigen specific receptors, each engineered antigen specific receptor may be of the same type of receptor (e.g., two chimeric antigen receptors, two enhanced affinity TCRs) or may be different types of receptors (e.g., one chimeric antigen receptor and one enhanced affinity receptor). In certain embodiments, each engineered antigen specific receptor within a modified T cell comprising two or more engineered antigen specific receptors may target the same antigen or may target different antigens. In further embodiments, two or more engineered antigen specific receptors within a modified T cell that target the same antigen may target different epitopes on the same antigen or may each target the same epitope.

Any number of antigens from tumor cells, cancer cells, pathogenic microorganisms may be targeted by an engineered antigen specific receptor of this disclosure. Examples of such antigens include human immunodeficiency virus (HIV) antigens, hepatitis C virus (HCV) antigens, hepatitis B virus (HBV) antigens, cytomegalovirus (CMV) antigens, Epstein Barr virus (EBV) antigens, parasitic antigens, and tumor antigens, such as ROR1, EGFR, EGFRvIII, HPV E6, HPV E7, L1-CAM, Lewis A, Lewis Y, MUC1, MUC16, PSMA, CD19, CD20, CD22, CD56, CD23, CD24, CD30, CD33, CD37, CD38, CD44v6, CD72, CD79a, CD79b, CD97, CD123, CD171, CD179a, CA125, c-MET, FcRH5, WT1, VEGF-α, VEGFR1, VEGFR2, IL-13Rα2, IL-11Rα, MAGE, MAGE-A1, ephrin A2, ephrin B2, NKG2D ligands, NY-ESO-1, TAG-72, mesothelin, glioma-associated antigen, carcinoembryonic antigen (CEA), IL-13Rα, FAP, B7H3, Kit, CA-IX, CS-1, BCMA, bcr-abl, β-human chorionic gonadotropin, α-fetoprotein (AFP), ALK, cyclin B1, lectin-reactive AFP, Fos-related antigen 1, ADRB3, thyroglobulin, RAGE-1, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, PLAC1, RU1, RU2 (AS), intestinal carboxyl esterase, sLe, LY6K, M-CSF, MYCN, RhoC, TRP-2, CYP1B1, BORIS, prostase, prostate-specific antigen (PSA), PAX3, PAP, LAGE-1a, LMP2, NCAM, p53, p53 mutant, Ras mutant, gp100, prostein, OR51E2, PANX3, PSCA, hTERT, HMWMAA, HAVCR1, survivin, telomerase, legumain, sperm protein 17, SSEA-4, tyrosinase, TARP, ML-IAP, MAD-CT-1, MAD-CT-2, MelanA/MART1, XAGE1, ELF2M, ERG (TMPRSS2 ETS fusion gene), NA17, neutrophil elastase, sarcoma translocation breakpoints, NY-BR- 1, androgen receptor, insulin growth factor (IGF)-I, IGF-II, IGF-I receptor, GD2, o-acetyl-GD2, GD3, GM3, GPRC5D, GPR20, CXORF61, folate receptor alpha (FRα), folate receptor beta, Tie 2, TSHR, UPK2, Tn Ag, FLT3, PRSS21, PDGFR-beta, ERBB2 (Her2/neu), CAIX, TEM1/CD248, TEM7R, CLDN6, polysialic acid, PCTA-1/Galectin 8, mut hsp70-2, LAIR1, FCAR, LILRA2, CD300LF, CLECi2A, BST2, EMR2, LY75, GPC3, FCRL5, IGLL1, psor, and the like. An engineered antigen specific receptor may also target autoimmune disease antigens or neurodegenerative disease antigens.

The present disclosure provides that inhibition of MNK can enhance expansion of central memory CD4+ T cells, central memory CD8+ T cells, or both. Central memory T cells are characterized by proliferative potential and persistence. By way of background, studies indicate that central memory T cells persist longer in vivo following adoptive transfer than effector T cells (Berger et al., *J. Clin. Invest.* 118:249, 2008; Wang et al., *Blood* 117:1888, 2011), underscoring the importance of central memory T cell subsets in cellular immunotherapy. Accordingly, inhibiting expression of endogenous MNK1, MNK2, or both in T cells used for adoptive immunotherapy may enhance the activity and efficacy of cellular immunotherapy.

In further aspects, the present disclosure provides modified T cells comprising a transgene encoding an engineered antigen specific receptor and, optionally an internal MNK-specific inhibitor. An internal MNK-specific inhibitor will inhibit expression of MNK1, MNK2, or both in the modified T cells provided herein, such as by gene knock out or gene knock down, or on a transcriptional level, a translational level, or any combination thereof.

Methods of disrupting or knocking out genes or gene expression in T cells using endonucleases are known in the art and described, for example, in PCT Publication Nos. WO 2015/066262; WO 2013/074916; and WO 2014/059173; methods from each of which are incorporated herein by reference in their entirety. In certain embodiments, expression of an endogenous gene selected from MNK1, MNK2, or both is inhibited or knocked out (e.g., by insertion, deletion, truncation, mutation) with an endonuclease. Exemplary endonucleases useful in chromosome editing include a zinc finger nuclease, a TALE-nuclease, a CRISPR-associated protein 9 nuclease (Cas9), a meganuclease, or combinations thereof.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Nat. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, an internal MNK-specific inhibitor comprises a gene knock out comprising an insertion, a deletion, a mutation or a combination thereof, and made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent $12^{th}$ and $13^{th}$ amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, an internal MNK-specific inhibitor comprises a gene knock out comprising an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337:816-21, 2012). Further, the region of the guide RNA complementary to the target site can be altered or programed to target a desired sequence (Xie et al., PLOS One 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/

071474; which methods for altering gene expression using CRISPR-Cas systems are incorporated herein by reference in their entirety). In certain embodiments, an internal MNK-specific inhibitor comprises a gene knock out comprising an insertion, a deletion, a mutation or a combination thereof, and made using a CRISPR/Cas nuclease system.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG, GIY-YIG, HNH, His-Cys box and PD-(D/E)XK. Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally-occurring meganucleases may be used to promote site-specific genome modification of MNK1, MNK2, or both genes that conserve the meganuclease recognition sequence or to pre-engineered genomes into which a recognition sequence has been introduced. In other embodiments, an engineered meganuclease having a novel binding specificity for MNK1, MNK2, or both is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092).

In further embodiments, an internal MNK-specific inhibitor may reduce, minimize or abrogate MNK1 transcription, post-transcriptional control, post-transcriptional modification, translation, post-translational control, post-translational modification, or any combination thereof. Alternatively, an internal MNK-specific inhibitor may reduce, minimize or abrogate MNK2 transcription, post-transcriptional control, post-transcriptional modification, translation, post-translational control, post-translational modification, or any combination thereof. In further embodiments, an internal MNK-specific inhibitor inhibits expression of MNK1 and MNK2 by reducing, minimizing or abrogating MNK1 and MNK2 transcription, post-transcriptional control, post-transcriptional modification, translation, post-translational control, post-translational modification, or any combination thereof.

In certain embodiments, MNK1, MNK2, or both are knocked down, knocked out, or inhibited at the gene level, transcriptional level, translational level, or both.

In certain embodiments, expression of an endogenous gene selected from MNK1, MNK2, or both is inhibited, or knocked down, with an inhibitory nucleic acid molecule. An inhibitory nucleic acid molecule may inhibit endogenous gene expression at a gene level, transcriptional level, a post-transcriptional level, on a translational level, a post-translational level, or a combination thereof. An inhibitory nucleic acid molecule may be an antisense oligonucleotide (e.g., RNA, DNA, PNA, morpholino, or other chemically modified oligonucleotides), double stranded RNA molecule, siRNA, shRNA, endoribonuclease-prepared siRNA (esiRNA), miRNA, ribozyme.

As used herein, the term "antisense oligonucleotide" refers to short, single-stranded polynucleotide (e.g., 10-50 subunits) made up of DNA, RNA or both, and binds a target RNA transcript. An antisense oligonucleotide may comprise unmodified nucleotides or may contain modified nucleotides, non-natural nucleotides, or analog nucleotides, such as morpholino, phosphorothioate, peptide nucleic acid, LNA, 2'-O-Me RNA, 2'F-RNA, 2'-O-MOE-RNA, 2'F-ANA, or any combination thereof. An antisense oligonucleotide may reduce gene expression by RNAse H-mediated cleavage of the target RNA transcript, by inhibiting translation via steric hindrance of ribosome binding, or by inducing exon-skipping.

As used herein, the terms "siRNA" or "short interfering RNA" refer to a short, double-stranded polynucleotide sequence (e.g., 17-30 subunits) that mediates a process of sequence-specific post-transcriptional gene silencing, translational inhibition, transcriptional inhibition, or epigenetic RNAi in animals (Zamore et al., *Cell* 101:25-33, 2000; Fire et al., *Nature* 391:806, 1998; Hamilton et al., *Science* 286:950-951, 1999; Lin et al., *Nature* 402:128-129, 1999; Sharp, *Genes Dev.* 13:139-141, 1999; and Strauss, *Science* 286:886, 1999).

In certain embodiments, an siRNA comprises a first strand and a second strand that have the same number of nucleosides; however, the first and second strands are offset such that the two terminal nucleosides on the first and second strands are left overhanging. In certain embodiments, the two overhanging nucleosides are thymidine resides. The antisense strand of the siRNA includes a region which is at least partially complementary to the target RNA. In certain embodiments, there is 100% complementarity between the antisense strand of the siRNA and the target RNA. In embodiments where there is partial complementarity of the antisense strand of the siRNA, the complementarity must be sufficient to enable the siRNA, or a cleavage product thereof, to direct sequence specific silencing, such as by RNAi cleavage of the target RNA. In some embodiments, an antisense strand of a siRNA comprises one or more, such as 10, 8, 6, 5, 4, 3, 2 or fewer, mismatches with respect to the target RNA. The mismatches are most tolerated in the terminal regions, and if present are preferably in a terminal region or regions, e.g., within 6, 5, 4, or 3 nucleotides of the 5' or 3' terminus. The sense strand of the siRNA need only be sufficiently complementary to the antisense strand to maintain the overall double-strand character of the molecule RNA-induced silencing complex (RISC).

In certain embodiments, a siRNA may be modified or include nucleoside analogs. Single stranded regions of a siRNA may be modified or include nucleoside analogs, e.g., the unpaired region or regions of a hairpin structure or a region that links two complementary regions. In certain embodiments, a siRNA may be modified to stabilize the 3'-terminus, the 5'-terminus, or both, of the siRNA. For example, modifications can stabilize the siRNA against degradation by exonucleases, or to favor the antisense strand to enter into a RNA-induced silencing complex (RISC). In certain embodiments, each strand of a siRNA can be equal to or less than 30, 25, 24, 23, 22, 21, or 20 nucleotides in length. In further embodiments, each strand is at least 19 nucleotides in length. For example, each strand can be from 21 to 25 nucleotides in length such that the siRNA has a duplex region of at least 17, 18, 19, 29, 21, 22, 23, 24, or 25 nucleotide pairs, and one or more overhangs of 2-3 nucleotides, such as overhangs one or both 3'-ends.

Endoribonuclease-prepared siRNAs (esiRNAs) are siRNAs resulting from cleavage of long double stranded RNA with an endoribonuclease such as RNAse III or dicer. The esiRNA product is a heterogenous mixture of siRNAs that target the same mRNA sequence.

As used herein, the terms "miRNA" or "microRNA" refer to small non-coding RNAs of about 20-22 nucleotides, which is generated from longer RNA hairpin loop precursor structures known as pri-miRNAs. The pri-miRNA undergoes a two-step cleavage process into a microRNA duplex, which is incorporated into RISC. The level of complementarity between the miRNA guide strand and the target RNA determines which silencing mechanism is employed. miRNAs that bind with perfect or extensive complementarity to RNA target sequences, typically in the 3'-UTR, induce cleavage of the target via RNA-mediated interference (RNAi) pathway. miRNAs with limited complementarity to the target RNA, repress target gene expression at the level of translation.

As used herein, the terms "shRNA" or "short hairpin RNA" refer to double-stranded structure formed two complementary (19-22 bp) RNA sequences linked by a short loop (4-11 nt). shRNAs are usually encoded by a vector that is introduced into cells, and the shRNA is processed in the cytosol by Dicer into siRNA duplexes, which are incorporated into the RISC complex, where complementarity between the guide strand and RNA target mediates RNA target specific cleavage and degradation.

As used herein, the term "ribozyme" refers to a catalytically active RNA molecule capable of site-specific cleavage of target mRNA. In certain embodiments, a ribozyme is a Varkud satellite ribozyme, a hairpin ribozyme, a hammerhead ribozyme, or a hepatitis delta ribozyme.

Methods of inhibiting expression of a gene in a T cell using an inhibitory nucleic acid molecule are known in the art and described, for example, in U.S. Patent Publication Nos. US 2012/0321667 and US 2007/0036773; Condomines et al., *PLoS ONE* 10:e0130518, 2015; Ohno et al., *J. Immunother. Cancer* 1:21, 2013).

In certain embodiments, expression of MNK1, MNK2, or both is inhibited using one, two, three, or more internal MNK-specific inhibitors. In certain examples, a single internal MNK-specific inhibitor may be used to target MNK1, MNK2, or both. In another example, a first internal MNK-specific inhibitor may be used to target MNK1, and a second internal MNK-specific inhibitor may be used to target MNK2. In yet another example, a first internal MNK-specific inhibitor may be used to target MNK1, and a second internal MNK-specific inhibitor may be used to target MNK1. In yet another example, a first internal MNK-specific inhibitor may be used to target MNK2, and a second internal MNK-specific inhibitor may be used to target MNK2, and so on.

The modified T cells according to any of the disclosed embodiments may further comprise additional modifications that may increase the efficacy of the cellular immunotherapy, enhance selectivity of transduced T cells, or enhance safety. For example, the genetically modified T cells of the present disclosure may comprise an additional transgene encoding a pro-inflammatory cytokine (e.g., IL-2, IL-12, or IL-15), a co-stimulatory ligand (e.g., 4-1BBL), a transduction marker, a suicide gene, or any combination thereof. In other examples, expression of an endogenous gene, such as TCR gene, HLA gene, an immunosuppression component gene (e.g., an immune checkpoint molecule gene), or any combination thereof is inhibited in the modified T cells of the present disclosure. In certain embodiments, a TCR gene is TRA, TRB, or both. In certain embodiments, a HLA gene is a HLA class I gene, an HLA class II gene, or both. In certain embodiments, an immune checkpoint molecule gene comprises PD-1, CTLA-4, BTLA, KIR, LAG3, TIM3, A2aR, CD244/2B4, CD160, TIGIT, VISTA, PVRIG/CD112R. Expression of a TCR gene, HLA gene, immunosuppression component gene, or any combination thereof may be knocked down, knocked out, or inhibited at the gene level, transcriptional level, translational level, or both. Exemplary inhibitors of expression of a TCR, HLA, or immunosuppression component gene include inhibitory nucleic acid molecules and endonucleases.

According to any of the disclosed embodiments, the present disclosure provides a modified T cell comprising a transgene encoding an engineered antigen specific receptor selected from a chimeric antigen receptor or an antigen-specific TCR, and comprising a chromosomal knock out of a MNK1 gene, MNK2 gene, or both. In another embodiment, the present disclosure provides a modified T cell comprising a chromosomal knock out of a MNK1 gene, MNK2 gene, or both.

The modified T cells used for cellular immunotherapy may be autologous with respect to the subject. Alternatively, the genetically modified T cells may be allogeneic, syngeneic, or xenogeneic with respect to the subject.

II. Polynucleotides, Vectors, and Host Cells

Isolated, recombinant or engineered polynucleotides encoding an engineered antigen specific receptor (e.g., chimeric antigen receptor or enhanced affinity TCR) as described herein may be produced and prepared according to various methods and techniques of the molecular biology or polypeptide purification arts. Construction of an expression vector that is used for recombinantly producing an engineered antigen specific receptor can be accomplished by using any suitable molecular biology engineering techniques known in the art, including the use of restriction endonuclease digestion, ligation, transformation, transfection, plasmid purification, and DNA sequencing as described in, for example, Sambrook et al. (1989 and 2001 editions; *Molecular Cloning: A Laboratory Manual*, Cold Spring Harbor Laboratory Press, NY) and Ausubel et al. (*Current Protocols in Molecular Biology*, 2003). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen.

Certain embodiments relate to polynucleotides that encode the polypeptides contemplated herein, for instance, an engineered antigen specific receptor (e.g., CAR). As one of skill in the art will recognize, a polynucleotide may refer to a single- or a double-stranded DNA, cDNA or RNA in any form, and may include a positive and a negative strand of the polynucleotides which complement each other, including anti-sense DNA, cDNA and RNA. Also included are siRNA, microRNA, RNA-DNA hybrids, ribozymes, and other various naturally occurring or synthetic forms of DNA or RNA.

In certain embodiments, two or more engineered antigen specific receptors according to any of the embodiments disclosed herein are encoded on the same polynucleotide or on separate polynucleotides.

In certain embodiments, an internal MNK-specific inhibitor that inhibits expression of MNK1, MNK2, or both in a T cell is encoded by a polynucleotide that is introduced into the T cell (e.g., shRNA, miRNA, CRISPR/Cas nuclease system, TALEN, ZFN). In certain embodiments, two or more internal MNK-specific inhibitors that inhibit expression of MNK1, MNK2, or both are encoded on the same polynucleotide or on separate polynucleotides that are introduced into the T cell. In certain embodiments, an engineered antigen specific receptor and an internal MNK-specific inhibitor that inhibits expression of MNK1, MNK2, or both in a T cell are encoded on the same polynucleotide or on separate polynucleotides that are introduced into the T cell. In other embodiments, a first polynucleotide encodes a first internal MNK-specific inhibitor comprising an inhibitory nucleic acid molecule specific for MNK1, MNK2 or both, and a second polynucleotide encodes a second internal MNK-specific inhibitor comprising a chromosome editing system specific for MNK1, MNK2 or both selected from a ZFN, a TALEN, a CRISPR/Cas nuclease system, a meganuclease, or combinations thereof, optionally wherein the first and second MNK-specific inhibitors are encoded on the same polynucleotide or on separate polynucleotides for introduction into a T cell. For example, a chromosome editing system may be used to knock out MNK1 (e.g., CRISPR/Cas nuclease system) and MNK2 may be knocked down by introducing a MNK2-specific inhibitory nucleic acid molecule (e.g., MNK2 specific siRNA), or vice-versa, wherein the internal MNK-specific inhibitors are introduced into a modified T cell comprising a heterologous polynucleotide encoding an antigen-specific chimeric antigen receptor (CAR) or an antigen-specific T cell receptor (TCR).

In any of the embodiments disclosed herein, a polynucleotide encoding an engineered antigen specific receptor, an internal MNK-specific inhibitor that inhibits expression of MNK1, MNK2 or both, or any other transgene that is to be introduced into T cells to generate modified T cells of the instant disclosure, may be codon optimized for efficient expression in a target host cell.

Standard techniques may be used for recombinant (i.e., engineered) DNA, peptide and oligonucleotide synthesis, immunoassays and tissue culture, and transformation (e.g., electroporation, lipofection, transfection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir andCC Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II. Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Certain embodiments include polynucleotides of this disclosure contained in a vector. One of skill in the art can readily ascertain suitable vectors for use with certain embodiments disclosed herein. An exemplary vector may comprise a polynucleotide capable of transporting another polynucleotide to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more polynucleotides encoding an engineered antigen specific receptor, encoding an internal MNK-specific inhibitor that inhibits expression of MNK1, MNK2 or both, as described herein, is co-administered to a cell or subject, that each polynucleotide may reside in separate or the same vectors, and multiple vectors (e.g., each containing a different polynucleotide) may be introduced to a T cell or T cell population or administered to a subject.

Suitable viral vectors for use the embodiments disclosed herein include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

A viral vector may also include polynucleotide sequences encoding a marker for transduction. Transduction markers for viral vectors are known in the art and include selection markers, which may confer drug resistance, or detectable markers, such as fluorescent markers or cell surface proteins that can be detected by methods such as flow cytometry. A viral vector may also include a suicide gene. When a viral vector genome comprises a plurality of polynucleotide sequences to be expressed in a host T cell from a single transcript, the viral vector may also comprise additional sequences between each polynucleotide allowing bicistronic or multicistronic expression. Examples of such sequences used in viral vectors include internal ribosome entry sites (RES), furin cleavage sites, viral 2A peptide, or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses. (Jolly, D. J. 1999. *Emerging Viral Vectors*. pp 209-40 in Friedmann T. ed. The Development of Human Gene Therapy. New York: Cold Spring Harbor Lab), or plasmid vectors (such as sleeping beauty or other transposon vectors).

In certain embodiments, the polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides of the instant disclosure are contained in an expression vector that is a viral vector, such as a lentiviral vector or a γ-retroviral vector.

In particular embodiments, the vector is delivered to an appropriate cell, for example, a T cell as described herein. In certain embodiments, a host cell is a human immune system cell. For example, the T cell can be a CD4+ T cell, a CD8+ T cell, a CD4−CD8− double negative T cell, a γδ T cell, or any combination thereof. The T cell can be a naïve, a central memory T cell, a memory stem T cell, an effector memory T cell, an effector T cell, or any combination thereof. In a particular embodiment, the central memory T cell is $CD62L^{Hi}$.

III. Methods of Generating Modified T Cells

In other aspects, the present disclosure provides methods of generating a modified T cell (e.g., a population of T cells) according to any of the embodiments disclosed herein. For example, the methods described herein may be applied to a selected or preferred population of T cells to generate a certain population or subpopulation of modified T cells.

T cells may be collected from a subject from a subject using apheresis methods, such as leukapheresis, which passes the subject's blood through an apparatus, such as a centrifuge, that separates and collects white blood cells from the subject's blood and returns the remaining blood products (e.g., red blood cells, plasma) to circulation in the subject. In certain embodiments, a population of T cells obtained or collected from a subject may be enriched, depleted, or both for particular T cell subpopulation(s) (e.g., T cell subtypes) prior to or after introduction of a transgene encoding an engineered antigen specific receptor into the population of T cells. In some embodiments, a population of T cells is enriched for CD4+ T cells or CD8+ T cells as compared to the bulk T cells from which the enriched CD4+ T cells or CD8+ T cells, respectively, were obtained. In further embodiments, a modified T cell comprises a CD4+ T cell or a CD8+ T cell. In still further embodiments, modified CD4+ T cells are enriched for naïve CD4+ T cells ($CD4+T_N$), memory stem CD4+ T cells ($CD4+T_{MSC}$), central memory CD4+ T cells ($CD4+T_{CM}$), effector memory CD4+ T cells ($CD4+T_{EM}$), or effector CD4+ T cells ($CD4+T_E$), or any combination thereof. In yet further embodiments, modified CD8+ T cells are enriched for naïve CD8+ T cells, memory stem CD8+ T cells ($CD8+T_{MSC}$), central memory CD8+T cells ($CD8+T_{CM}$), effector memory CD8+ T cells ($CD8+T_{EM}$), or effector CD8+ T cells ($T_E$), or any combination thereof. In certain embodiments, modified T cells are enriched for CD4+CD62L+ T cells, CD8+CD62L+ T cells, or both. In any of the aforementioned embodiments of enriched/or depleted T cells, the T cells may be modified with a transgene encoding an engineered antigen specific receptor before or after the enrichment/or depletion step(s).

In particular embodiments, a population of modified CD4+ T cells is comprised of: (a) a $CD45RA^{Hi}$ $CD62L^{Hi}$ naïve T cell-enriched CD4+ population; (b) a $CD45RO^{Hi}$ $CD62L^{Hi}$ central memory T cell-enriched CD4+ population; (c) a $CD62L^{Hi}$ naïve and central memory T cell-enriched CD4+ population; or (d) a bulk CD4+ T cell population. In some embodiments, a population of modified T cells is enriched for modified CD4+ T cells, wherein at least 50%, at least about 60%, at least about 70%, at least about 80% or at least about 90% of the modified $CD4^+$ T cells are $CD62L^{Hi}$ or $CD62L^{Hi}$ $CD45RO^{Hi}$.

In particular embodiments, a population of modified CD8+ T cells is comprised of: (a) a $CD45RA^{Hi}$ $CD62L^{Hi}$ naïve T cell-enriched CD8+ population; (b) a $CD45RO^{Hi}$ CD62L$^{Hi}$ central memory T cell-enriched CD8+ population; (c) a CD62L$^{Hi}$ naïve and central memory T cell-enriched CD8+ population; or (d) a bulk CD8+ T cell population. In some other embodiments, a population of modified T cells is enriched for modified CD8+ T cells, wherein at least 50%, at least about 60%, at least about 70%, at least about 80% or at least about 90% of the modified CD8+ T cells are CD62L$^{Hi}$ or CD62L$^{Hi}$ CD45RO$^{Hi}$.

The T cells may be obtained from an animal, such as a human, cow, horse, sheep, lamb, pig, chicken, turkey, quail, cat, dog, mouse, rat, rabbit or guinea pig. In a preferred embodiment, the animal is a mammal, such as a non-primate or a primate (e.g., monkey and human). In a particular embodiment, the T cells are a human.

A T cell may be obtained from a healthy subject (e.g., for storage for later therapeutic use) or a subject having a disease associated with expression of an antigen. A T cell may also be obtained from a subject that is a healthy donor and not the recipient of the adoptively transferred modified T cells (e.g., for allogeneic transfer to a subject).

In certain aspects, the present disclosure provides methods for generating a modified T cell comprising introducing a transgene encoding an engineered antigen specific receptor into any of the aforementioned T cells, T cell populations, or T cell subpopulations obtained from a subject. In some embodiments, a method for generating a modified T cell population of this disclosure further comprises contacting a population or subpopulation of T cells obtained from a subject as described herein with a MNK-specific inhibitor. The contacting step with the MNK-specific inhibitor may occur simultaneously, concurrently, or sequentially with the introduction of the transgene encoding the engineered antigen specific receptor into the population or subpopulation of T cells, thereby generating the population or subpopulation of modified T cells. In certain embodiments, the MNK-specific inhibitor is administered to the population or subpopulation of T cells before or after introduction of the transgene encoding the engineered antigen specific receptor into the population or subpopulation of T cells.

In certain embodiments, a method of generating a modified T cell of this disclosure comprises first contacting a population or subpopulation of T cells as described herein with a MNK-specific inhibitor in an amount and for a time sufficient to promote an increase in CD4+ central memory T cells, an increase in CD8+ central memory T cells, an increase in a T cell response (e.g., cytotoxic T cell activity), or any combination thereof, as compared to a population of T cells from the subject that were not contacted with the MNK-specific inhibitor; and second introducing a transgene encoding an engineered antigen specific receptor (e.g., CAR or TCR) into the MNK-specific inhibitor-treated T cells, thereby generating the modified T cells for use in, for example, adoptive immunotherapy. In certain embodiments, the MNK-specific inhibitor is contacted with the population or subpopulation of T cells for at least about 1 day, about 2 days, about 3 days, about 4 days, about 5 days, about 6 days, or about 7 days.

In certain other embodiments, a method of generating a modified T cell of this disclosure comprises first introducing a transgene encoding an engineered antigen specific receptor (e.g., CAR or TCR) into a population or subpopulation of T cells as described herein; and second contacting with a MNK-specific inhibitor in an amount and for a time sufficient to promote an increase in CD4+ central memory T cells, an increase in CD8+ central memory T cells, an increase in a T cell response (e.g., cytotoxic T cell activity), or any combination thereof, thereby generating the modified T cells for use in, for example, adoptive immunotherapy. In certain embodiments, the MNK-specific inhibitor is contacted with the population or subpopulation of T cells for at least about 1 day, about 2 days, about 3 days, about 4 days, about 5 days, about 6 days, or about 7 days.

An engineered antigen specific receptor may be according to any of the embodiments described herein. In certain embodiments, the engineered antigen specific receptor is a chimeric antigen receptor (CAR), an engineered TCR (e.g., recombinant TCR, enhanced affinity TCR), a TCR-CAR, or any combination thereof. Transgenes encoding an engineered antigen specific receptor may be introduced into the T cell by a DNA vector, an RNA vector, a plasmid, a lentiviral vector, an adenovirus vector, or a retroviral vector, as described herein.

Exemplary MNK-specific inhibitors for use in any of the embodiments described herein include any compound described herein or found in Table B. In certain embodiments, a MNK-specific inhibitor used in the methods for generating a modified T cell of this disclosure is a compound having the following formula:

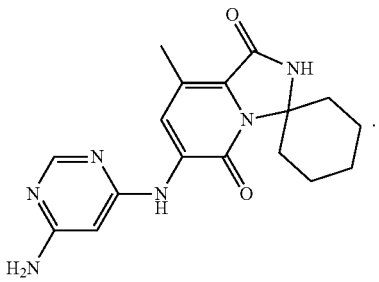 [SMILES: Cc1cc(Nc2cc(N)ncn2)c(=O)n2c1C(=O)NC21CCCCC1]

In any of these embodiments, the contacting step and introduction step are performed ex vivo on T cells obtained from the subject or obtained from a donor. In certain embodiments, a T cell population is contacted with a MNK-specific inhibitor continuously ex vivo. In further embodiments, ex vivo generated modified T cells of this disclosure are used in adoptive immunotherapy of the subject, wherein the adoptive immunotherapy comprises autologous, allogeneic or syngeneic modified T cells.

In other aspects, the present disclosure provides methods for generating a modified T cell comprising introducing a transgene encoding an engineered antigen specific receptor into a T cell collected from a subject who had been administered or treated with a MNK-specific inhibitor, thereby generating the modified T cell from a subject previously administered or treated with a MNK-specific inhibitor. In some embodiments, a MNK-specific inhibitor causes an increase in CD4+ central memory T cells, an increase in CD8+ central memory T cells, an increase in T cell response (e.g., cytotoxic T cell activity), or any combination thereof in the population of T cells obtained from the subject, as compared to a population of T cells obtained from the subject before having been administered or treated with the MNK-specific inhibitor. A MNK-specific inhibitor may be according to any of the embodiments described herein. In particular embodiments, a MNK-specific inhibitor is any compound found in Table B or is a compound according to the formula:

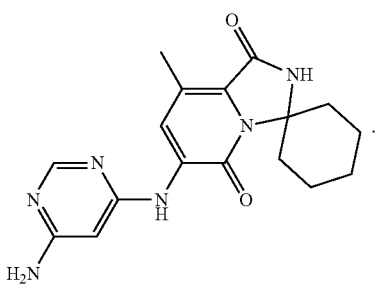

In further embodiments, a T cell is collected from a subject having been administered or treated with a MNK-specific inhibitor after a sufficient time, after a sufficient dosing with the MNK-specific inhibitor, or both, such that the level of CD4+ central memory T cells, the level of CD8+ central memory T cells, the level of cytotoxic T cell activity, or any combination thereof is increased in a population of T cells collected from the subject as compared to the level of central memory T cells collected from the subject prior to administration of the MNK-specific inhibitor. For example, the subject may be administered or treated with the MNK-specific inhibitor starting at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days prior to collection of T cells from the subject.

In some embodiments involving an autologous transfer of a modified T cell, a subject is administered or treated with a MNK-specific inhibitor and continues to be administered or treated with the MNK-specific inhibitor following collection of the T cells from the subject. In still further embodiments, the subject is administered an autologous, genetically modified population of T cells according to this disclosure and continues to receive the MNK-specific inhibitor following administration of the autologous, genetically modified population of T cells.

In some embodiments, the T cell collected from a MNK-specific inhibitor treated subject is also contacted with the MNK-specific inhibitor ex vivo simultaneously, concurrently, sequentially with the introduction of the transgene encoding the engineered antigen specific receptor. In further embodiments, the T cell is contacted with the MNK-specific inhibitor continuously during the ex vivo stage.

It is contemplated that the methods of generating modified T cells and adoptive immunotherapy treatment methods of the present disclosure encompass any combination of ex vivo and in vivo MNK-specific inhibitor treatment regimens disclosed herein. Thus, a subject may be treated with a MNK-specific inhibitor prior to collection of T cells from the subject; following collection of the T cells from the subject, the T cells may be contacted with a MNK-specific inhibitor simultaneously, concurrently, or sequentially with the introduction of a transgene encoding an engineered antigen specific receptor; the subject may be treated with a MNK-specific inhibitor simultaneously, concurrently, or sequentially with adoptive transfer of the population or subpopulation of modified T cells to the subject; or any combination thereof. For example, T cells collected from a subject may be genetically modified with a transgene encoding an engineered antigen specific receptor, treated ex vivo with a MNK-specific inhibitor, and transferred back to the subject. In another example, T cells collected from a subject may be genetically modified with a transgene encoding an engineered antigen specific receptor, treated ex vivo with a MNK-specific inhibitor, transferred back to the subject, and the MNK-specific inhibitor is administered to the subject simultaneously, concurrently, or sequentially with the adoptive transfer of the modified T cells. In still another example, T cells collected from a subject may be genetically modified with a transgene encoding an engineered antigen specific receptor, transferred back to the subject, and the MNK-specific inhibitor is administered to the subject simultaneously, concurrently, or sequentially with the adoptive transfer of the modified T cells.

In any of the aforementioned embodiments, the method of generating a modified T cell further comprises introducing an internal MNK-specific inhibitor (e.g., chromosomal editing endonuclease, inhibitory nucleic acid) into the T cell obtained from a subject, wherein expression of endogenous MNK1, MNK2, or both is inhibited or knocked out in the T cell. An internal MNK-specific inhibitor may be introduced into the T cell simultaneously, concurrently, sequentially with the transgene encoding the engineered antigen specific receptor.

In some embodiments, a MNK-specific inhibitor is administered to the subject simultaneously, concurrently, sequentially with the genetically modified T cell.

In another aspect, the method comprises introducing a transgene encoding an engineered antigen specific receptor that binds to an antigen into a T cell, and an internal MNK-specific inhibitor, wherein MNK-specific inhibitor inhibits expression of an endogenous gene selected from MNK1, MNK2, or both, thereby generating the modified T cell. In some embodiments, the internal MNK-specific inhibitor is an endonuclease or an inhibitory nucleic acid.

Expression of endogenous MNK1, MNK2, or both may be inhibited in a T cell according to any of the embodiments described herein. In certain embodiments, MNK1, MNK2, or both may be knocked out, knocked down, or inhibited at the gene level, transcriptional level, translational level, or both. For example, expression of MNK1 is knocked down or inhibited in a T cell by a first internal MNK-specific inhibitor, while MNK2 is knocked out in the T cell by a second internal MNK-specific inhibitor. Alternatively, expression of MNK2 is knocked down or inhibited in a T cell by a first internal MNK-specific inhibitor, while MNK1 is knocked out in the T cell by a second internal MNK-specific inhibitor. In other embodiments, expression of MNK1 and MNK2 are knocked down or inhibited in a T cell by an internal MNK-specific inhibitor (e.g., siRNA), expression of MNK1 and MNK2 are knocked down or inhibited in a T cell by a MNK-specific inhibitor (e.g., Compound 107 of Table B), or expression of MNK1 and MNK2 are knocked out in the T cell by an internal MNK-specific inhibitor (e.g., by gene editing). In certain embodiments, expression of MNK1, MNK2, or both are inhibited by a MNK-specific inhibitor, by an internal MNK-specific inhibitor, or both. In some embodiments, an internal MNK-specific inhibitor may be an inhibitory nucleic acid, including an antisense oligonucleotide, a dsRNA molecule, an siRNA molecule, an esiRNA, or an shRNA molecule. In some other embodiments, a MNK-specific inhibitor may be any compound disclosed herein, including those listed in Table B. In other embodiments, an internal MNK-specific inhibitor may be an endonuclease, including a CRISPR/Cas nuclease system, a zinc finger nuclease, a TALE nuclease, or a meganuclease.

Prior to, simultaneously, concurrently, or after introduction of a transgene encoding an engineered antigen specific receptor, a T cell may be modified to increase the efficacy of the cellular immunotherapy, enhance selectivity of transduced T cells, or enhance safety. For example, the T cells may comprise an additional transgene encoding a pro-inflammatory cytokine (e.g., IL-2, IL-12, or IL-15), a costimulatory ligand (e.g., 4-1BBL), a transduction marker, a suicide gene, or any combination thereof. In other examples, expression of an endogenous gene, such as TCR gene, HLA gene, an immunosuppression component gene (e.g., an immune checkpoint molecule gene), or any combination thereof is inhibited in the T cells. In certain embodiments, the TCR gene is TRA, TRB, or both. In certain embodiments, the HLA gene is a HLA class I gene, an HLA class II gene, or both. In certain embodiments, an immune checkpoint molecule gene comprises PD-1, CTLA-4, BTLA, KIR, LAG3, TIM3, A2aR, CD244/2B4, CD160, TIGIT, VISTA, PVRIG/CD112R, or any combination thereof. Expression of a TCR gene, HLA gene, immunosuppression component gene, or any combination thereof may be knocked down, knocked out, or inhibited at the gene level, transcriptional level, translational level, or both. Exemplary inhibitors of expression of a TCR, HLA, or immunosuppression component genes include inhibitory nucleic acid molecules and endonucleases.

IV. Pharmaceutical Compositions

In another aspect, the present disclosure provides a pharmaceutical composition comprising a modified T cell of the present disclosure, e.g., a population of modified T cells, in combination with one or more pharmaceutically or physiologically acceptable carriers, diluents, or excipients. Such compositions may comprise water, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

In certain embodiments, the pharmaceutical composition is substantially free of, or lacking detectable levels of a contaminant, such as endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium, a fungus, or any combination thereof. In some embodiments, the bacterium is at least one of: *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

Pharmaceutical compositions including compositions of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration.

The pharmaceutical compositions of the present disclosure may be administered in any convenient manner, including by aerosol inhalation, injection, ingestion, transfusion, implantation or transplantation. The compositions described herein may be administered to a subject trans-arterially, subcutaneously, intradermally, intratumorally, intranodally, intramedullary, intramuscularly, intravenously (i.v.), or intraperitoneally. In certain embodiments, a pharmaceutical composition of the present disclosure is administered by i.v. injection. The pharmaceutical compositions may be injected directly into a tumor, lymph node, cerebrospinal fluid, or the site of infection or disease.

In certain embodiments, pharmaceutical compositions comprising a modified T cell of the present disclosure, e.g., a population of modified T cells, further comprise a MNK-specific inhibitor, as described herein.

V. Methods of Use

The present disclosure also provides methods of cellular immunotherapy or for treating a subject having, for example, a cancer, an autoimmune disease, or a pathogen infection, comprising administering to the subject an effective amount of a modified T cell, a population of modified T cells, or a pharmaceutical composition thereof according to any of the embodiments described herein.

Subjects that can be treated by the present disclosure include animals, such as a human, cow, horse, sheep, lamb, pig, chicken, turkey, quail, cat, dog, mouse, rat, rabbit or guinea pig. In certain embodiments, a subject is human and other primate subjects, such as monkeys and apes. The subjects can be male or female and can be any suitable age, including infant, juvenile, adolescent, adult, and geriatric subjects.

A treatment effective amount of modified T cells in a composition is at least one cell (for example, one CAR modified CD8+ T cell subpopulation; one CAR modified CD4+ T cell subpopulation; or both), or is more typically greater than $10^2$ cells, for example, at least $10^6$, at least $10^7$, at least $10^8$ cells, at least $10^9$ cells or more than $10^{10}$ cells. In certain embodiments, modified T cells of this disclosure are administered in a range from about $10^6$ to about $10^{10}$ cells/m$^2$, preferably in a range of about $10^7$ to about $10^9$ cells/m$^2$. The number of cells will depend upon the ultimate use for which the composition is intended as well the type of cells included therein. For example, cells modified to contain a CAR specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than $10^7$ cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$ or $10^{11}$ cells.

Disorders amenable to cellular immunotherapy or treatment using the compositions and methods described herein include hyperproliferative disorders. As used herein, "hyperproliferative disorder" or "hyperproliferative disease" refers to excessive growth or proliferation as compared to a normal cell or an undiseased cell. Exemplary hyperproliferative disorders include dysplasia, neoplasia, non-contact inhibited or oncogenically transformed cells, tumors, cancers, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, or the like). In certain embodiments, a cancer being treated by the compositions and methods of this disclosure includes carcinoma (epithelial), sarcoma (connective tissue), lymphoma or leukemia (hematopoietic cells), germ cell tumor (pluripotent cells), blastoma (immature "precursor" cells or embryonic tissue), or any combination thereof. These various forms of hyperproliferative disease are known in the art and have established criteria for diagnosis and classification (e.g., Hanahan and Weinberg, *Cell* 144:646, 2011; Hanahan and Weinberg *Cell* 100:57, 2000; Cavallo et al., *Canc. Immunol. Immunother.* 60:319, 2011; Kyrigideis et al., *J. Carcinog.* 9:3, 2010).

A wide variety of hyperproliferative disorders, including solid tumors and leukemias, are amenable to the compositions and methods disclosed herein. Exemplary cancers that may be treated include adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional representative cancers that may be treated include histiocytic disorders; histiocytosis malignant; immunoproliferative small intestinal disease; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; and trophoblastic tumor.

Exemplary hematological malignancies include acute lymphoblastic leukemia (ALL), acute myeloid leukemia (AML), chronic myelogenous leukemia (CML), chronic eosinophilic leukemia (CEL), myelodysplastic syndrome (MDS), Hodgkin's lymphoma, non-Hodgkin's lymphoma (NHL) (e.g., follicular lymphoma, diffuse large B-cell lymphoma, or chronic lymphocytic leukemia), or multiple myeloma (MM).

Still further exemplary hyperproliferative disorders include adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; sertoli cell tumor; thecoma; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Other disorders that may be treated by the compositions and methods disclosed herein include infections by pathogenic microorganisms, including viruses (e.g., HIV, BK polyomavirus, adenovirus, hepatitis C virus (HCV), hepatitis B virus (HBV), cytomegalovirus (CMV), Epstein-Barr virus (EBV), bacteria, and parasites; autoimmune diseases (e.g., systemic lupus erythematosus, diabetes, rheumatoid arthritis, reactive arthritis, multiple sclerosis, pemphigus vulgaris, celiac disease, Crohn's disease, inflammatory bowel disease, ulcerative colitis, autoimmune thyroid disease); inflammatory disorders; and neurodegenerative diseases (e.g., Alzheimer's disease).

In certain embodiments, a cancer that may be treated by the compositions and methods disclosed herein is solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof.

VI. Combination Therapies

As used herein, a "combination" refers to a combination comprising a modified T cell (e.g., a population of modified T cells) according to the embodiments described herein plus at least one additional therapeutic agent, each of which may be administered serially (sequentially), concurrently or simultaneously, as described herein. In certain embodiments, a subject may be treated with a population of genetically modified T cells comprising a transgene encoding an engineered antigen specific receptor (e.g., an antigen-specific CAR or an antigen-specific TCR), an internal MNK specific inhibitor, a MNK-specific inhibitor, an inhibitor of an immunosuppression component (e.g., an immune checkpoint molecule), a chemotherapeutic agent, radiotherapy, surgery or any combination thereof.

In certain embodiments, an additional therapeutic agent that is an inhibitor of an immunosuppression component is an inhibitor of an immune checkpoint molecule or gene, a metabolic enzyme, an immunosuppressive cytokine, $T_{reg}$ cells, or any combination thereof. Immune checkpoint molecules include immune checkpoint ligands such as, PD-L1, PD-L2, CD80, CD86, B7-H3, B7-H4, HVEM, adenosine, GAL9, VISTA, CEACAM-1, CEACAM-3, CEACAM-5, PVRL2, and immune checkpoint receptors such as, PD-1, CTLA-4, BTLA, KIR, LAG3, TIM3, A2aR, CD244/2B4, CD160, TIGIT, LAIR-1, and PVRIG/CD112R). Metabolic enzymes include arginase and indoleamine 2,3-dioxygenase (IDO)), and immunosuppressive cytokines include IL-10, IL-4, IL-1RA, and IL-35. In certain embodiments, an inhibitor of immunosuppression component is a siRNA molecule or an antibody. An antibody specific for PD-1 may be pidilizumab, nivolumab, or pembrolizumab. An antibody specific for PD-L1 may be MDX-1105 (BMS-936559), durvalumab (formerly MEDI4736), atezolizumab (formerly MPDL3280A), or avelumab (formerly MSB0010718C). An antibody specific for CTLA4 may be tremelimumab or ipilimumab.

In certain embodiments, an additional therapeutic agent is a chemotherapeutic agent. An anti-cancer agent may be a B-Raf inhibitor, a MEK inhibitor, a VEGF inhibitor, a VEGFR inhibitor, a tyrosine kinase inhibitor, or a cytotoxic agent. Other anti-cancer agents include an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. In certain embodiments, an anti-cancer agent is vemurafenib, dabrafenib, trametinib, cobimetinib, sunitinib, erlotinib, paclitaxel, docetaxel, or any combination thereof.

In certain embodiments, a subject may be treated with a population of genetically modified T cells comprising a transgene encoding an engineered antigen specific receptor (e.g., an antigen-specific CAR or an antigen-specific TCR) and an optional internal MNK-specific inhibitor, in combination with a MNK-specific inhibitor, e.g., any one of the MNK-specific inhibitors of Formula I, Ia, IIa, IIb, IIIa, IIIb, IVa, IVb, Va, Vb, VI, VIIa or VIIb or Table B. The MNK-specific inhibitor may be administered to the subject prior to administration of the population of genetically modified T cells to the subject. For example, the subject may be treated with a MNK-specific inhibitor prior to collection of a population of T cells from the subject (for autologous T cells) or a donor may be treated with a MNK-specific inhibitor prior to collection of a population of T cells from the donor (for allogeneic T cells). In certain embodiments, the subject is treated with the MNK-specific inhibitor for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 days prior to collection of the T cells from the subject. In another example, the subject may be treated with a MNK-specific inhibitor after collection of the T cells from the subject but prior to adoptive transfer. In certain embodiments, the subject is treated with the MNK-specific inhibitor for about 1, about 2, about 3, about 4, about 5, about 6, about 7, about 8 about 9, or about 10 days following collection of the T cells but prior to adoptive transfer. In addition or alternative to the pre-collection or pre-adoptive transfer treatment of the subject with a MNK-specific inhibitor, the subject may be treated with the MNK-specific inhibitor simultaneously, concurrently, or after administration of the population of genetically modified T cells to the subject (for either autologous or allogeneic transfer of modified T cells). In certain embodiments, the subject is treated with the MNK-specific inhibitor for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 days after administration of the population of genetically modified T cells to the subject.

In certain aspects, MNK-specific inhibitors that are potent and selective inhibitors of MNK1 and MNK2 may be used in the pharmaceutical compositions and methods of use described herein. MNK-specific inhibitors include compounds of Formula I, Ia, IIa, IIb, IIIa, IIIb, IVa, IVb, Va, Vb, VI, VIIa or VIIb, including Compound 107 (see, e.g., PCT Publication WO 2016/172010, which compounds and synthetic methods are incorporated herein by reference in their entirety). By way of background, MNK1 and MNK2 integrate signals from several oncogenic and immune signaling pathways by phosphorylating eukaryotic initiation factor 4E (eIF4E) and other mRNA binding proteins, which regulate the stability and translation of select mRNAs important for tumor growth and survival.

Administration of a MNK-specific inhibitor to a subject in combination with the modified T cells disclosed herein may further enhance expansion of central memory T cells, enhance cytotoxic T cell activity, or both.

Exemplary MNK-specific inhibitors inhibit both MNK1 and MNK2 kinase activity. In certain embodiments, a MNK-specific inhibitor selectively inhibits MNK1 kinase activity over MNK2 kinase activity, or selectively inhibits MNK2 kinase activity over MNK1 kinase activity. In other embodiments, a MNK-specific inhibitor selectively inhibits kinase activity of full length isoforms MNK1a and MNK2a over the kinase activity of MNK1b and MNK2b. In further embodiments, a MNK-specific inhibitor selectively inhibits either MNK1 kinase activity or MNK2 kinase activity. In still further embodiments, a MNK-specific inhibitor selectively inhibits kinase activity of any one of full length isoforms MNK1a, MNK1b, MNK2a, or MNK2b, or inhibits the kinase activity of all the MNK isoforms.

In certain embodiments, a MNK-specific inhibitor is a compound according the following structure (I):

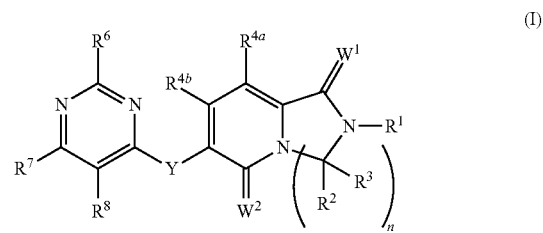

or a stereoisomer, tautomer or pharmaceutically acceptable salt thereof wherein:

$W^1$ and $W^2$ are independently O, S or N—OR', where R' is lower alkyl;

Y is —N($R^5$)—, —O—, —S—, —C(O)—, —S=O, —S(O)$_2$—, or —CHR$^9$—;

$R^1$ is hydrogen, lower alkyl, cycloalkyl or heterocyclyl wherein any lower alkyl, cycloalkyl or heterocyclyl is optionally substituted with 1, 2 or 3 J groups;

n is 1, 2 or 3;

$R^2$ and $R^3$ are each independently hydrogen, alkyl, alkenyl, alkynyl, aryl, araalkylene, heteroaryl, heteroarylalkylene, cycloalkyl, cycloalkylalkylene, heterocyclyl, or heterocyclylalkylene, wherein any alkyl, aryl, araalkylene, heteroaryl, heteroarylalkylene, cycloalkyl, cycloalkylalkylene, heterocyclyl, or heterocyclylalkylene, is optionally substituted with 1, 2 or 3 J groups;

or $R^2$ and $R^3$ taken together with the carbon atom to which they are attached form a cycloalkyl or heterocyclyl, wherein any cycloalkyl or heterocyclyl is optionally substituted with 1, 2 or 3 J groups;

$R^{4a}$ and $R^{4b}$ are each independently hydrogen, halogen, hydroxyl, thiol, hydroxyalkylene, cyano, alkyl, alkoxy, acyl, thioalkyl, alkenyl, alkynyl, cycloalkyl, aryl, or heterocyclyl;

$R^5$ is hydrogen, cyano, or lower alkyl;

or $R^5$ and $R^8$ taken together with the atoms to which they are attached form a fused heterocyclyl optionally substituted with 1, 2 or 3 J groups;

$R^6$, $R^7$ and $R^8$ are each independently hydrogen, hydroxy, halogen, cyano, amino, alkyl, alkenyl, alkynyl, alkoxy, cycloalkyl, cycloalkylalkylene, cycloalkylalkenylene, alkylaminyl, alkylcarbonylaminyl, cycloalkylcarbonylaminyl, cycloalkylaminyl, heterocyclylaminyl, heteroaryl, or heterocyclyl, and wherein any amino, alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups;

or $R^7$ and $R^8$ taken together with the atoms to which they are attached form a fused heterocyclyl or heteroaryl optionally substituted with 1, 2 or 3 J groups;

J is —SH, —$SR^9$, —S(O)$R^9$, —S(O)$_2R^9$, —S(O)NH$_2$, —S(O)N$R^9R^9$, —NH$_2$, —N$R^9R^9$, —COOH, —C(O)O$R^9$, —C(O)$R^9$, —C(O)—NH$_2$, —C(O)—N$R^9R^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, N$R^9R^9$—C(O)-alkylene, —CH$R^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$R^9$—C(O)-cycloalkyl, —C(O)-cycloalkyl, —CH$R^9$—C(O)-aryl, —CH$R^9$-aryl, —C(O)-aryl, —CH$R^9$—C(O)-heterocycloalkyl, —C(O)-heterocycloalkyl, heterocyclylaminyl, or heterocyclyl; or any two J groups bound to the same carbon or hetero atom may be taken together to form oxo; and $R^9$ is hydrogen, lower alkyl or —OH.

In one embodiment of structure (I), the present disclosure provides a compound having the following structure (Ia), as well as stereoisomers, tautomers or pharmaceutically acceptable salts thereof.

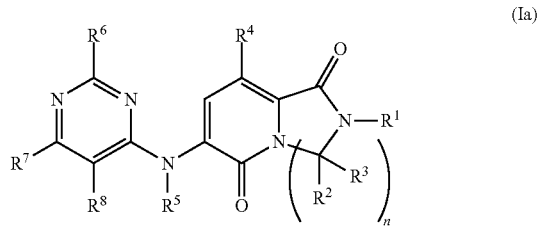

(Ia)

For Formula Ia compounds, substituent R is hydrogen or lower alkyl and subscript n is 1, 2 or 3. Substituents $R^2$ and $R^3$ in Formula Ia are each independently hydrogen, alkyl, cycloalkyl, cycloalkylalkylene, heterocyclyl or heterocyclylalkyl, and any such alkyl, cycloalkyl, cycloalkylalkylene, heterocyclyl or heterocyclylalkyl can optionally be substituted with 1, 2 or 3 J groups.

Substitutents $R^2$ and $R^3$ in Formula Ia when taken together with the carbon atom to which they are attached can form a cycloalkyl or heterocyclyl, wherein any such cycloalkyl or heterocyclyl is optionally substituted with 1, 2 or 3 J groups. In Formula Ia, $R^{4a}$ is hydrogen, halogen, hydroxy, alkyl, alkoxy, thioalkyl, alkenyl or cycloalkyl and substituent $R^5$ is hydrogen or lower alkyl.

Alternatively, substituent groups $R^5$ and $R^8$ taken together with the atoms to which they are attached form a fused heterocyclyl that is optionally substituted with 1, 2 or 3 J groups.

In one embodiment, substituents $R^6$, $R^7$ and $R^8$ are independently and at each occurrence hydrogen, halogen, alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl, and any such alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl is optionally substituted with 1, 2 or 3 J groups. For some compounds in accordance with Formula Ia, $R^7$ and $R^8$ taken together with the atoms to which they are attached form a fused heterocyclyl unsubstituted or substituted with 1, 2 or 3 J groups.

Variable J in Formula Ia is —SH, —$SR^9$, —S(O) $R^9$, —S(O)$_2R^9$, —S(O)NH$_2$, —S(O)N$R^9R^9$, —NH$_2$, —N$R^9R^9$, —COOH, —C(O)O$R^9$, —C(O)$R^9$, —C(O)— NH$_2$, —C(O)—N$R^9R^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, N$R^9R^9$—C(O)-alkylene, —CH$R^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$R^9$—C(O)-cycloalkyl, —C(O)-cycloalkyl, —CH$R^9$—C(O)-aryl, —CH$R^9$-aryl, —C(O)-aryl, —CH$R^9$—C(O)-heterocycloalkyl, —C(O)-heterocycloalkyl, heterocyclylaminyl, or heterocyclyl. For some of the inventive compounds according to Formula Ia, any two J groups bound to the same carbon or hetero atom may be taken together to form an oxo group.

In some embodiments, variable J in Formula Ia is halogen, amino, alkyl, haloalkyl, alkylaminyl, cycloalkyl or heterocyclyl. Alternatively, for certain Formula Ia compounds, any two J groups when bound to the same carbon or hetero atom may be taken together to form oxo group.

Further MNK-specific inhibitors are compounds according to Formula IIa, illustrated below, where variable Y is —N($R^5$)— and subscript "n" is 1.

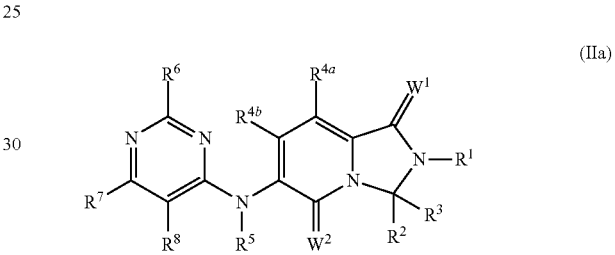

(IIa)

According to one embodiment, variable Y in Formula I is —O—, —S—, —C(O)—, sulfoxide, sulfone, —CH$R^9$— or —CH$_2$—, subscript "n" is 1 and the inventive compounds conform to Formula IIb. When "Y" is —CH$R^9$— in Formula IIb, substituent $R^9$ is hydrogen, lower alkyl or hydroxy.

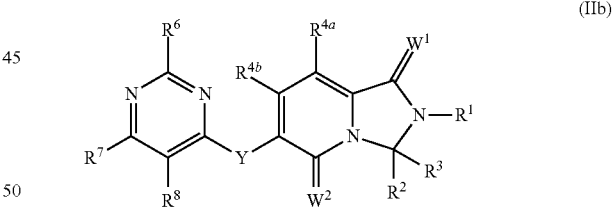

(IIb)

In more MNK-specific inhibitor embodiments, variable "Y" in Formula I is —N($R^5$)—, subscript "n" is 2 or 3 and the compounds conform to Formula IIIa or Formula IVa, respectively:

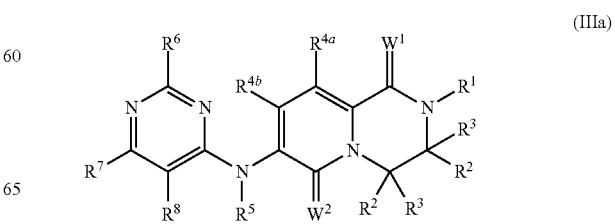

(IIIa)

-continued

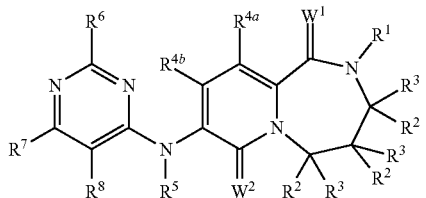
(IVa)

Alternatively, in certain embodiments, variable "Y" in Formula I is —O—, —S—, —C(O)—, sulfoxide, sulfone, —CHR$^9$— or —CH$_2$—, "n" is 2 or 3 and the compounds conform to Formula IIIb and Formula IVb, respectively: When "Y" is —CHR$^9$— in Formula IIIb or Formula IVb, substituent R$^9$ is either hydrogen, lower alkyl or hydroxy.

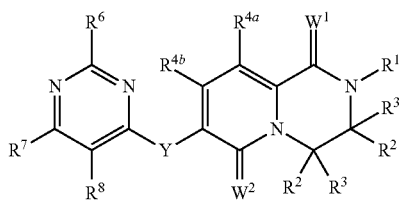
(IIIb)

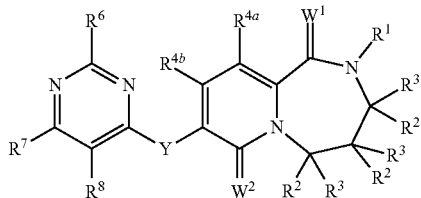
(IVb)

For MNK-specific inhibitors according to Formulae IIa, IIb, IIIa, IIIb, IVa and IVb, variables W$^1$ and W$^2$ are both oxo. In certain embodiments for compounds according to Formulae IIa, IIb, IIIa, IIIb, IVa and IVb, W$^1$ is oxo and W$^2$ is thione group. According to one embodiment, Formulae IIa, IIb, IIIa, IIIb, IVa and IVb compounds comprise an oxo at W$^1$ and a=N—OR' group at W$^2$. Also encompassed within the scope of the present MNK-specific inhibitors are Formulae IIa, IIb, IIIa, IIIb, IVa and IVb compounds having a thione group at W$^1$ and an oxo group at W$^2$.

For Formulae IIa, IIb, IIIa, IIIb, IVa and IVb compounds, each of substituents R$^2$ and R$^3$ can be the same in which case the carbon atom which R$^2$ and R$^3$ are attached is not a chiral carbon. In certain embodiments, however, substituents R$^2$ and R$^3$ are different. Thus, the carbon atom to which R$^2$ and R$^3$ are attached is chiral and the resulting compound will have stereoisomers.

In certain MNK-specific inhibitor embodiments, each R$^2$ and R$^3$ in Formulae IIa, IIb, IIIa, IIIb, IVa and IVb is hydrogen. Alternatively, one of R$^2$ or R$^3$ groups in Formulae IIa, IIb, IIIa, IIIb, IVa and IVb is hydrogen and the other group is alkyl optionally substituted with 1, 2 or 3 J groups. For certain compounds according to Formulae IIa, IIb, IIIa, IIIb, IVa and IVb, R$^2$ and R$^3$ are both alkyl groups that are optionally substituted with 1, 2 or 3 J groups.

For some compounds in accordance with Formula IIa or Formula IIb, R$^2$ is alkyl and R$^3$ is alkyl substituted with 1, 2 or 3 J groups. Exemplary of this category of Formula IIa and Formula IIb compounds are the following: compounds with substituent R$^2$ as alkyl and R$^3$ is haloalkyl; compounds with substituent compounds with substituent R$^2$ as alkyl and R$^3$ is cycloalkyl optionally substituted with 1, 2 or 3 J groups; compounds with substituent R$^2$ as alkyl and R$^3$ is cyclopentyl optionally substituted with 1, 2 or 3 J groups; compounds with substituent R$^2$ as alkyl and R$^3$ is aryl optionally substituted with 1, 2 or 3 J groups; compounds with substituent R$^2$ as alkyl and R$^3$ is phenyl optionally substituted with 1, 2 or 3 J groups; compounds with substituent R$^2$ as alkyl and R$^3$ is cycloalkylalkylene optionally substituted with 1, 2 or 3 J groups; compounds with substituent R$^2$ as alkyl and R$^3$ is aralkylene optionally substituted with 1, 2 or 3 J groups; compounds with substituent R$^2$ as alkyl and R$^3$ is benzyl optionally substituted with 1, 2 or 3 J groups; compounds with substituent R$^2$ as alkyl and R$^3$ is heterocyclyl optionally substituted with 1, 2 or 3 J groups; compounds with substituent R$^2$ as alkyl and R$^3$ is heteroaryl optionally substituted with 1, 2 or 3 J groups; compounds with substituent R$^2$ as alkyl and R$^3$ is thiophenyl, thiazolyl or pyridinyl; compounds with substituent R$^2$ as alkyl and R$^3$ is heterocyclylalkylene substituted or substituted with 1, 2 or 3 J groups; or compounds with substituent R$^2$ as alkyl and R$^3$ is heteroarylalkylene optionally substituted with 1, 2 or 3 J groups.

In some embodiments, for compounds according to Formulae IIa, IIb, IIIa, IIIb, IVa and IVb, each R$^2$ and R$^3$ are independently hydrogen, alkyl, cycloalkyl, cycloalkylalkylene, heterocyclyl or heterocyclylalkylene, and any such alkyl, cycloalkyl, cycloalkylalkylene, heterocyclyl or heterocyclylalkylene can optionally be substituted with 1, 2 or 3 J groups, independently selected from the group consisting of halogen, amino, alkylaminyl and alkyl.

For certain Formulae IIIa, IIIb, IVa and IVb compounds, R$^2$ and R$^3$ together with the carbon atom to which they are attached form a cycloalkyl or heterocyclyl ring.

Also contemplated are Formula I compounds where Y is —N(R$^5$)—, subscript "n" is 1 and R$^2$ and R$^3$ together with the carbon atom to which they are attached form a cycloalkyl or heterocyclyl ring "A." Such compounds conform to Formula Va and the cycloalkyl or heterocyclyl ring "A" may optionally be substituted with 1, 2 or 3 J groups.

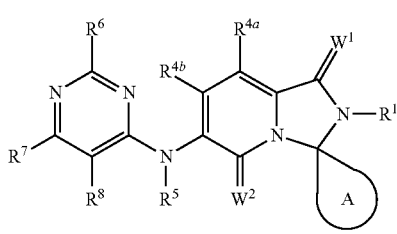
(Va)

Alternatively, in some embodiments Y in Formula I is —O—, —S—, —C(O)—, sulfoxide, sulfone, —CHR$^9$— or —CH$_2$—, "n" is 1 and R$^2$ and R$^3$ together with the carbon atom to which they are attached form a cycloalkyl or heterocyclyl ring A. Such compounds conform to Formula Vb and the cycloalkyl or heterocyclyl ring "A" may optionally be substituted with 1, 2 or 3 J groups. When "Y" is —CHR$^9$— in Formula Vb, substituent R$^9$ is either hydrogen, lower alkyl or hydroxy.

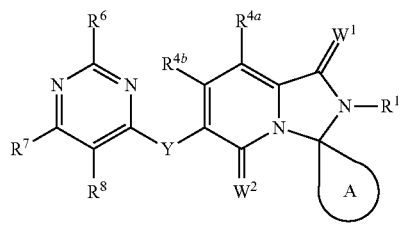

(Vb)

For Formula Va and Formula Vb compounds, $W^1$ and $W^2$ are both oxo and ring A is a cycloalkyl optionally substituted with 1, 2 or 3 J groups. Also contemplated are Formula Va and Formula Vb compounds for which ring A is a fused cycloalkyl optionally substituted with 1, 2 or 3 J groups; ring A is a cycloalkyl optionally substituted with 1, 2 or 3 J groups; ring A is a cyclobutyl, cyclopentyl or cyclohexyl optionally substituted with 1, 2 or 3 J groups, for example, J groups selected from the group consisting of halogen, amino, alkylaminyl and alkyl.

For some embodiments, ring A of a Formula Va or a Formula Vb is a heterocyclyl optionally substituted with 1, 2 or 3 J groups. Exemplary of such heterocyclyl groups are pyrrolidinyl, piperidinyl, tetrahydropyranyl, thietanyl or azetidinyl. In one embodiment, each of the above exemplified heterocyclyl may optionally be substituted with 1, 2 or 3 J groups. For certain Formula Va or a Formula Vb compounds ring A is a cycloalkyl substituted with at least 2J groups attached to the same carbon atom of the cycloalkyl, and the two J groups attached to the same carbon taken together form oxo group. In another embodiment, ring A of a Formula Va or a Formula Vb is a heterocyclyl substituted with at least 2J groups that are attached to the same hetero atom and wherein such 2 J groups taken together to form oxo. For some Formula Va or a Formula Vb compounds the cycloalkyl or heterocyclyl ring A is substituted with J groups selected from the group consisting of halogen, cyano, hydroxy, trifluoromethyl, N-methyl amino, methyl, difluoroethylene, and methylenenitrile.

The present disclosure also provides compounds in accordance with Formula VI or its stereoisomers, tautomers or pharmaceutically acceptable salts. Formula VI is a subgenus of Formula I in which Y is —N($R^5$)— and substituent groups $R^5$ and $R^8$ together with the atoms to which they are attached form a heterocycle ring B which may optionally be substituted with 1, 2 or 3 J groups.

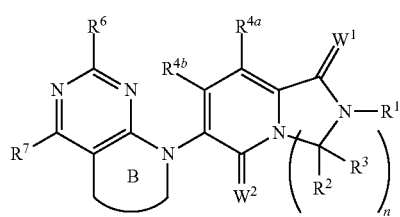

(VI)

Also encompassed within the scope of the present MNK-specific inhibitors are Formula I compounds in which variable "Y" is —N($R^5$)—, and substituent groups $R^7$ and $R^8$ together with the atoms to which they are attached form a fused ring C. Such compounds or the stereoisomer, tautomer or pharmaceutically acceptable salt conform to Formula VIIa. For Formula VIIa compounds, ring C may optionally be substituted with 1, 2 or 3 J groups.

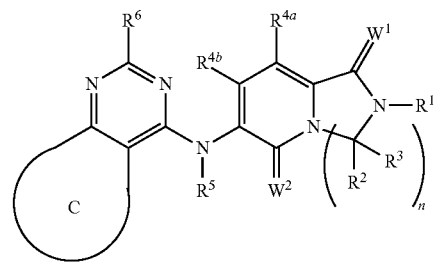

(VIIa)

According to one embodiment, variable "Y" in Formula I is —O—, —S—, —C(O)—, sulfoxide, sulfone, —CHR$^9$— or —CH$_2$—, and substituent groups $R^7$ and $R^8$ together with the atoms to which they are attached form a fused ring C. Such compounds and their stereoisomers, tautomers or pharmaceutically acceptable salts conform to Formula VIIb. For Formula VIIb compounds where "Y" is —CHR$^9$—, substituent $R^9$ can be hydrogen, lower alkyl or hydroxy.

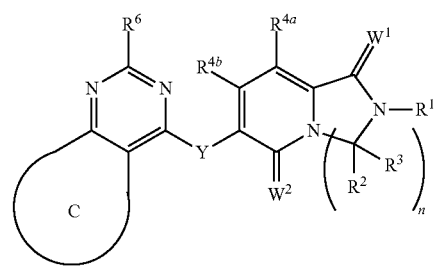

(VIIb)

For Formula VIIb compounds, fused ring C may optionally be substituted with 1, 2 or 3 J groups. In one MNK-specific inhibitor embodiment, $W^1$ and $W^2$ are both oxo for Formula VI, Formula VIIa and Formula VIIb compounds.

MNK-specific inhibitors of this disclosure are further directed to Formulae I, Ia, IIa, IIb, IIIa, IIIb, IVa, IVb, Va, Vb, VI, VIIa and VIIb compounds where $R^1$ is hydrogen or a lower alkyl group selected from methyl, ethyl, propyl, butyl, iso-propyl, sec-butyl, or tert-butyl, for example, compounds with $R^1$ as methyl.

For certain Formulae I, Ia, IIa, IIb, IIIa, IIIb, IVa, IVb, Va, Vb, VI, VIIa and VIIb compounds, $R^{4a}$ is selected from the group consisting of hydrogen, halogen, alkyl, alkoxy, thioalkyl, alkenyl, and cycloalkyl while substituent $R^{4b}$ is hydrogen or halogen. $R^5$ in Formulae I, Ia, IIa, IIb, IIIa, IIIb, IVa, IVb, Va, Vb, VI, VIIa and VIIb is hydrogen or lower alkyl, while substituents $R^6$, $R^7$ and $R^8$ are hydrogen.

In certain embodiments of this disclosure, $R^6$ and $R^7$ in Formula VI are both hydrogen, while for certain Formula VIIa and Formula VIIb compounds $R^6$ is hydrogen.

MNK-specific inhibitors of this disclosure are further directed to Formulae I, Ia, IIa, IIb, IIIa, IIIb, IVa, IVb, Va, and Vb compounds where substituent groups $R^6$ and $R^8$ are both hydrogen, and $R_7$ is selected from the group consisting of hydroxy, halogen, cyano, alkyl, alkenyl, alkynyl, alkoxy, cycloalkyl cycloalkylalkylene, cycloalkylenylene, amino, alkylaminyl, alkylcarbonylaminyl, cycloalkylcarbonylaminyl, cycloalkylaminyl, heterocyclylaminyl, heteroaryl, and heterocyclyl. For these compounds, any alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups. In certain embodiments, $R_7$ is selected from the group consisting of alkyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl and cycloalkylaminyl. For such compounds any alkyl, alkenyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl or cycloalkylaminyl may optionally be substituted with 1, 2 or 3 J groups. Thus, certain embodiments provide Formulae I, Ia, IIa, IIb, IIIa, IIIb, IVa, IVb, Va, and Vb compounds where substituent groups $R^6$ and $R^8$ are both hydrogen, and $R_7$ is amino; substituent groups $R^6$ and $R^8$ are both hydrogen, and $R_7$ is alkylaminyl; substituent groups $R^6$ and $R^8$ are both hydrogen, and $R_7$ is —NHCH$_3$; substituent groups $R^6$ and $R^8$ are both hydrogen, and $R_7$ is cycloalkyl, for example cyclopropyl; substituent groups $R^6$ and $R^8$ are both hydrogen, and $R_7$ is cycloalkylaminyl substituted with 1 to 3 J groups, for instance halogens.

In one embodiment, for compounds in accordance with Formulae I, Ia, IIa, IIb, IIIa, IIIb, IVa, IVb, Va, and Vb, substituent groups $R^6$ and $R^8$ are both hydrogen, and $R_7$ is selected from the group consisting of —NHCH(CF$_3$)cyclopropyl, cycloalkylcarbonylaminyl, —NHC(O)cyclopropyl, cycloalkylalkenylene, and —CH═CHcyclopropyl.

For any compound in accordance with Formulae I, Ia, IIa, IIb, IIIa, IIIb, IVa, IVb, Va, Vb, VI, VIIa, and VIIb, J is —SH, —SR$^9$, —S(O)R$^9$, —S(O)$_2$R$^9$, —S(O)NH$_2$, —S(O)NR$^9$R$^9$, —NH$_2$, —NR$^9$R$^9$, —COOH, —C(O)OR$^9$, —C(O)R$^9$, —C(O)—NH$_2$, —C(O)—NR$^9$R$^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, NR$^9$R$^9$—C(O)-alkylene, —CHR$^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CHR$^9$—C(O)-cycloalkyl, —C(O)-cycloalkyl, —CHR$^9$—C(O)-aryl, —CHR$^9$-aryl, —C(O)-aryl, —CHR$^9$—C(O)-heterocycloalkyl, —C(O)-heterocycloalkyl, heterocyclylaminyl, or heterocyclyl and R$^9$ is hydrogen, lower alkyl or —OH. Additionally, when two J groups bound to the same carbon or hetero atom they may be taken together to form oxo.

For certain compounds according to Formulae I, Ia, IIa, IIb, IIIa, IIIb, IVa, IVb, Va, Vb, VI, VIIa, and VIIb, J is halogen, hydroxy, alkyl, alkenyl, alkynyl or cyanoalkylene. Illustrative alkyl or alkylene chains are those having $C_1$-$C_{10}$ carbon atoms, $C_1$-$C_8$ carbon atoms, $C_1$-$C_6$ carbon atoms, $C_1$-$C_4$ carbon atoms, $C_1$-$C_3$ carbon atoms as well as ethyl and methyl groups. Alternatively, when J is alkenyl, or alkynyl, the carbon chain has at least one double or triple bond respectively and $C_2$-$C_{10}$ carbon atoms, $C_2$-$C_8$ carbon atoms, $C_2$-$C_6$ carbon atoms, $C_2$-$C_4$ carbon atoms, or $C_2$-$C_3$ carbon atoms.

A MNK-specific inhibitor of Formula (I), as well as Formulae Ia, IIa, IIb, IIIa, IIIb, IVa, IVb, Va, Vb, VI, VIIa and VIIb, may be isotopically-labelled by having one or more atoms replaced by an atom having a different atomic mass or mass number. Examples of isotopes that can be incorporated into the compounds of structure (I) include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. These radiolabelled compounds may be useful to help determine or measure the effectiveness of the compounds, by characterizing, for example, the site or mode of action, or binding affinity to pharmacologically important site of action. Certain isotopically-labelled compounds of Formula (I), for example, those incorporating a radioactive isotope, are useful in drug or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I), as well as Formulae Ia, IIa, IIb, IIIa, IIIb, IVa, IVb, Va, Vb, VI, VIIa and VIIb, can generally be prepared by conventional techniques known to those skilled in the art or by processes analogous to those described in the Preparations and Examples as set out in U.S. patent application Ser. No. 14/748,990 filed Jun. 24, 2015 and entitled "MNK Inhibitors and Methods Related Thereto," which compounds and synthetic methods are incorporated herein in their entirety, using an appropriate isotopically-labeled reagent in place of the non-labeled reagent previously employed.

Embodiments of this disclosure are also meant to encompass the in vivo metabolic products of the MNK-specific inhibitors of Formulae I, Ia, IIa, IIb, IIIa, IIIb, IVa, IVb, Va, Vb, VI, VIIa and VIIb. Such products may result from, for example, the oxidation, reduction, hydrolysis, amidation, esterification, and the like of the administered compound, primarily due to enzymatic processes. Accordingly, the instant disclosure includes compounds produced by a process comprising administering a MNK-specific inhibitor of this disclosure to a mammal for a period of time sufficient to yield a metabolic product thereof. Such products are typically identified by administering a radiolabelled MNK-specific inhibitor as described herein in a detectable dose to an animal, such as rat, mouse, guinea pig, monkey, or human, allowing sufficient time for metabolism to occur, and isolating conversion products from the urine, blood or other biological samples.

In some embodiments, a MNK-specific inhibitor of any one of compounds according to Formulae I, Ia, IIa, IIb, IIIa, IIIb, IVa, IVb, Va, Vb, VI, VIIa and VIIb are in the form of a pharmaceutically acceptable salt, which includes both acid and base addition salts.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of a MNK-specific inhibitor of this disclosure. As used herein, the term "solvate" refers to an aggregate that comprises one or more molecules of a compound of the invention with one or more molecules of solvent. A solvent may be water, in which case the solvate may be a hydrate. Alternatively, a solvent may be an organic solvent. Thus, the MNK-specific inhibitors of the present disclosure may exist as a hydrate, including a monohydrate, dihydrate, hemihydrate, sesquihydrate, trihydrate, tetrahydrate or the like, as well as the corresponding solvated forms. The MNK-specific inhibitors of this disclosure may be true solvates, while in other cases, the compounds may merely retain adventitious water or be a mixture of water plus some adventitious solvent.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are non-superimposeable mirror images of one another.

MNK-specific inhibitors of this disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. For example, when $W^1$ is oxo and $R^1$ is H, the present disclosure provides tautomers of a Formula I compound as illustrated below:

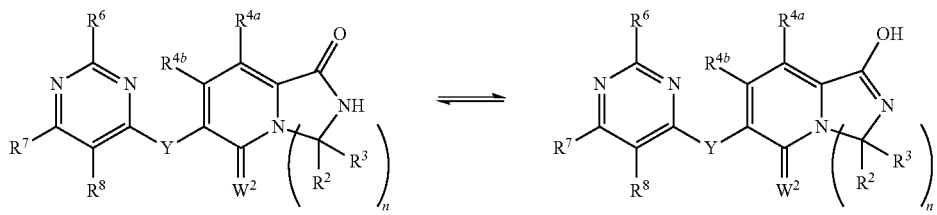

Similar tautomers exists for Formulae I, Ia, IIa, IIb, IIIa, IIIb, IVa, IVb, Va, Vb, VI, VIIa and VIIb compounds. The compounds are synthesized using conventional synthetic methods, and more specifically using the general methods and specific synthetic protocols of the Examples found in U.S. patent application Ser. No. 14/748,990 filed Jun. 24, 2015 and entitled "MNK Inhibitors and Methods Related Thereto," which compounds and synthetic methods are incorporated herein in their entirety.

Representative MNK-specific inhibitors of this disclosure are set forth in Table B and in U.S. Patent Application Publication No. US 2015/0376181, which compounds are incorporated herein by reference in their entirety. Similarly, incorporated herein by reference in their entirety are compounds and methods of making the same from U.S. Provisional Patent Application No. 62/247,953 (entitled "Isoindoline, Azaisoindoline, Dihydroindenone and Dihydroazaindenone Inhibitors of MNK1 and MNK2") and 62/247,966 (entitled "Pyrrolo-, Pyrazolo-, Imidazo-Pyrimidine and Pyridine Compounds that Inhibit MNK1 and MNK2"). Such compounds are provided for purpose of illustration and not limitation.

TABLE B

Exemplary MNK-Specific Inhibitors

| Cmpd. No. | Structure |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE B-continued

Exemplary MNK-Specific Inhibitors

| Cmpd. No. | Structure |
|---|---|
| 12 | 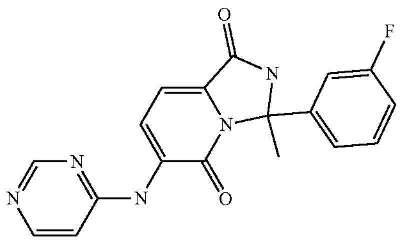 [SMILES: CC1(c2cccc(F)c2)NC(=O)c2ccc(Nc3ccncn3)c(=O)n21] |
| 13 | 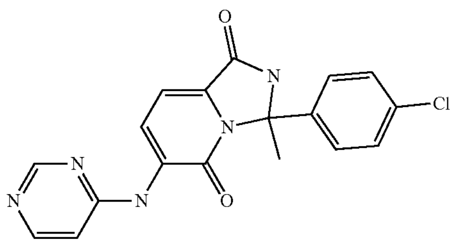 [SMILES: CC1(c2ccc(Cl)cc2)NC(=O)c2ccc(Nc3ccncn3)c(=O)n21] |
| 14 | 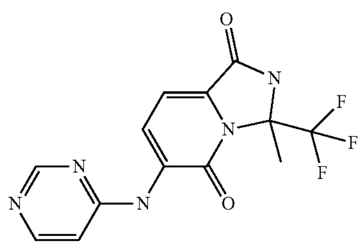 [SMILES: CC1(C(F)(F)F)NC(=O)c2ccc(Nc3ccncn3)c(=O)n21] |
| 15 | 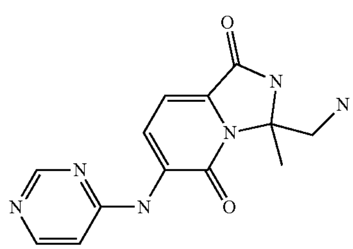 [SMILES: CC1(CN)NC(=O)c2ccc(Nc3ccncn3)c(=O)n21] |
| 16 | 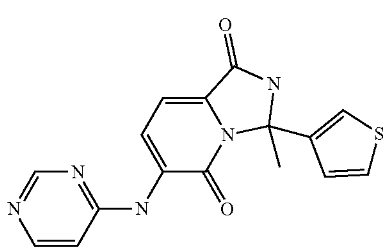 [SMILES: CC1(c2ccsc2)NC(=O)c2ccc(Nc3ccncn3)c(=O)n21] |
| 17 | 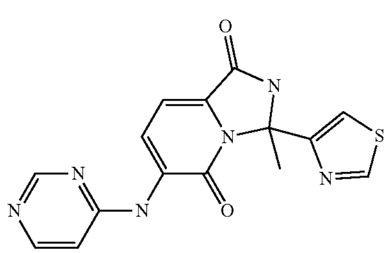 [SMILES: CC1(c2cscn2)NC(=O)c2ccc(Nc3ccncn3)c(=O)n21] |
| 18 | |
| 19 | |
| 20 | |
| 21 | |
| 22 | |

TABLE B-continued
Exemplary MNK-Specific Inhibitors
| Cmpd. No. | Structure |
|---|---|
| 23 | 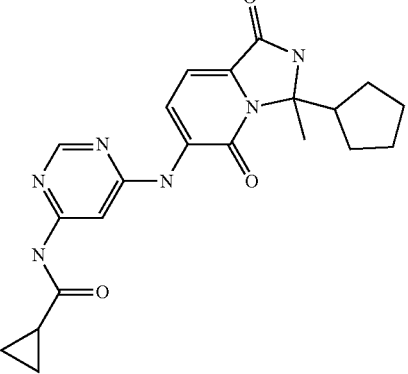 |
| 24 | 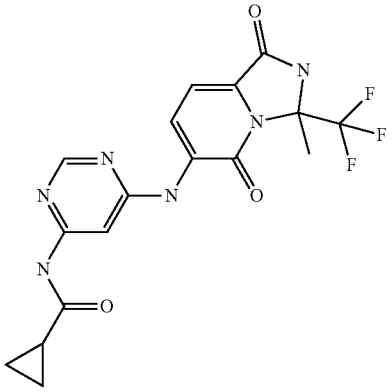 [SMILES: CC1(C(F)(F)F)NC(=O)c2ccc(Nc3cc(NC(=O)C4CC4)ncn3)c(=O)n21] |
| 25 | 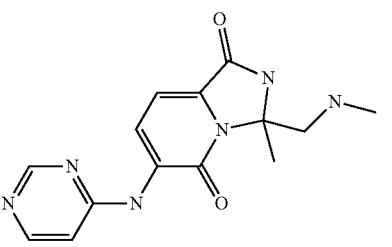 [SMILES: CNCC1(C)NC(=O)c2ccc(Nc3ccncn3)c(=O)n21] |
| 26 | 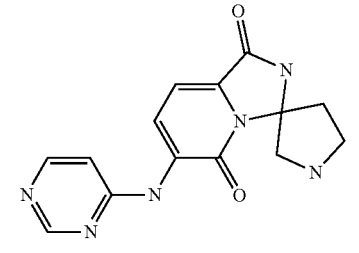 [SMILES: O=C1NC2(CCNC2)n2c1ccc(Nc1ccncn1)c2=O] |
| 27 | 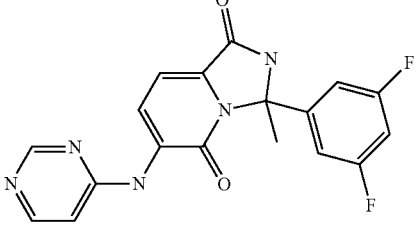 |
| 28 | 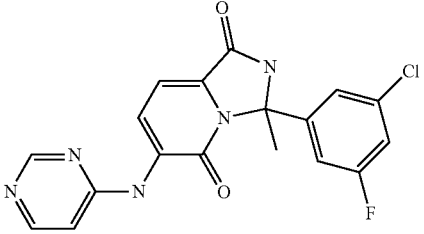 [SMILES: CC1(c2cc(F)cc(Cl)c2)NC(=O)c2ccc(Nc3ccncn3)c(=O)n21] |
| 29 | 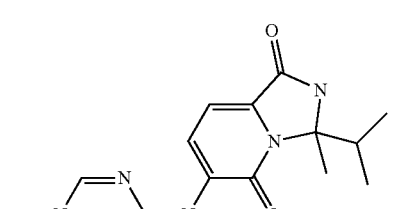 |
| 30 | 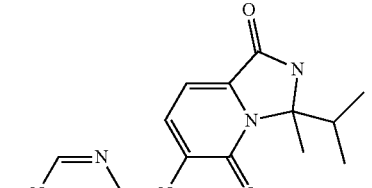 |
| 31 | 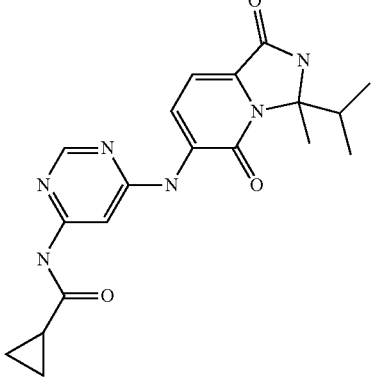 |

TABLE B-continued

Exemplary MNK-Specific Inhibitors

| Cmpd. No. | Structure |
|---|---|
| 32 | 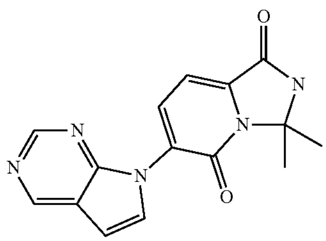 [SMILES: CC1(C)NC(=O)c2ccc(-n3ccc4cncnc43)c(=O)n21] |
| 33 | 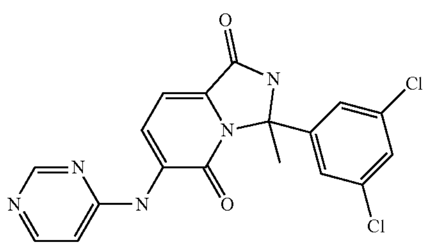 [SMILES: CC1(c2cc(Cl)cc(Cl)c2)NC(=O)c2ccc(Nc3ccncn3)c(=O)n21] |
| 34 | 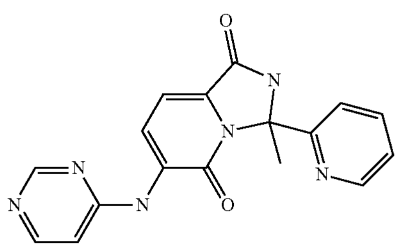 [SMILES: CC1(c2ccccn2)NC(=O)c2ccc(Nc3ccncn3)c(=O)n21] |
| 35 | 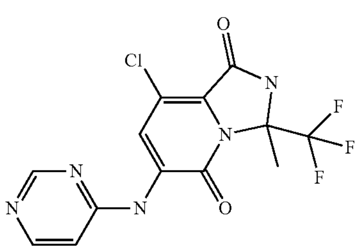 [SMILES: CC1(C(F)(F)F)NC(=O)c2c(Cl)cc(Nc3ccncn3)c(=O)n21] |
| 36 | 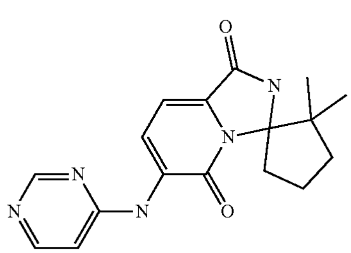 [SMILES: CC1(C)CCCC12NC(=O)c1ccc(Nc3ccncn3)c(=O)n12] |
| 37 | |
| 38 | |
| 39 | |
| 40 | |
| 41 | |

TABLE B-continued

Exemplary MNK-Specific Inhibitors

| Cmpd. No. | Structure |
|---|---|
| 42 | 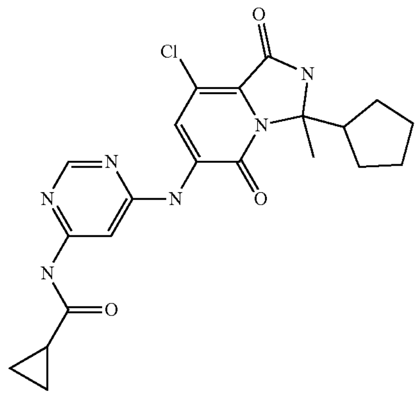 [SMILES: CC1(C2CCCC2)NC(=O)c2c(Cl)cc(Nc3cc(NC(=O)C4CC4)ncn3)c(=O)n21] |
| 43 | 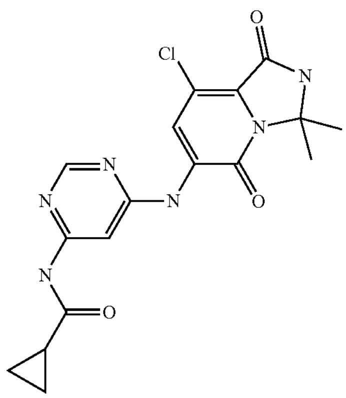 [SMILES: CC1(C)NC(=O)c2c(Cl)cc(Nc3cc(NC(=O)C4CC4)ncn3)c(=O)n21] |
| 44 | 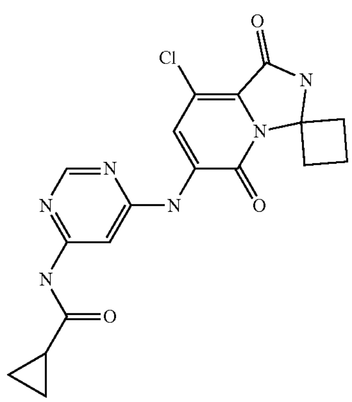 [SMILES: O=C1NC2(CCC2)n2c1c(Cl)cc(Nc1cc(NC(=O)C3CC3)ncn1)c2=O] |
| 45 | 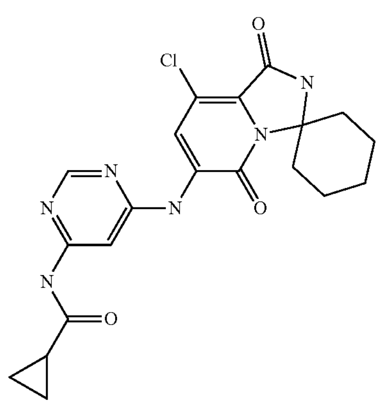 [SMILES: O=C1NC2(CCCCC2)n2c1c(Cl)cc(Nc1cc(NC(=O)C3CC3)ncn1)c2=O] |
| 46 | |
| 47 | |
| 48 | |
| 49 | |

TABLE B-continued
Exemplary MNK-Specific Inhibitors
| Cmpd. No. | Structure |
|---|---|
| 50 | 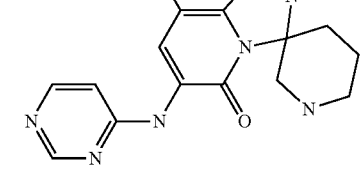 |
| 51 | |
| 52 | |
| 53 | |
| 54 | 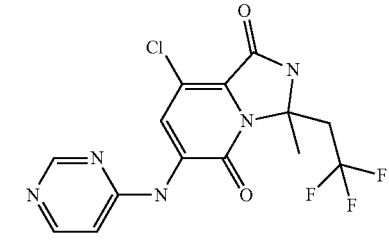 |
| 55 | 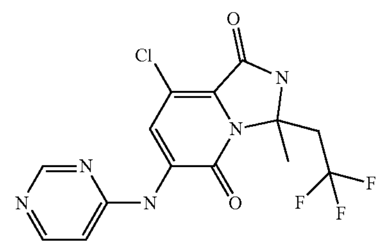 [SMILES: CC1(CC(F)(F)F)NC(=O)c2c(Cl)cc(Nc3ccncn3)c(=O)n21] |
| 56 | 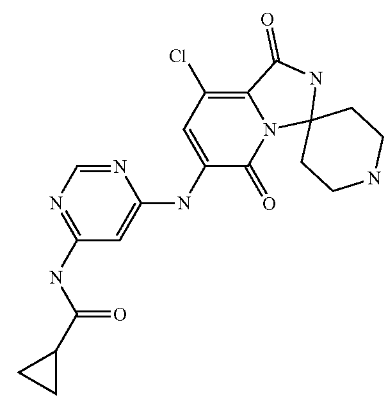 [SMILES: O=C1NC2(CCNCC2)n2c1c(Cl)cc(Nc1cc(NC(=O)C3CC3)ncn1)c2=O] |
| 57 | 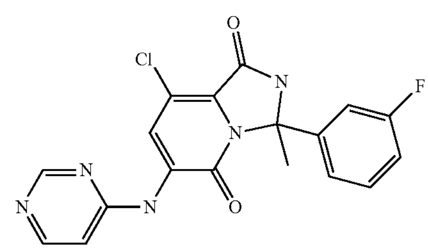 [SMILES: CC1(c2cccc(F)c2)NC(=O)c2c(Cl)cc(Nc3ccncn3)c(=O)n21] |
| 58 | 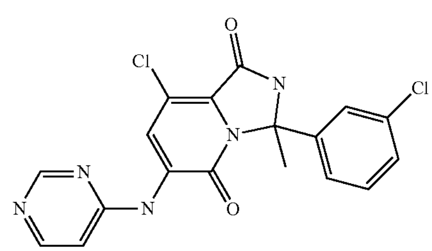 [SMILES: CC1(c2cccc(Cl)c2)NC(=O)c2c(Cl)cc(Nc3ccncn3)c(=O)n21] |

TABLE B-continued
Exemplary MNK-Specific Inhibitors
| Cmpd. No. | Structure |
|---|---|
| 59 | 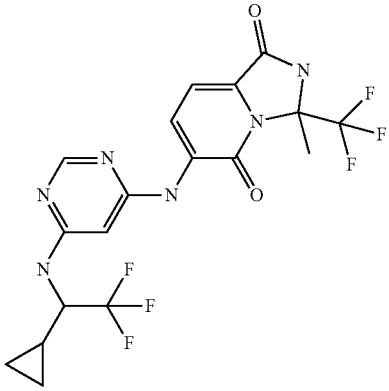 [SMILES: CC1(C(F)(F)F)NC(=O)c2ccc(Nc3cc(NC(C4CC4)C(F)(F)F)ncn3)c(=O)n21] |
| 60 | 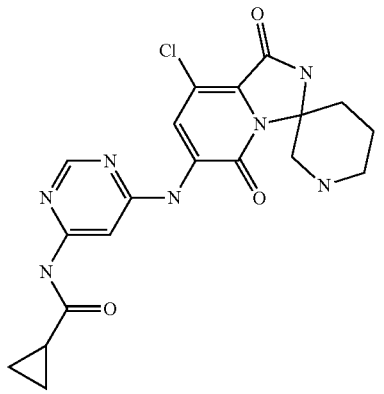 [SMILES: O=C1NC2(CCCNC2)n2c1c(Cl)cc(Nc1cc(NC(=O)C3CC3)ncn1)c2=O] |
| 61 | 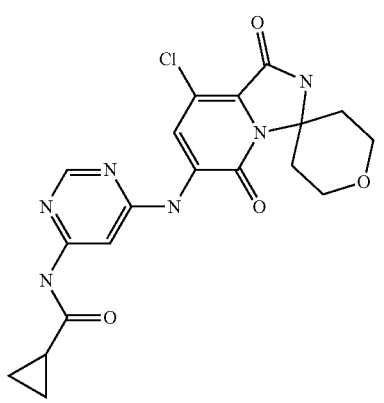 [SMILES: O=C1NC2(CCOCC2)n2c1c(Cl)cc(Nc1cc(NC(=O)C3CC3)ncn1)c2=O] |
| 62 | 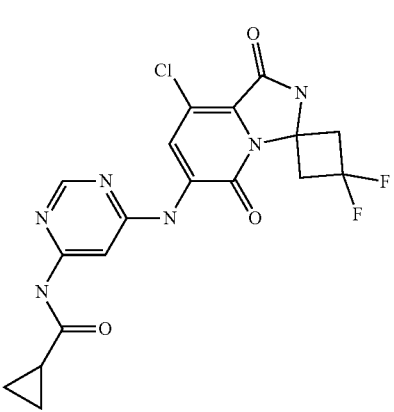 [SMILES: O=C1NC2(CC(F)(F)C2)n2c1c(Cl)cc(Nc1cc(NC(=O)C3CC3)ncn1)c2=O] |
| 63 | 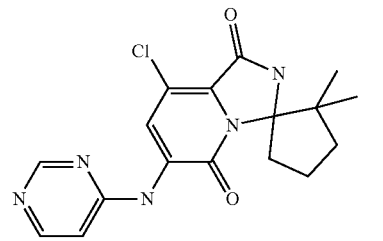 [SMILES: CC1(C)CCCC12NC(=O)c1c(Cl)cc(Nc3ccncn3)c(=O)n12] |
| 64 | 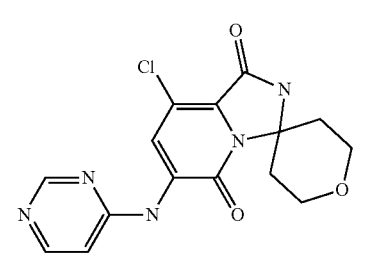 [SMILES: O=C1NC2(CCOCC2)n2c1c(Cl)cc(Nc1ccncn1)c2=O] |
| 65 | 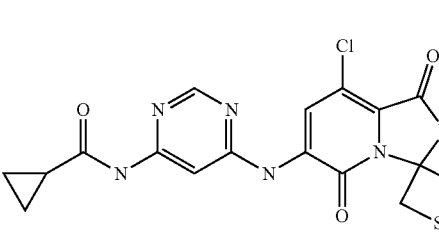 |
| 66 | 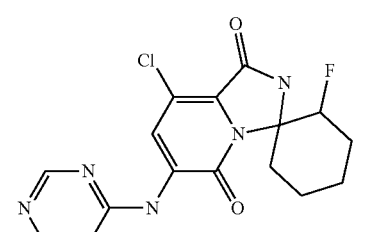 |
| 67 | 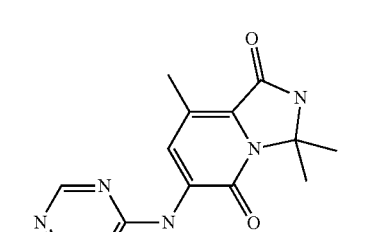 |
| 68 | 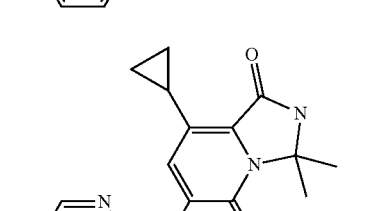 |

TABLE B-continued

Exemplary MNK-Specific Inhibitors

| Cmpd. No. | Structure |
|---|---|
| 69 | 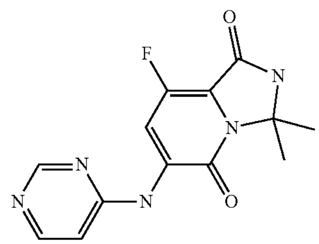 [SMILES: CC1(C)NC(=O)c2c(F)cc(Nc3ccncn3)c(=O)n21] |
| 70 | 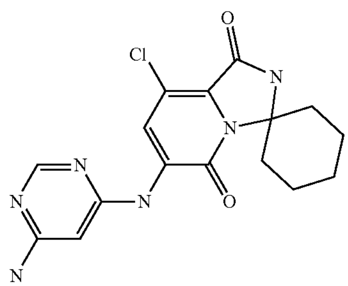 [SMILES: Nc1cc(Nc2cc(Cl)c3n(c2=O)C2(CCCCC2)NC3=O)ncn1] |
| 71 | 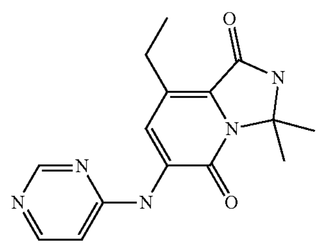 [SMILES: CCc1cc(Nc2ccncn2)c(=O)n2c1C(=O)NC2(C)C] |
| 72 | 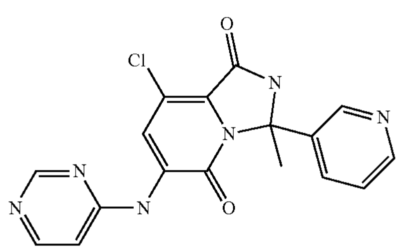 [SMILES: CC1(c2cccnc2)NC(=O)c2c(Cl)cc(Nc3ccncn3)c(=O)n21] |
| 73 | 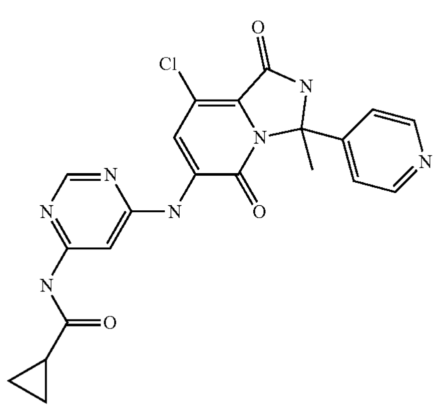 [SMILES: CC1(c2ccncc2)NC(=O)c2c(Cl)cc(Nc3cc(NC(=O)C4CC4)ncn3)c(=O)n21] |
| 74 | |
| 75 | |
| 76 | |
| 77 | |

TABLE B-continued
Exemplary MNK-Specific Inhibitors
| Cmpd. No. | Structure |
|---|---|
| 78 | 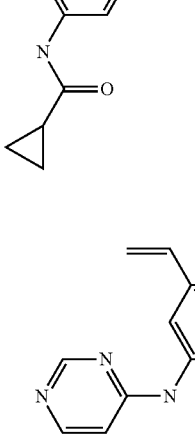 |
| 79 | 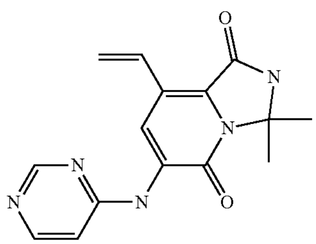 [SMILES: C=Cc1cc(Nc2ccncn2)c(=O)n2c1C(=O)NC2(C)C] |
| 80 | 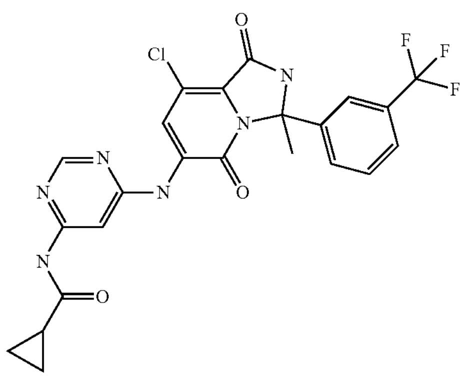 [SMILES: CC1(c2cccc(C(F)(F)F)c2)NC(=O)c2c(Cl)cc(Nc3cc(NC(=O)C4CC4)ncn3)c(=O)n21] |
| 81 | 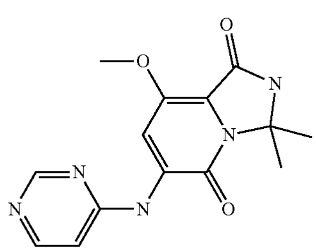 [SMILES: COc1cc(Nc2ccncn2)c(=O)n2c1C(=O)NC2(C)C] |
| 82 | 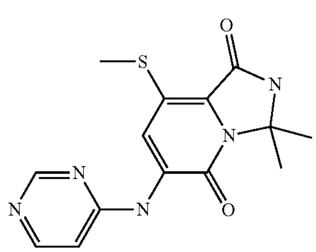 [SMILES: CSc1cc(Nc2ccncn2)c(=O)n2c1C(=O)NC2(C)C] |
| 83 | 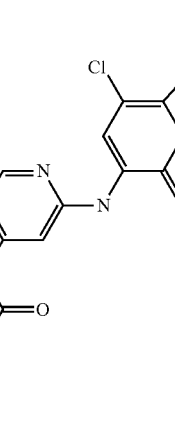 |
| 84 | |
| 85 | |

TABLE B-continued
Exemplary MNK-Specific Inhibitors
| Cmpd. No. | Structure |
|---|---|
| 86 | 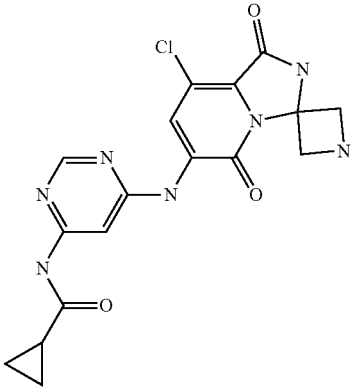 [SMILES: O=C1NC2(CNC2)n2c1c(Cl)cc(Nc1cc(NC(=O)C3CC3)ncn1)c2=O] |
| 87 | 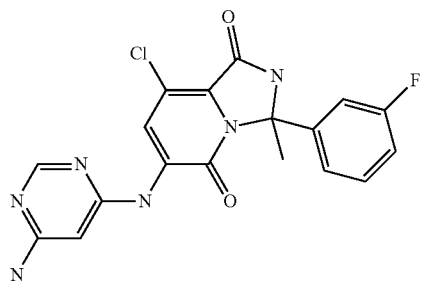 [SMILES: CC1(c2cccc(F)c2)NC(=O)c2c(Cl)cc(Nc3cc(N)ncn3)c(=O)n21] |
| 88 | 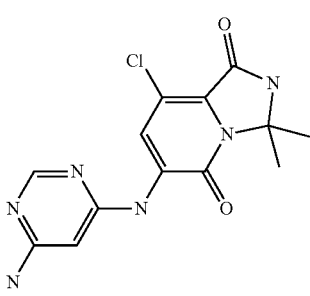 [SMILES: CC1(C)NC(=O)c2c(Cl)cc(Nc3cc(N)ncn3)c(=O)n21] |
| 89 | 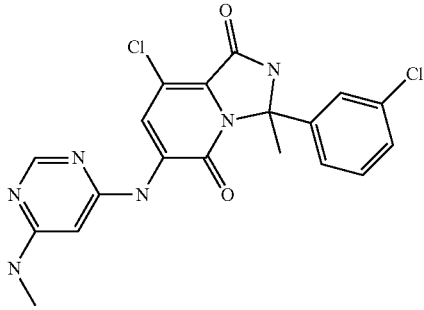 [SMILES: CNc1cc(Nc2cc(Cl)c3n(c2=O)C(C)(c2cccc(Cl)c2)NC3=O)ncn1] |
| 90 | 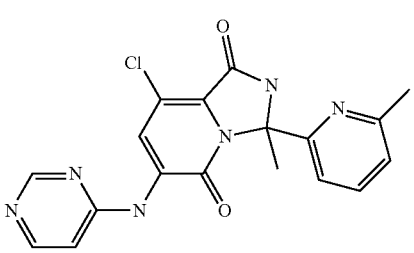 [SMILES: Cc1cccc(C2(C)NC(=O)c3c(Cl)cc(Nc4ccncn4)c(=O)n32)n1] |
| 91 | 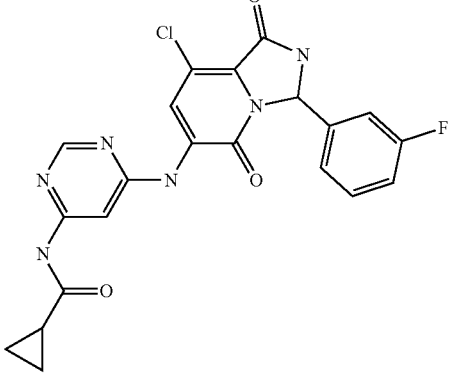 |
| 92 | 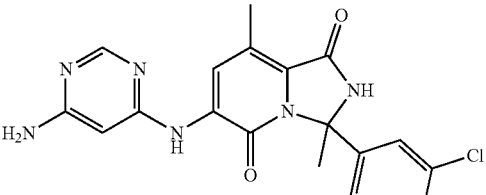 |
| 93 | 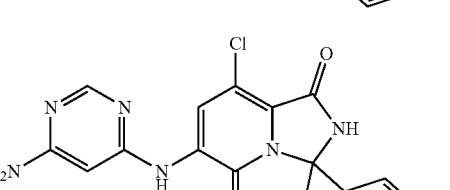 |
| 94 | 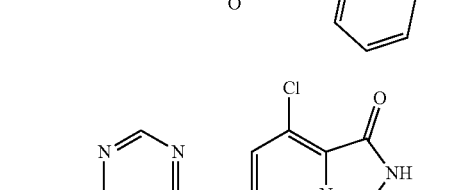 |
| 95 | 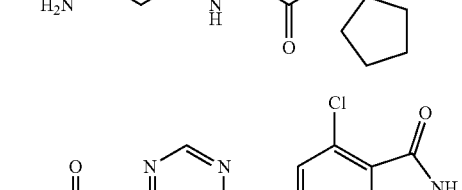 |
| 96 | 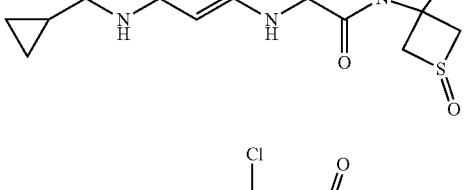 |

TABLE B-continued

Exemplary MNK-Specific Inhibitors

| Cmpd. No. | Structure |
|---|---|
| 97 | [chemical structure] |
| 98 | [chemical structure] |
| 99 | [chemical structure] |
| 100 | [chemical structure] |
| 101 | [chemical structure] |
| 102 | [chemical structure] |
| 103 | [chemical structure] |
| 104 | [chemical structure] |
| 105 | [chemical structure] |
| 106 | [chemical structure] |
| 107 | [chemical structure] |
| 108 | [chemical structure] |

TABLE B-continued

Exemplary MNK-Specific Inhibitors

| Cmpd. No. | Structure |
|---|---|
| 109 | *(structure: 8-chloro-6-(pyrimidin-4-ylamino)spiro pyridoimidazolone cyclohexane, HCl)* |
| 110 | *(structure: 8-chloro-6-(pyrimidin-4-ylamino)spiro pyridoimidazolone 4,4-difluorocyclohexane, HCl)* |
| 111 | *(structure: 8-chloro-6-((6-aminopyrimidin-4-yl)amino)spiro pyridoimidazolone chloroindane, HCl)* |
| 112 | *(structure: 8-chloro-6-((5-fluoropyrimidin-4-yl)amino)spiro pyridoimidazolone cyclohexane)* |
| 440 | *(structure: methyl-isoindolinone-spiro-cyclohexane with (5-amino-6-methylpyrimidin-4-yl)amino substituent)* |
| 462 | *(structure: methyl-isoindolinone-spiro-cyclohexane with (5-amino-6-chloropyrimidin-4-yl)amino substituent)* |
| 474 | *(structure: methyl pyridoimidazolone spiro cyclohexane with (5-amino-6-chloropyrimidin-4-yl)amino substituent)* |
| 590 | *(structure: methyl pyridoimidazolone spiro piperidine N-(2,2-difluoroethyl) with (6-amino-5-methylpyrimidin-4-yl)amino)* |
| 611 | *(structure: methyl pyridoimidazolone spiro piperidine N-(2,2-difluoroethyl) with (6-amino-5-chloropyrimidin-4-yl)amino)* |
| 622 | *(structure: methyl pyrrolopyridinone spiro cyclohexane with (6-amino-5-methylpyrimidin-4-yl)amino)* |
| 624 | *(structure: methyl pyrrolopyridinone spiro cyclohexane with (6-amino-5-chloropyrimidin-4-yl)amino)* |

TABLE B-continued

Exemplary MNK-Specific Inhibitors

| Cmpd. No. | Structure |
|---|---|
| 626 | (structure) |
| 637 | (structure) |
| 652 | (structure) |
| 750 | (structure) |
| 752 | (structure) |
| 753 | (structure) |
| 775 | (structure) |
| 776 | (structure) |
| 827 | (structure) |
| 917 | (structure) |

TABLE B-continued

Exemplary MNK-Specific Inhibitors

| Cmpd. No. | Structure |
|---|---|
| 969 | *(structure)* |
| 970 | *(structure)* |
| 1008 | *(structure)* |
| 1031 | *(structure)* |
| 1053 | *(structure)* |
| 1090 | *(structure)* |
| 1091 | *(structure)* |
| 1092 | *(structure)* |

In certain embodiments, a MNK-specific inhibitor is a compound of any one of Formulae I, Ia, IIa, IIb, IIIa, IIIb, IVa, IVb, Va, Vb, VI, VIIa and VIIb, or from Table B, which is formulated as a pharmaceutical composition in an amount effective to treat a particular disease or condition of interest (e.g., cancer, chronic infection) upon administration of the pharmaceutical composition to a mammal (e.g., human). In particular embodiments, a pharmaceutical composition comprises a MNK-specific inhibitor as described herein and a pharmaceutically acceptable carrier, diluent or excipient.

In this regard, a "pharmaceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved by the United States Food and Drug Administration as being acceptable for use in humans or domestic animals.

A pharmaceutical composition of a MNK-specific inhibitor as described herein may be in the form of a solid or liquid. In one aspect, the carrier(s) are particulate so that the compositions are, for example, in tablet or powder form. The carrier(s) may be liquid, with a composition being, for example, an oral syrup, injectable liquid or an aerosol, which is useful in, for example, inhalatory administration. When intended for oral administration, a pharmaceutical composition of a MNK-specific inhibitor of this disclosure is preferably in either solid or liquid form, where semi-solid, semi-liquid, suspension and gel forms are included within the forms considered herein as either solid or liquid.

As a solid composition for oral administration, a pharmaceutical composition of a MNK-specific inhibitor as described herein may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

A pharmaceutical composition may be in the form of a liquid, for example, an elixir, syrup, solution, emulsion or suspension. The liquid may be for oral administration or for delivery by injection, as two examples. When intended for oral administration, preferred compositions contain, in addition to a MNK-specific inhibitor, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of MNK-specific inhibitors, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of a MNK-specific inhibitor intended for either parenteral or oral administration should contain an amount of a MNK-specific inhibitor of this disclosure such that a suitable dosage will be obtained.

A pharmaceutical composition of a MNK-specific inhibitor may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, a composition of a MNK-specific inhibitor of this disclosure may be included with a transdermal patch or iontophoresis device.

The pharmaceutical composition of a MNK-specific inhibitor may be intended for rectal administration, in the form, for example, of a suppository, which will melt in the rectum and release the drug. A composition for rectal administration may contain an oleaginous base as a suitable nonirritating excipient. Such bases include, for example, lanolin, cocoa butter or polyethylene glycol.

The pharmaceutical composition of a MNK-specific inhibitor may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of this disclosure in solid or liquid form may include an agent that binds to a MNK-specific inhibitor described herein and thereby assist in the delivery of the compound. Suitable agents that may act in this capacity include a monoclonal or polyclonal antibody, a protein or a liposome.

A pharmaceutical composition of a MNK-specific inhibitor may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of MNK-specific inhibitors may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine preferred aerosol formulations and delivery modes.

EXAMPLES

Example 1

In Vitro Effect of MNK-Specific Inhibitors on Formation of Central Memory T Cells and Cytotoxic T Cell Function Materials and Methods
Antibodies and Reagents Antibodies against CD4 (GK1.5-PE), CD45.1 (A20-APC), CD8 (53-6-7-APC or -PE), and RBC lysis solution were purchased from BioLegend (San Diego, Calif.). The anti-CD44 (IM7-PE-Cy7) antibody, anti-CD62L (MEL14-Pacific Blue) antibody, CellTrace™ Violet reagent, DMEM media, and fetal bovine serum (FBS) were purchased from ThermoFisher (Waltham, Mass.). OVA MHC class I epitope peptide SIINFEKL (SEQ ID NO:1) was purchased from InvivoGen (San Diego, Calif.). Horizon™ Fixable Viability Stain (FVS) reagent was purchased from BD Biosciences (San Jose, Calif.).

Animal Studies

OT-I mice (C57BL/6-Tg(TcraTcrb)1100Mjb/J) were purchased from The Jackson Laboratory (Bar Harbor, Me.). Ly5.1 mice (B6.SJL-Ptprc$^a$Pepc$^b$/BoyCrCrl) were purchased from Charles River (Wilmington, Mass.). C57BL/6 and BALB/c mice were purchased from Simonsen Laboratories (Gilroy, Calif.). All animal studies were carried out in accordance with the guidelines established by the Institutional Animal Care and Use Committee at Explora BioLabs (San Diego, Calif.).

Assessment of T cell Memory Formation

Spleens were isolated from OT-I and processed into a single cell suspension. Red blood cells (RBCs) were lysed using RBC lysis solution. Splenocytes ($2 \times 10^6$ cells/ml) were cultured in complete media (10% FBS in DMEM) and stimulated with 5 μg/ml OVA MHC class I epitope peptide (SIINFEKL, SEQ ID NO:1) in the absence or presence of 0.01 μM, 0.1 μM, 1.0 μM, 3.0 μM, or 10 μM of MNK-specific inhibitor, Compound 107, for 48 hrs. For the mixed lymphocyte reaction (MLR) assay, peritoneal macrophages were first isolated from BALB/c mice by peritoneal wash with chilled DMEM media. This lavage was plated in a 24 well plate for 2 h at 37° C. After 2 h, non-adherent cells were washed to remove non-macrophage populations. The adherent cells (primarily peritoneal macrophages) were cultured in complete media in the absence or presence of the indicated Compound 107 concentrations for 24 h. After 24 h, panned splenocytes (enriched in T cells) from C57BL/6 mice were added to the macrophage culture in the absence or presence of Compound 107 for an additional 4 days.

The cells were harvested from the MLR, washed and stained with Horizon™ FVS, anti-CD4, anti-CD8, anti-CD44 and anti-CD62L antibodies. The cells were analyzed by flow cytometry (Attune NXT, ThermoFisher) and FlowJo analysis software (FlowJo LLC, Ashland Oreg.). CD8+ and CD4+ cells populations were analyzed for expression of CD44 and CD62L. $CD44^{high}CD62^{low}$ define effect memory T cells ($T_{EM}$) and $CD44^{high}CD62L^{high}$ define central memory T cells ($T_{CM}$).

T Cell Killing Assay

Spleens were isolated from OT-I mice and processed into a single cell suspension. Red blood cells (RBCs) were lysed using RBC lysis solution. Splenocytes ($4 \times 10^6$ cells/ml) were cultured and stimulated with 5 μg/ml OVA MHC class I epitope peptide (SIINFEKL, SEQ ID NO:1) in the absence or presence of 0.01 μM, 0.1 μM, 1.0 μM, 3.0 μM, or 10 μM of Compound 107 for 3 days. Target cells were prepared by panning the splenocytes from CD45.1-expressing Ly5.1 mice to remove macrophage populations. Splenocytes remaining in the supernatant were divided into two groups: one group labeled with 5 μM CellTrace Violet ($CellTrace^{high}$) and the other group labeled with 0.5 μM CellTrace Violet ($CellTrace^{low}$) $CellTrace^{high}$ splenocytes were then pulsed with 3 μg/ml SIINFEKL peptide for 45 min. Both populations were washed twice, counted and mixed together in a 1:1 ratio. The labeled target cell mixture ($4 \times 10^5$ cells) was co-cultured with washed OT-I splenocytes ($4 \times 10^6$ cells) for 16 h in the absence of Compound 107. The cells were harvested, washed and stained with Horizon™ FVS and anti-CD45.1 APC antibody. The cells were analyzed by flow cytometry (Attune NXT) and FlowJo analysis software. Target cells were gated by CD45.1 expression and analyzed for CellTrace Violet levels. The % cell killing relative to target cells alone was calculated using the following formula:

$$[1-(CellTrace^{high}/CellTrace^{low})_{experimental}/(CellTrace^{high}/CellTrace^{low})_{control}] \times 100$$

Results

Figure 1B:
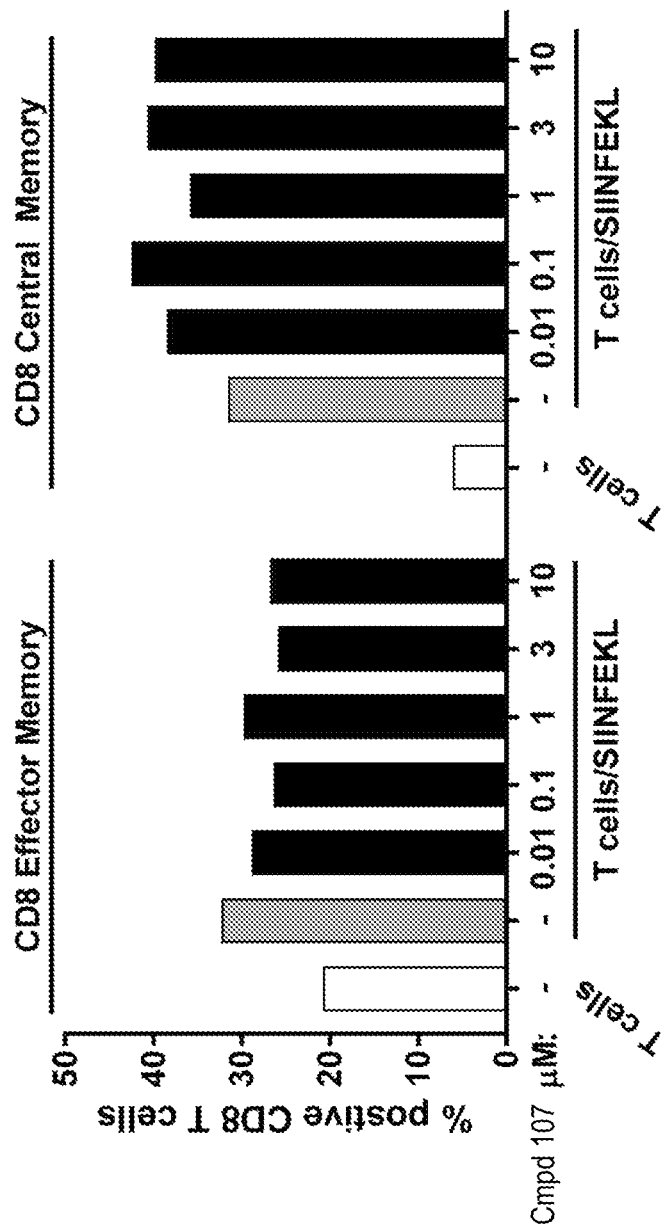

Compound 107 was assessed for effects on T cell memory formation in vitro, both in the context of specific peptide antigen stimulation and in a mixed lymphocyte reaction. In the peptide stimulation experiment (FIG. 1A), unstimulated CD8+ T cells showed a distribution of effector memory ($T_{EM}$) cells and central memory ($T_{CM}$) cells of 21% and 6%, respectively. Stimulation with OVA MHC Class I epitope peptide (SIINFEKL SEQ ID NO:1) led to an increase in both $T_{EM}$ and $T_{CM}$ pools to 32%, and the presence of the MNK-specific inhibitor Compound 107 enhanced the distribution of cells in the $T_{CM}$ pool to 36-41% (FIGS. 1A and 1B).

Figure 1C:
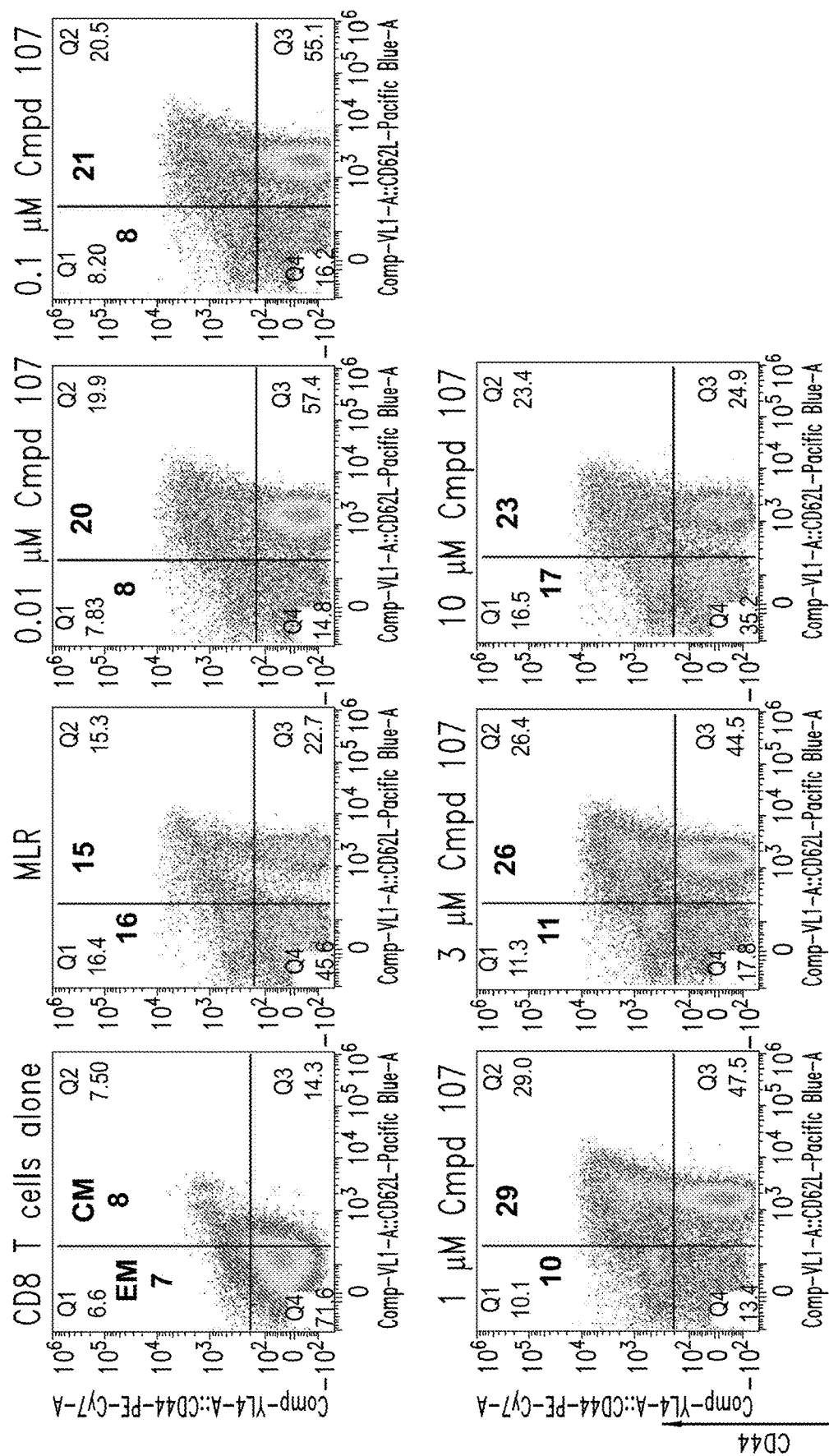
Figure 1D:
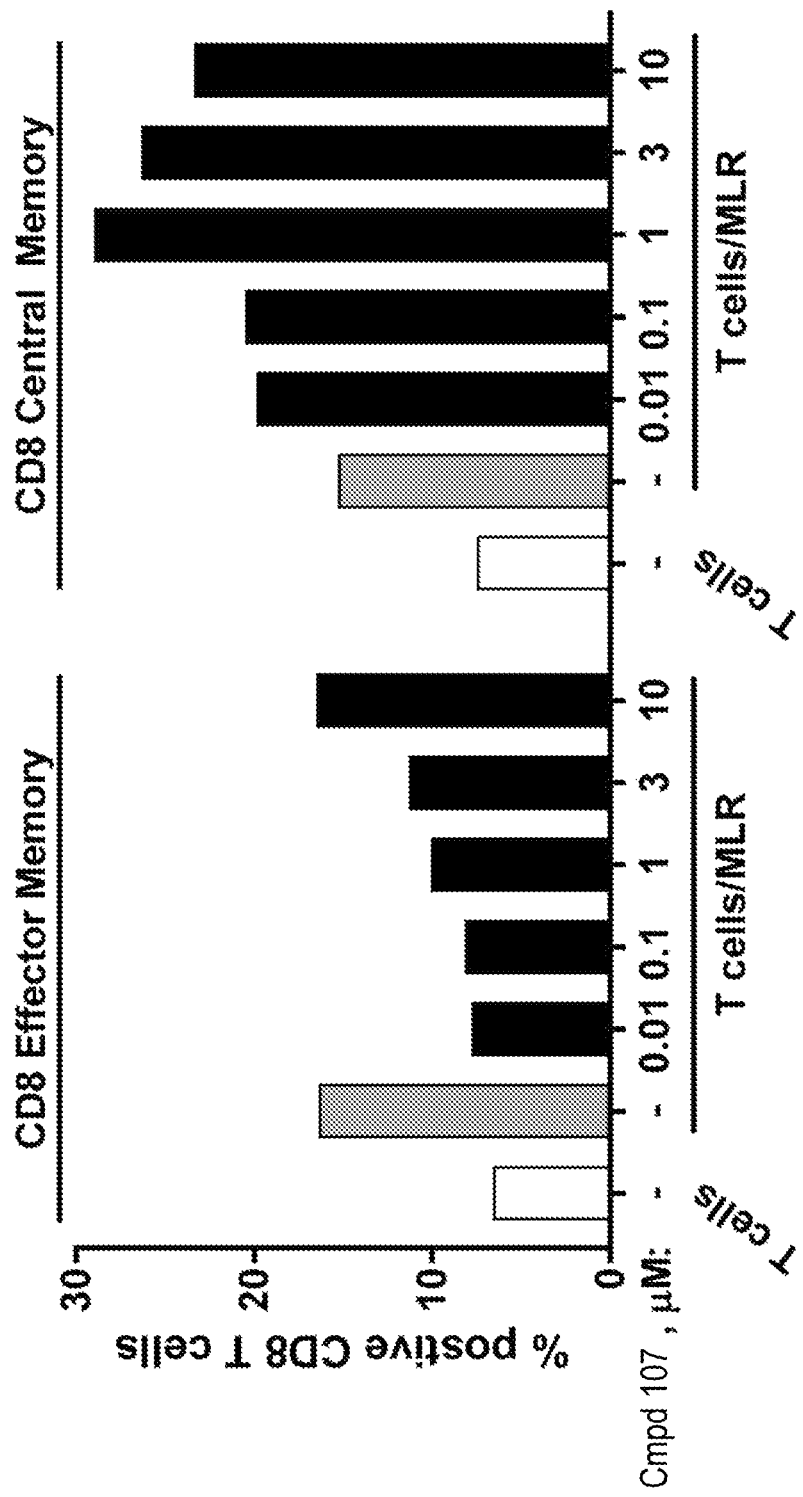
Figure 1E:
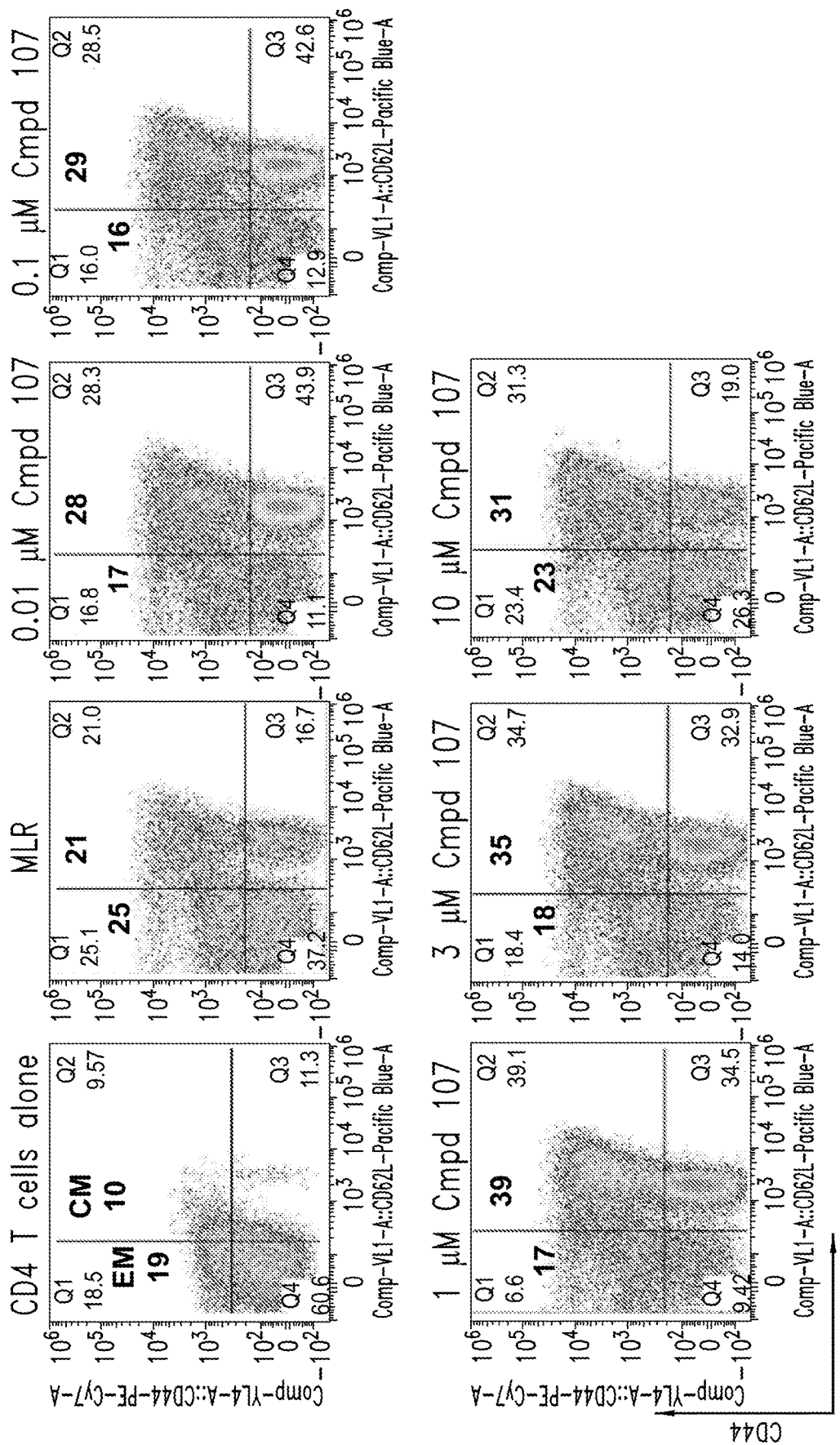
Figure 1F:
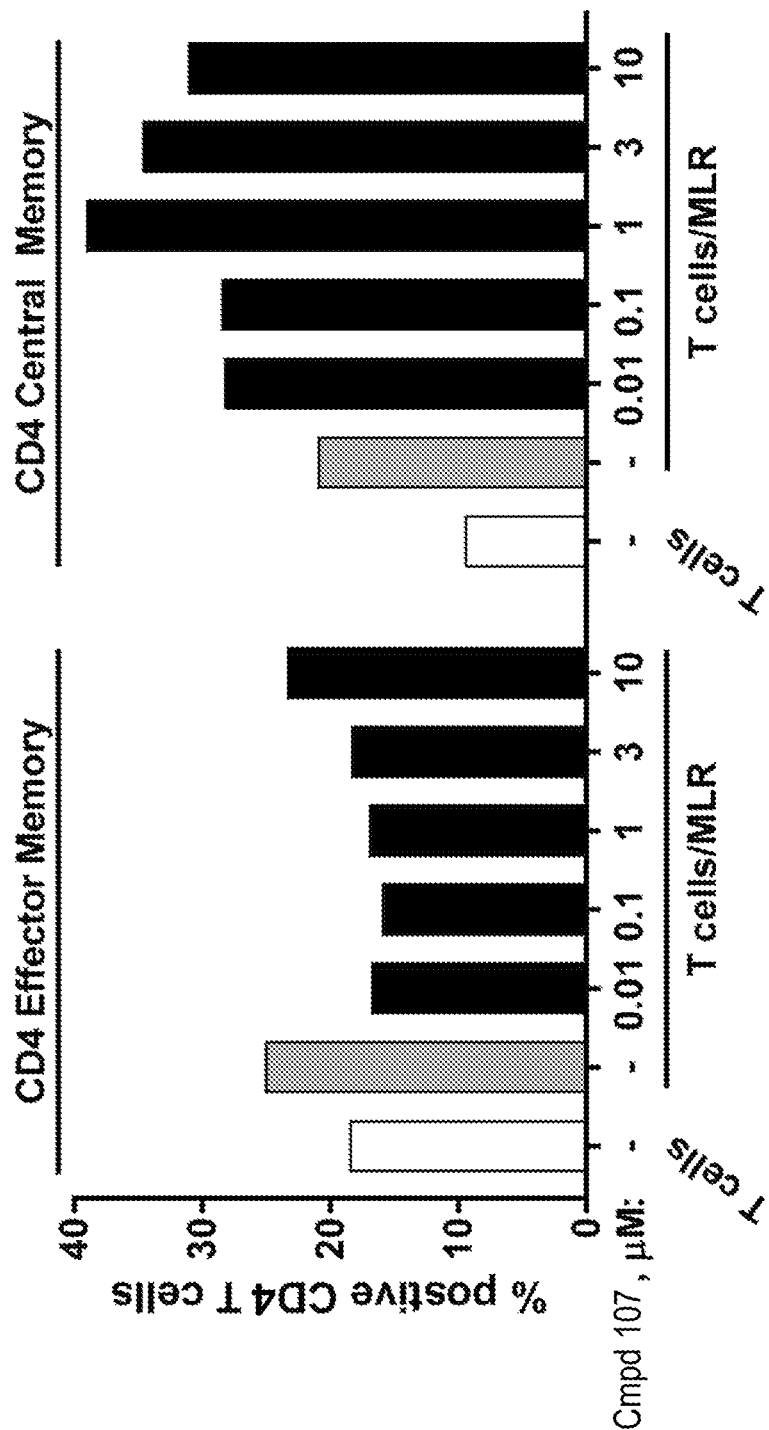

In MLR experiments, unstimulated CD8 T cells had $T_{EM}$ and $T_{CM}$ pools of 7% and 8%, respectively, while stimulation increased these pools to 16% and 15%, respectively (FIGS. 1C and 1D). In the presence of MNK-specific inhibitor Compound 107, the pool of $T_{CM}$ CD8+ T cells increased to 20-29%, while the $T_{EM}$ pool showed slight decreases to 8-11% at 0.01-3 μM of Compound 107 (FIGS. 1C and 1D). Similar results were seen when analyzing CD4+ T cells in the MLR reaction, where the presence of Compound 107 further increased the pool of $T_{CM}$ CD4+ T cells (28-39%), compared to the MLR alone (21%) (FIGS. 1E and 1F). Slight decreases were also observed in the $T_{EM}$ CD4+ T cell pool in the presence of Compound 107 (16-23%) compared to the MLR alone (25%) (FIGS. 1E and 1F).

Taken together, these data demonstrate that MNK-specific inhibitors (e.g., Compound 107) can induce an increase in the pool of $T_{CM}$ cells in both CD4+ and CD8+ T cell populations.

Figure 2:
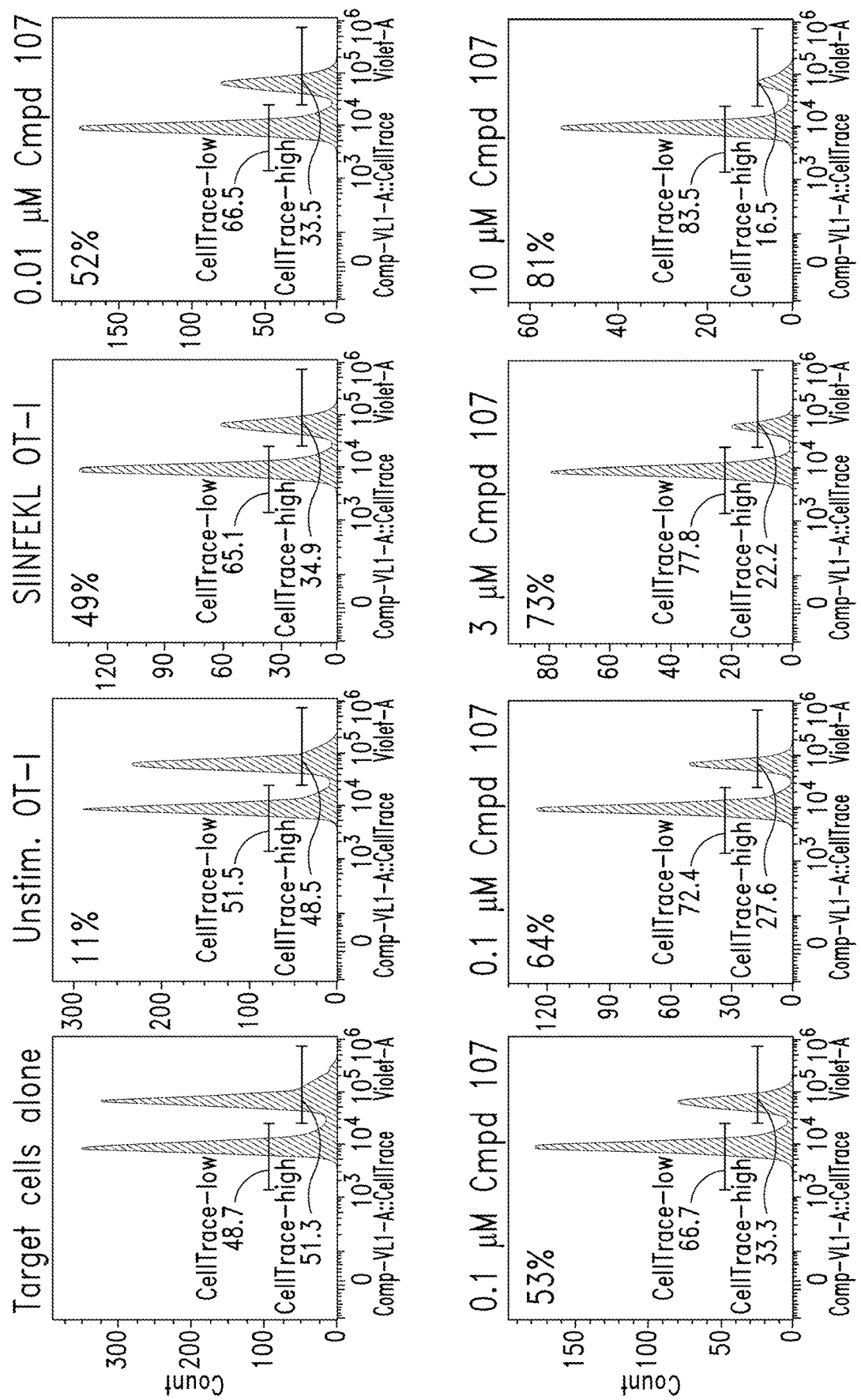
FIG. 2 shows that MNK-specific inhibitors can increase cytotoxic T cell function. Flow cytometry plots of CellTrace Violet-labeled CD45.1$^+$ target cell populations in the T cell killing assay are shown. The % cell killing relative to target cells alone is shown in in upper left corner.

MNK-specific inhibitor Compound 107 was also assessed for effects on cytotoxic T cell function in vitro (FIG. 2). In this experiment, T cells from OT-I mice were stimulated with peptide (SIINFEKL, SEQ ID NO:1) in the absence or presence of Compound 107, then assayed for cytotoxic function by incubation with target cells (1:1 mixture of a cell population either presenting SIINFEKL on MHC class I or not). Unstimulated OT-I cells showed little killing of target cells (11%), while SIINFEKL peptide (SEQ ID NO:1) stimulation of OT-I cells increased target cell kill to 49%. OT-I cells stimulated with both SIINFEKL peptide and Compound 107 showed a dose-dependent increase of cell killing from 52% to 81%. These data demonstrate that Compound 107 can enhance cytotoxic T cell function.

Example 2

In Vivo Effect of Mnk-Specific Inhibitors on Formation of Central Memory T Cells and Cytotoxic T Cell Function Materials and Methods Reagents Antibodies against CD4 (GK1.5-PE), CD45.1 APC, CD45.2 APC and CD8 (53-6-7-APC or PE) were purchased from BioLegend (San Diego, Calif.). CD44-PE-Cy7, CD62L-Pacific blue were purchased from Life technology (Carlsbad, Calif.). BD Horizon Fixable Viability Stain was purchased from (BD Biosciences, San Jose, Calif.). OVA MHC Class I epitope peptide SIINFEKL (SEQ ID NO:1) was purchased from InvivoGen (San Diego, Calif.). CellTrace Violet and DMEM media were purchased from ThermoFisher (Waltham, Mass.). E.G7-OVA, a murine lymphoma cell line engineered to express the ovalbumin peptide SIINFEKL (SEQ ID NO:1), was purchased from ATCC (Manassas, Va.) and maintained in RPMI supplemented with 10% fetal bovine serum (ThermoFisher).

Animal Studies

OT-I mice (C57BL/6-Tg(TcraTcrb)1100Mjb/J), which express a transgenic TCR specific for the ovalbumin peptide SIINFEKL (SEQ ID NO:1), were purchased from The Jackson Laboratory (Bar Harbor, Me.). B6.SJL mice (CD45.1 expressing B6.SJL-PtprcaPepcb/BoyCrCrl) and C57BL/6 mice were purchased from Charles River (Wilmington, Mass.). Athymic nude mice were purchased from Simonsen Laboratories (Gilroy, Calif.). All animal studies were carried out in accordance with the guidelines established by the Institutional Animal Care and Use Committee at Explora BioLabs (San Diego, Calif.).

Assessment of Long-Term Memory/Recall Response

Spleens were isolated from OT-I mice and CD3+ T cells were isolated using the MojoSort Mouse CD3 T Cell Isolation Kit (Biolegend, San Diego Calif.). OT-I T cells ($2 \times 10^6$ cells) were adoptively transferred into B6.SJL mice through intravenous tail vein injection. Mice were dosed orally with vehicle or 1 mg/kg Compound 107 24 hrs later and vaccinated subcutaneously with SIINFEKL peptide (SEQ ID NO:1) (50 µg/mouse). Mice were dosed with vehicle or 1 mg/kg Compound 107 for an additional six days. On day 21 post-immunization, selected groups were boosted with an additional injection of SIINFEKL peptide (SEQ ID NO:1) (50 µg/mouse). On day 24, spleens were harvested from animals and processed into a single cell suspension for flow cytometry analysis. Cells were stained with BD Horizon Fixable Viability Stain and antibodies against CD45.2, CD8, and CD44. Cells were analyzed using an Attune NXT flow cytometer and data was processed using FlowJo 10.1 software.

In Vivo Tumor Growth Inhibition

E.G7-OVA tumor cells ($2 \times 10^6$) were implanted subcutaneously into athymic nude mice. On day 7 post-implant, tumors were measured (~192 mm$^3$) and tumor-bearing animals were randomized into 6 groups. T cells purified from OT-I mouse spleens were cultured for 48 h in vitro with DMSO/PBS control alone, 50 µg/ml SIINFEKL peptide (SEQ ID NO:1) alone, 1 µM Compound 107, or the combination of 50 µg/ml SIINFEKL (SEQ ID NO:1) and 1 µM Compound 107. The in vitro treated OT-I T cells were adoptively transferred into animals from the appropriate groups ($2 \times 10^6$ cells/mouse) by tail vein injection. Animals were dosed in vivo with vehicle or 1 mg/kg Compound 107 and tumor size and body weight was monitored during the course of the study.

Results

Long Term Memory/Recall Response

Figure 3:
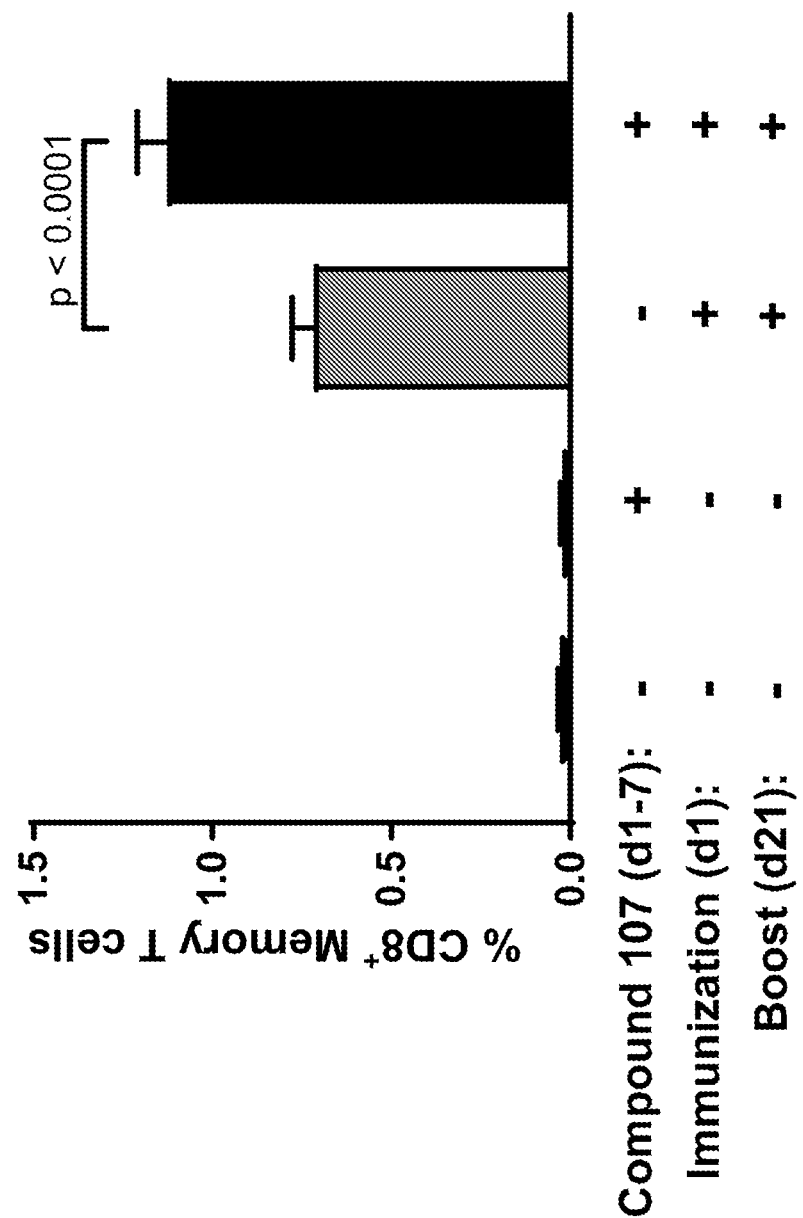
FIG. 3 shows that MNK-specific inhibitor enhances long-term memory recall in vivo. OT-I T cells were adoptively transferred into B6.SJL mice (day 0). Mice were treated with Compound 107, immunized, and boosted as indicated (days post-transfer). Spleens were harvested on day 24 and processed for flow cytometry analysis. CD45.2$^+$CD8$^+$CD44$^+$ Memory T cells are plotted as a percentage of total lymphocytes from two independent experiments. Bars, average from animals in group (n=12 over two experiments); Error bars, SEM.

The ability of Compound 107 to affect T cell memory formation was also assessed in vivo. In these studies, OT-I T cells were adoptively transferred into B6.SJL recipient mice. On day 1, mice were treated with vehicle or Compound 107 followed by immunization with SIINFEKL peptide (SEQ ID NO:1). Mice continued to be treated with vehicle or Compound 107 for an additional 6 days. Mice were boosted with SIINFEKL peptide (SEQ ID NO:1) at day 21 post-immunization, and spleens were harvested on day 24 for flow cytometry analysis. OT-I memory T cells were scored as CD45.2+CD8+CD44+ cells and expressed as a percentage of the total lymphocyte population in spleen (FIG. 3). In the absence of SIINFEKL peptide (SEQ ID NO:1) immunization and boost, the percentage of OT-I memory T cells in the spleen was very low after 24 days. Furthermore, the population of OT-I memory T cells in un-immunized animals was unaffected by Compound 107 treatment. In contrast, animals that were immunized and subsequently boosted showed a substantial increase in the percentage of OT-I memory T cells in the spleen after 24 days. In animals treated with Compound 107 during the immunization, the percentage of OT-I memory T cells was significantly increased beyond that observed in the vehicle-treated immunized/boosted group.

In Vivo Tumor Growth Inhibition

Figure 4A:
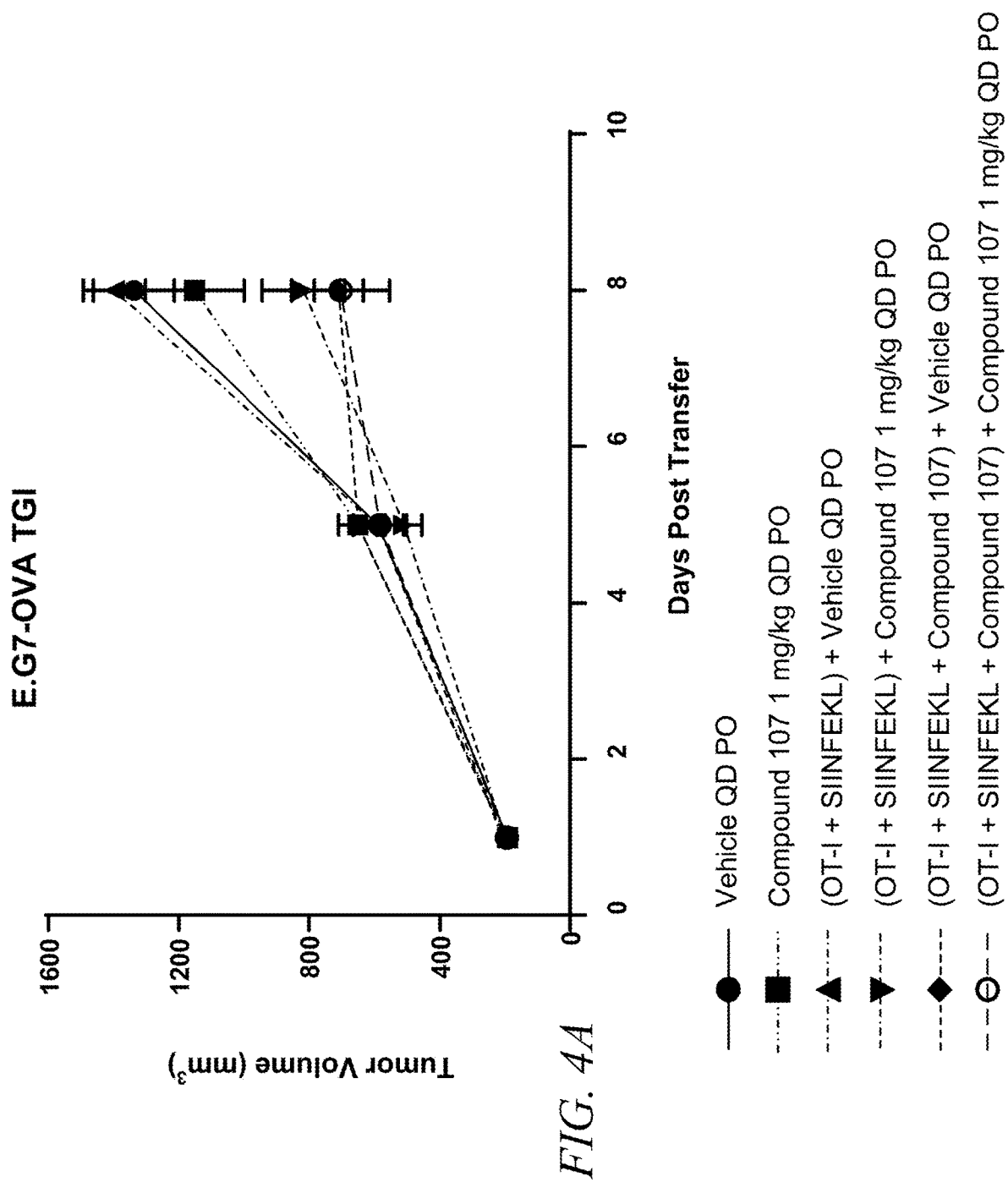
FIGS. 4A-4B show that MNK-specific inhibitor enhances in vivo efficacy of adoptively transferred T cells in animal tumor model. Athymic nude mice were subcutaneously implanted with E.G7-OVA cells, size-matched and randomized prior to adoptive transfer of OT-I T cells as indicated.
Figure 4B:
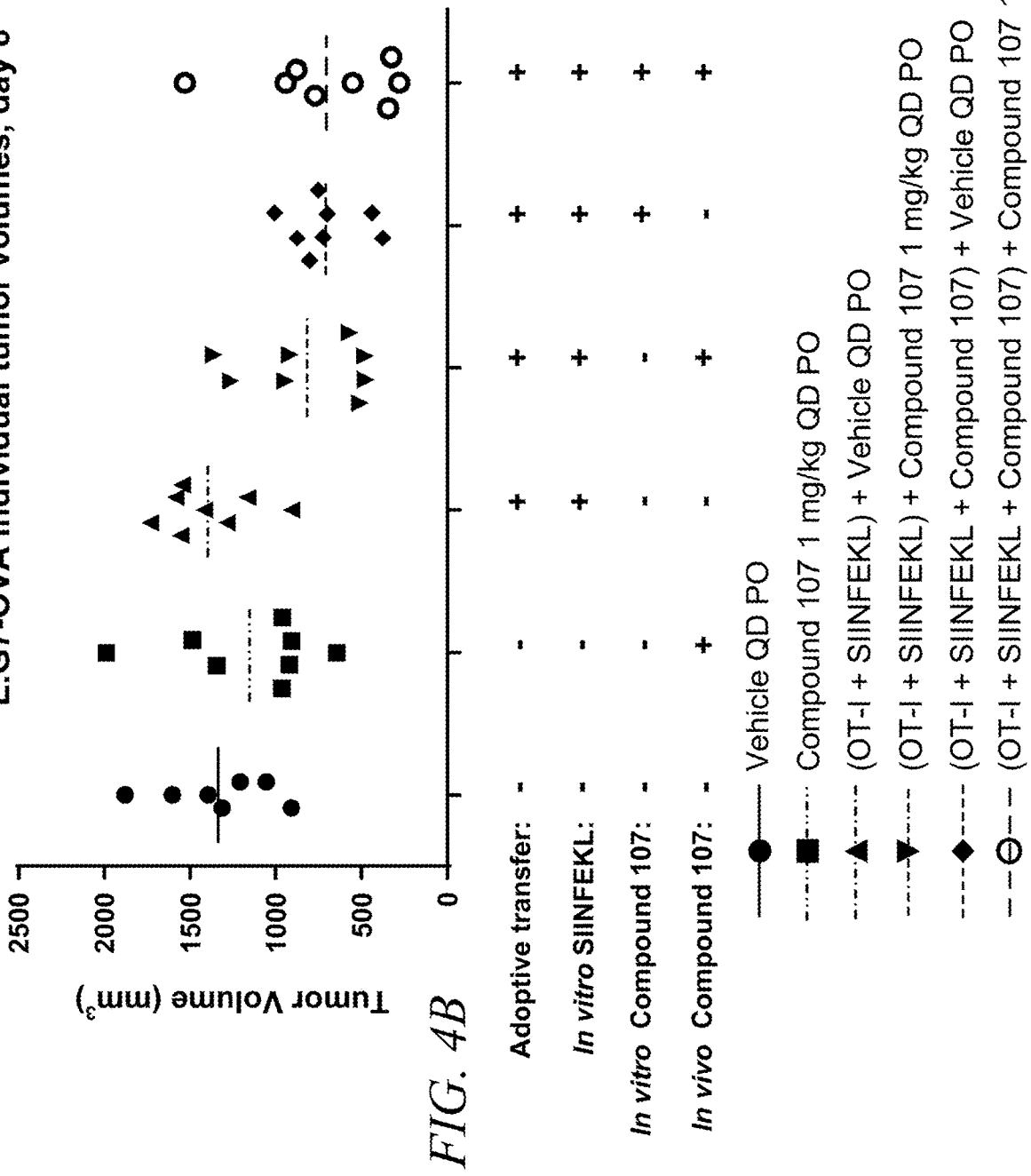

In order to functionally assess whether the increased long-term memory/recall response elicited by Compound 107 translated to enhanced anti-tumor efficacy, an in vivo tumor growth inhibition study was carried out. In this experiment, athymic nude mice were implanted subcutaneously with E.G7-OVA cells. At 7 d post-implant, OT-I T cells that had been pre-treated in vitro with SIINFEKL peptide (SEQ ID NO:1) alone, Compound 107 alone, or the combination of SIINFEKL (SEQ ID NO:1) and Compound 107, were adoptively transferred into selected animal groups. Animals were then dosed daily with vehicle or 1 mg/kg Compound 107 and tumor size was monitored (FIGS. 4A, 4B). At 8 days post-transfer, E.G7-OVA tumor-bearing animals that did not receive an adoptive transfer of OT-I T cells showed minor tumor growth inhibition (TGI, 16%) in response to Compound 107 dosing compared to vehicle. However, E.G7-OVA tumors in Compound 107-dosed animals that did receive an adoptive transfer of SIINFEKL-pre-treated cells showed a TGI of 45%, demonstrating that the anti-tumor effect of Compound 107 is enhanced through T cells in this model. Interestingly, E.G7-OVA tumors in vehicle-dosed animals that received OT-I cells pre-treated with SIINFEKL (SEQ ID NO:1) and Compound 107 showed a TGI of 55%, while a similar adoptively-transferred group of animals did not show any further increase in TGI when dosed in vivo with Compound 107. Taken together, these efficacy results are consistent with the findings that Compound 107 can enhance T cell memory formation in vivo.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A modified T cell, comprising a chromosomal MNK gene knock out, wherein the MNK gene comprises the MNK1 gene, the MNK2 gene, or both; optionally further comprising a transgene encoding an engineered antigen specific receptor.

2. The modified T cell of claim 1, wherein the encoded engineered antigen specific receptor is a chimeric antigen receptor (CAR), a T cell receptor (TCR), a TCR-CAR, or any combination thereof.

3. The modified T cell of claim 2, wherein the encoded CAR comprises a binding domain comprising an scFv that specifically binds to the antigen.

4. The modified T cell of claim 2, wherein the encoded CAR comprises at least one signaling domain.

5. The modified T cell of claim 2, wherein the encoded T cell receptor is an enhanced affinity TCR.

6. The modified T cell of claim 2, wherein the encoded TCR is an αβTCR or a γδTCR.

7. The modified T cell of claim 1, wherein both MNK1 and MNK2 are knocked out.

8. The modified T cell of claim 1, wherein the antigen is a tumor antigen, a pathogenic microorganism antigen, or an autoimmune disease antigen.

9. The modified T cell of claim 8, wherein the tumor antigen is selected from the group consisting of human immunodeficiency virus (HIV) antigens, hepatitis C virus (HCV) antigens, hepatitis B virus (HBV) antigens, cytomegalovirus (CMV) antigens, Epstein Barr virus (EBV) antigens, parasitic antigens, ROR1, EGFR, EGFRvIII, HPV E6, HPV E7, L1-CAM, Lewis A, Lewis Y, MUC1, MUC16, PSMA, CD19, CD20, CD22, CD56, CD23, CD24, CD30, CD33, CD37, CD38, CD44v6, CD72, CD79a, CD79b, CD97, CD123, CD171, CD179a, CA125, c-MET, FcRH5, WT1, VEGF-α, VEGFR1, VEGFR2, IL-13Rα2, IL-11Rα, MAGE, MAGE-Al, ephrin A2, ephrin B2, NKG2D ligands, NY-ESO-1, TAG-72, mesothelin, glioma-associated antigen, carcinoembryonic antigen (CEA), IL-13Rα, FAP, B7H3, Kit, CA-IX, CS-1, BCMA, bcr-abl, β-human chorionic gonadotropin, α-fetoprotein (AFP), ALK, cyclin B1, lectin-reactive AFP, Fos-related antigen 1, ADRB3, thyroglobulin, RAGE-1, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, PLAC1, RU1, RU2 (AS), intestinal carboxyl esterase, sLe, LY6K, M-CSF, MYCN, RhoC, TRP-2, CYP1B1, BORIS, prostase, prostate-specific antigen (PSA), PAX3, PAP, LAGE-1a, LMP2, NCAM, p53, p53 mutant, Ras mutant, gp100, prostein, OR51E2, PANX3, PSCA, hTERT, HMWMAA, HAVCR1, survivin, telomerase, legumain, sperm protein 17, SSEA-4, tyrosinase, TARP, ML-IAP, MAD-CT-1, MAD-CT-2, MelanA/MART1, XAGE1, ELF2M, ERG (TMPRSS2 ETS fusion gene), NA17, neutrophil elastase, sarcoma translocation breakpoints, NY-BR-1, androgen receptor, insulin growth factor (IGF)-I, IGF-II, IGF-I receptor, GD2, o-acetyl-GD2, GD3, GM3, GPRC5D, GPR20, CXORF61, folate receptor alpha (FRα), folate receptor beta, Tie 2, TSHR, UPK2, Tn Ag, FLT3, PRSS21, PDGFR-beta, ERBB2 (Her2/neu), CAIX, TEM1/CD248, TEM7R, CLDN6, polysialic acid, PCTA-1/Galectin 8, mut hsp70-2, LAIR1, FCAR, LILRA2, CD300LF, CLEC12A, BST2, EMR2, LY75, GPC3, FCRL5, IGLL1, and psor.

10. The modified T cell of claim 1, further comprising an inhibited TCR gene, an inhibited HLA gene, an immunosuppression component gene, or any combination thereof.

11. The modified T cell of claim 10, wherein the inhibited TCR gene is TRA, TRB, or both.

12. The modified T cell of claim 10, wherein the inhibited HLA gene is a HLA class I gene or an HLA class II gene, or both.

13. The modified T cell of claim 10, wherein the inhibited immunosuppression component gene is PD-1, CTLA-4, VISTA, BTLA, KIR, LAG3, TIM-3, A2AR, CD244 (2B4), CD160, TIGIT, PVRIG (CD112R), arginase, indoleamine 2,3-dioxygenase (IDO), IL-10, IL-4, IL-1RA, IL-35, or any combination thereof.

14. The modified T cell of claim 10, wherein the TCR gene, the HLA gene, the immune checkpoint molecule gene, or any combination thereof is knocked out, or is inhibited at the gene level, transcriptional level, translational level or any combination thereof.

15. The modified T cell of claim 10, wherein the inhibited TCR gene, the inhibited HLA gene, the immunosuppression component gene, or any combination thereof comprise an inhibitory nucleic acid.

16. The modified T cell of claim 15, wherein the inhibitory nucleic acid is an antisense oligonucleotide, a double stranded RNA (dsRNA) molecule, a siRNA molecule, an endoribonuclease-prepared siRNA (esiRNA), or an shRNA molecule.

17. The modified T cell of claim 1, wherein the T cell is a CD4+ T cell or a CD8+ T cell.

18. The modified T cell of claim 1, wherein the T cell is a $CD62L^{Hi}$ T cell.

19. The modified T cell of claim 18, wherein the modified T cell is a modified CD4+ or CD8+ T cell made from:
 (a) a $CD45RA^{Hi}$ $CD62L^{Hi}$ naïve T cell-enriched CD4+ or CD8+ population, respectively;
 (b) a $CD45RO^{Hi}$ $CD62L^{Hi}$ central memory T cell-enriched CD4+ or CD8+ population, respectively;
 (c) a $CD62L^{Hi}$ naïve and central memory T cell-enriched CD4+ or CD8+ population, respectively; or
 (d) a bulk CD4+ or CD8+ T cell population, respectively, in some other embodiments, a population of modified T cells is enriched for modified CD4+ or CD8+ T cells, respectively, wherein at least 50%, at least about 60%, at least about 70%, at least about 80% or at least about 90% of the modified CD4+ or CD8+ T cells, respectively, are $CD62L^{Hi}$ or $CD62L^{Hi}$ $CD45RO^{Hi}$.

20. The modified T cell of claim 1, wherein the T cell is a human T cell.

* * * * *